United States Patent
Dothie et al.

(10) Patent No.: US 9,808,802 B2
(45) Date of Patent: Nov. 7, 2017

(54) MICROFLUIDIC DEVICE FOR SERIAL FLUIDIC OPERATIONS

(71) Applicant: Sharp Life Science (EU) Limited, Oxford (GB)

(72) Inventors: Pamela Ann Dothie, Chilton (GB); Daniel Christopher Spencer, Hampshire (GB)

(73) Assignee: SHARP LIFE SCIENCE (EU) LIMITED, Oxford (GB)

( * ) Notice: Subject to any disclaimer, the term of this patent is extended or adjusted under 35 U.S.C. 154(b) by 0 days.

(21) Appl. No.: 15/235,677

(22) Filed: Aug. 12, 2016

(65) Prior Publication Data

US 2016/0346782 A1    Dec. 1, 2016

Related U.S. Application Data

(62) Division of application No. 13/963,215, filed on Aug. 9, 2013, now Pat. No. 9,440,233.

(51) Int. Cl.
*B01L 3/00* (2006.01)
*F16K 99/00* (2006.01)
(Continued)

(52) U.S. Cl.
CPC ..... *B01L 3/502738* (2013.01); *B01L 3/50273* (2013.01); *B01L 3/502715* (2013.01);
(Continued)

(58) Field of Classification Search
CPC ......... G01N 33/4915; G01N 33/56972; G01N 15/1404; B01L 3/502738
See application file for complete search history.

(56) References Cited

U.S. PATENT DOCUMENTS 4,410,630 A    10/1983   Zierdt
5,501,982 A     3/1996   Saldivar, Jr. et al.
(Continued)

FOREIGN PATENT DOCUMENTS

DE    102009045405 A1    4/2011
EP         1535667 A1    6/2005
(Continued)

OTHER PUBLICATIONS

Extended European Search Report for corresponding European Patent Application No. 14180410.4-1361 dated Jan. 30, 2015.
(Continued)

*Primary Examiner* — Samuel P Siefke
(74) *Attorney, Agent, or Firm* — Renner, Otto, Boisselle & Sklar, LLP

(57) ABSTRACT

An integrated microfluidic device for carrying out a series of fluidic operations includes a housing including a plurality of n microfluidic conduits, wherein n is at least three, and a rotating valve having an internal channel with an entrance port and an exit port that are angularly separated. The rotating valve is positionable in a first position to connect two of the n fluidic conduits via the internal channel, and upon rotating the valve to a second position, two other of the n fluidic conduits are connected by the internal channel. The device further may include one or more fluidic chambers in fluid communication with respective fluidic conduits. Fluid contained in one fluidic chamber is transferrable by application of positive or negative gas pressure through associated fluidic conduits into another fluidic chamber via the internal channel. The device may be utilized to perform a variety of fluidic operations.

15 Claims, 47 Drawing Sheets

(51) Int. Cl.
   *G01N 33/49*     (2006.01)
   *G01N 33/569*    (2006.01)
   *G01N 15/14*     (2006.01)
   *C07C 231/02*    (2006.01)
   *G01N 33/80*     (2006.01)

(52) U.S. Cl.
   CPC ...... *B01L 3/502723* (2013.01); *C07C 231/02* (2013.01); *F16K 99/0013* (2013.01); *F16K 99/0028* (2013.01); *G01N 15/1404* (2013.01); *G01N 33/4915* (2013.01); *G01N 33/56972* (2013.01); *G01N 33/80* (2013.01); *B01L 2200/0605* (2013.01); *B01L 2200/0684* (2013.01); *B01L 2200/10* (2013.01); *B01L 2300/0627* (2013.01); *B01L 2300/0645* (2013.01); *B01L 2300/0654* (2013.01); *B01L 2300/087* (2013.01); *B01L 2300/0867* (2013.01); *B01L 2400/0478* (2013.01); *B01L 2400/0487* (2013.01); *B01L 2400/0644* (2013.01); *F16K 2099/0084* (2013.01); *F16K 2099/0086* (2013.01); *Y10T 137/0318* (2015.04); *Y10T 137/85986* (2015.04); *Y10T 137/86863* (2015.04); *Y10T 137/86919* (2015.04)

(56) References Cited

U.S. PATENT DOCUMENTS

| | | |
|---|---|---|
| 6,082,185 A | 7/2000 | Saaski |
| 6,284,548 B1 | 9/2001 | Berndtsson |
| 6,537,501 B1 | 3/2003 | Holl et al. |
| 7,420,659 B1 | 9/2008 | Cabuz et al. |
| 7,485,153 B2 | 2/2009 | Padmanabhan et al. |
| 8,222,024 B2 | 7/2012 | Davis et al. |
| 8,567,441 B2 | 10/2013 | Maeda et al. |
| 2003/0073089 A1 | 4/2003 | Mauze et al. |
| 2003/0162304 A1 | 8/2003 | Dority et al. |
| 2004/0019300 A1 | 1/2004 | Leonard |
| 2004/0109386 A1 | 6/2004 | Gold et al. |
| 2005/0255600 A1 | 11/2005 | Padmanabhan et al. |
| 2011/0079094 A1 | 4/2011 | Gransee et al. |

FOREIGN PATENT DOCUMENTS

| | | |
|---|---|---|
| EP | 1389955 B1 | 10/2009 |
| EP | 2308597 | 4/2011 |
| EP | 2556887 A1 | 2/2013 |
| WO | WO 98/22797 | 5/1998 |
| WO | WO 99/01742 | 1/1999 |
| WO | WO 02/089670 A1 | 11/2002 |
| WO | WO 03/044488 A1 | 5/2003 |
| WO | WO 03/104770 A2 | 12/2003 |
| WO | WO 03/104771 A1 | 12/2003 |
| WO | WO 03/104772 A1 | 12/2003 |

OTHER PUBLICATIONS

Restriction Requirement for related U.S. Appl. No. 13/963,215 dated Mar. 27, 2015.

Restriction Requirement for related U.S. Appl. No. 13/963,215 dated Sep. 22, 2015.

Non-Final Office Action for related U.S. Appl. No. 13/963,215 dated Feb. 26, 2016.

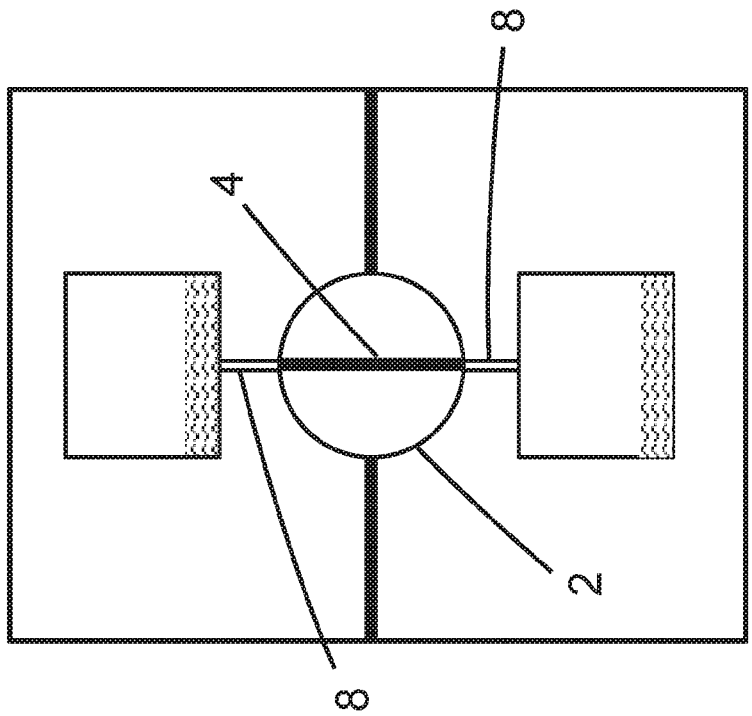
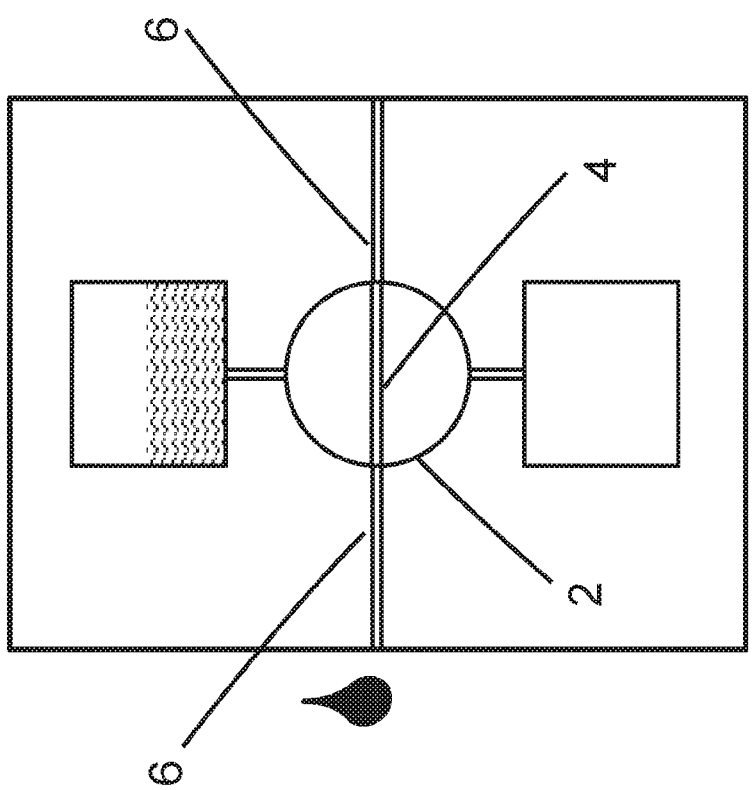

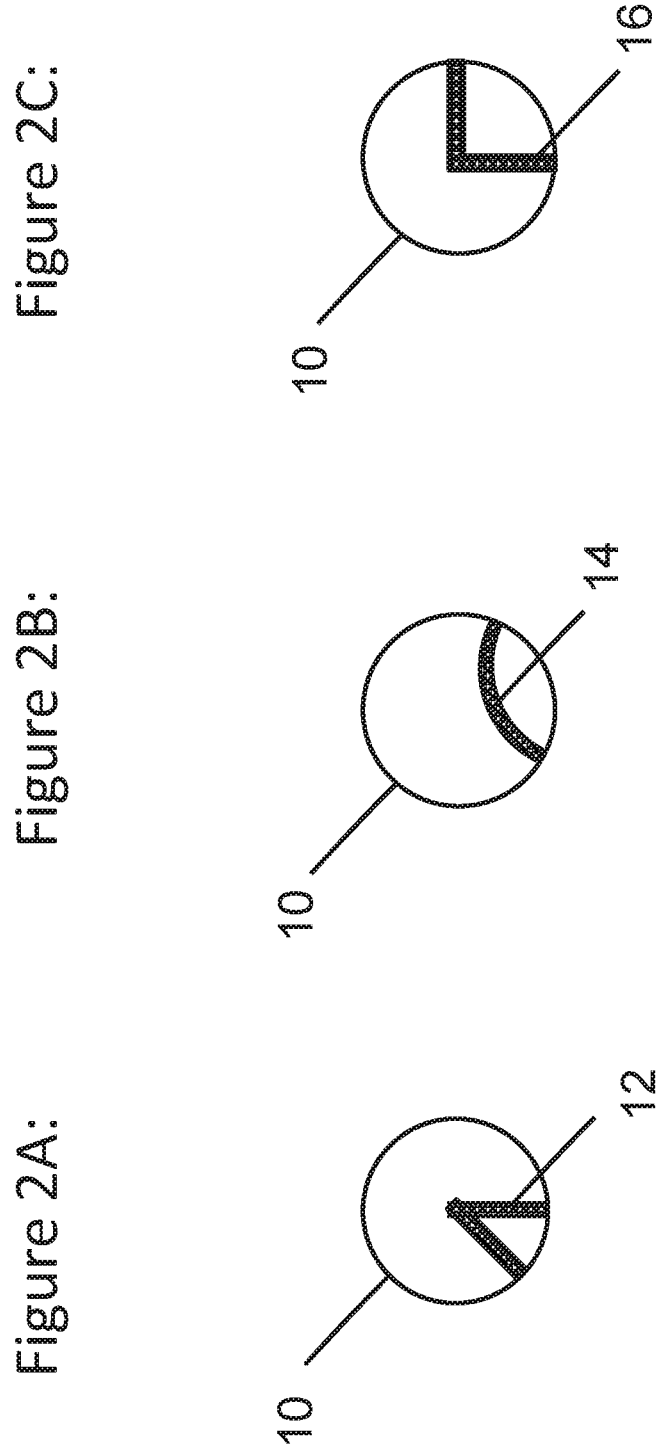

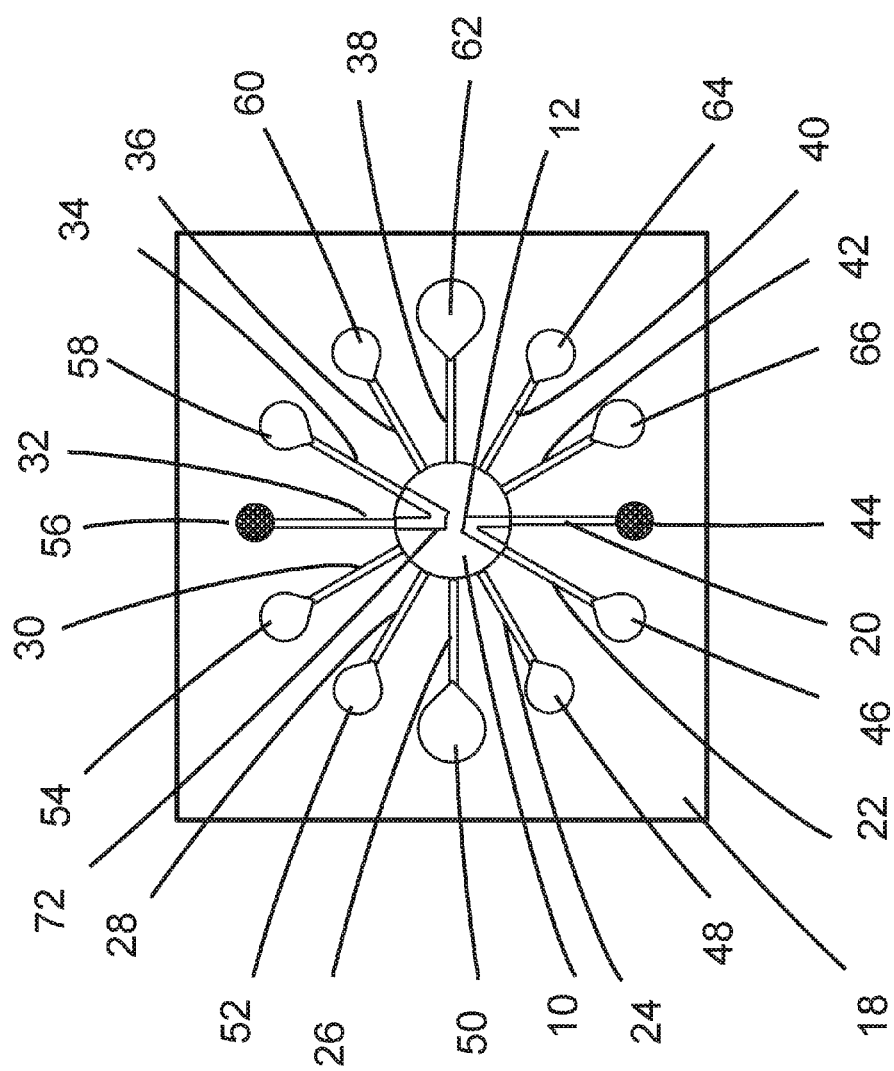

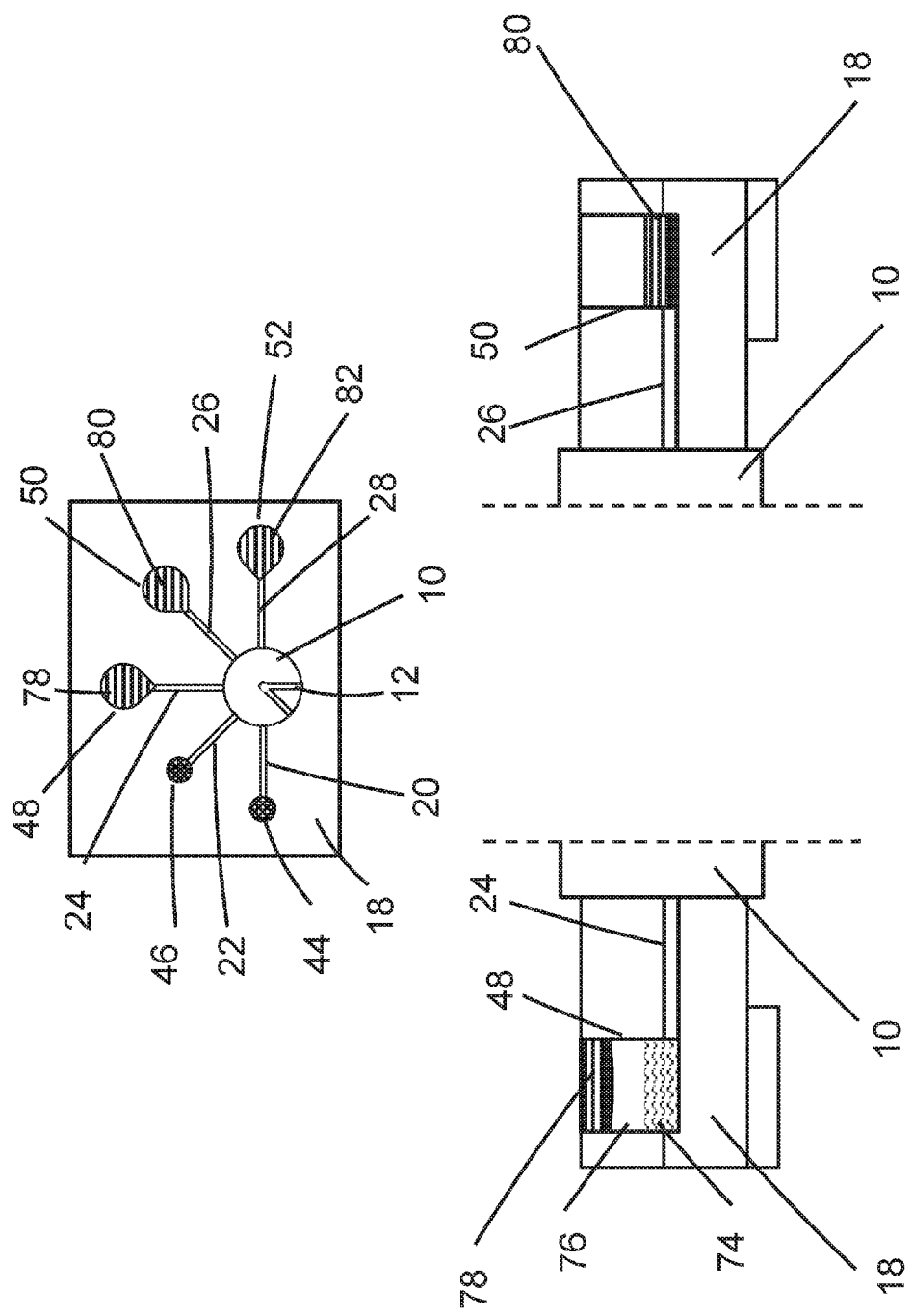

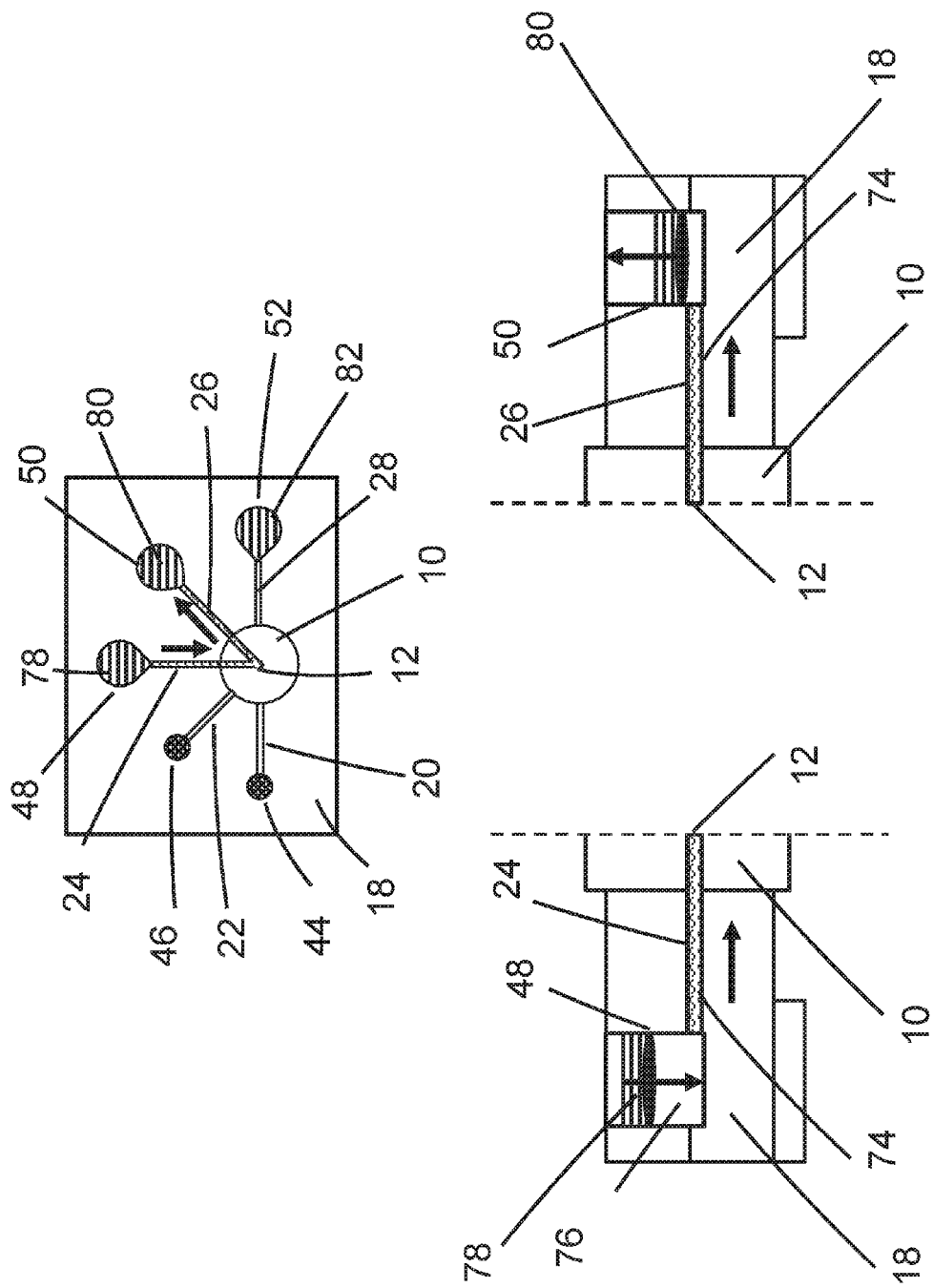

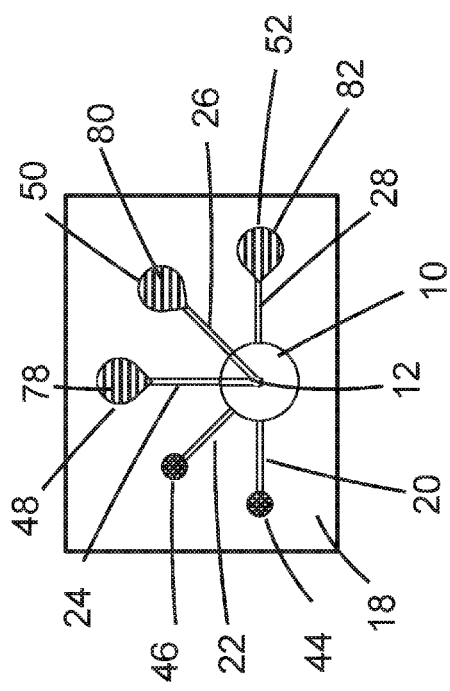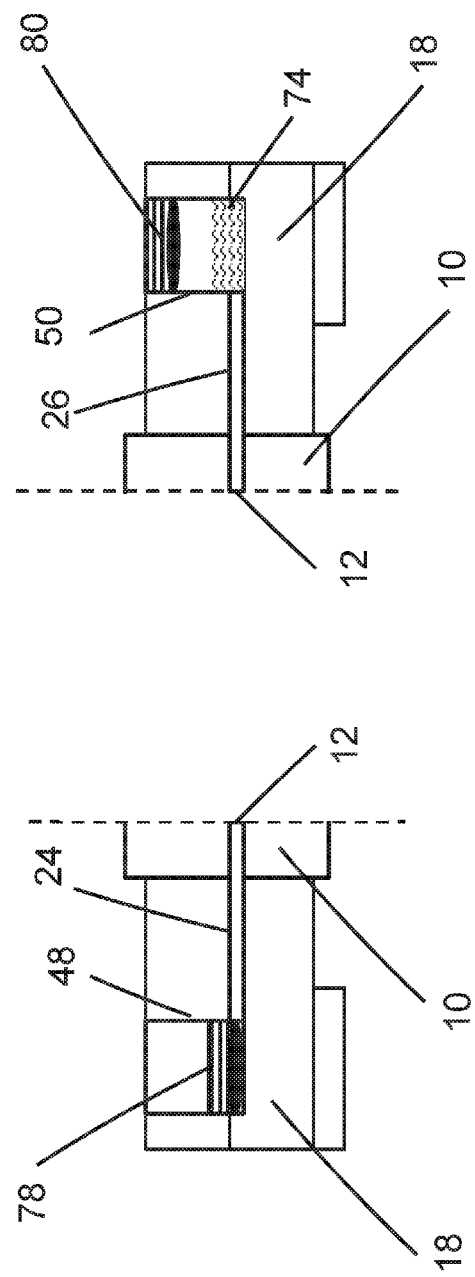

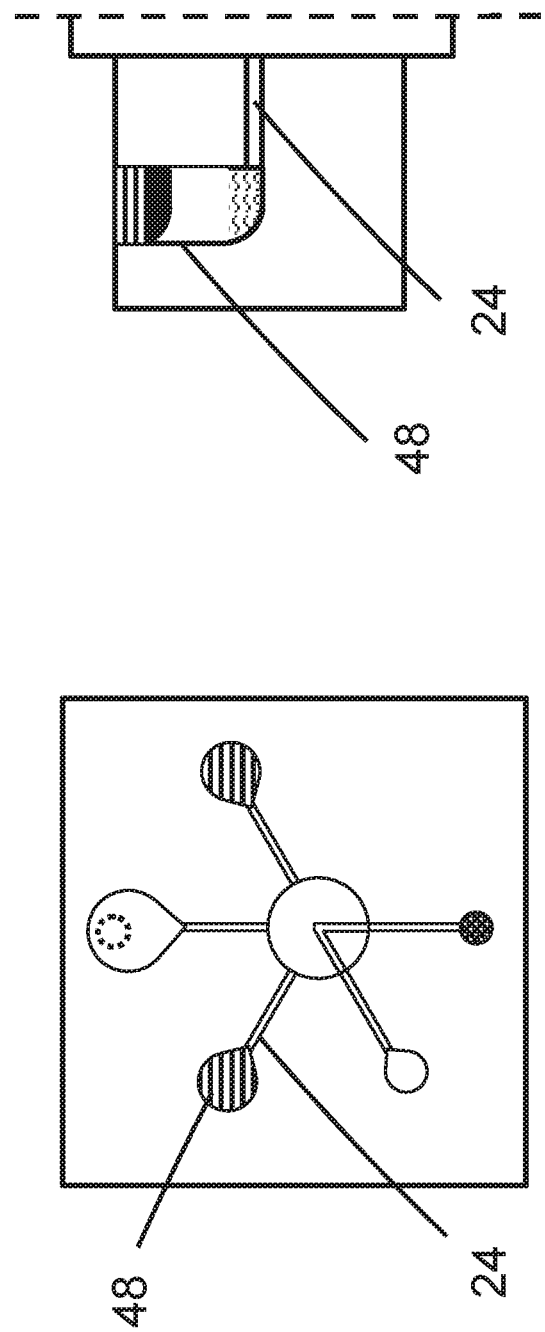

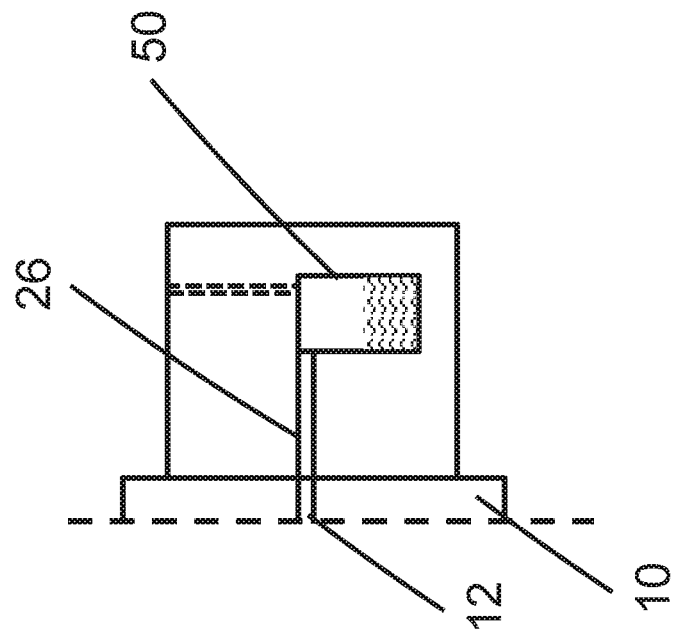
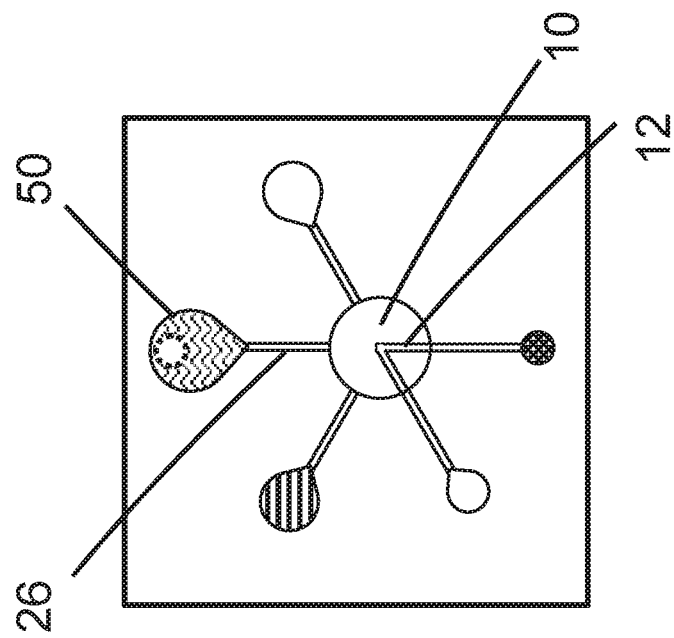
Figure 5B

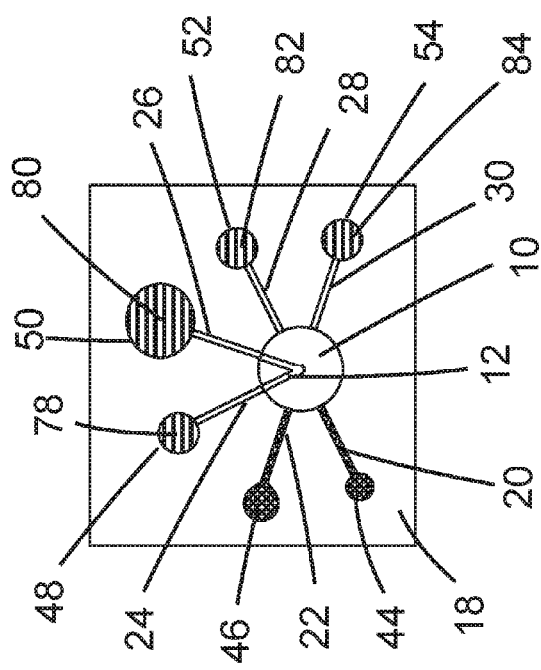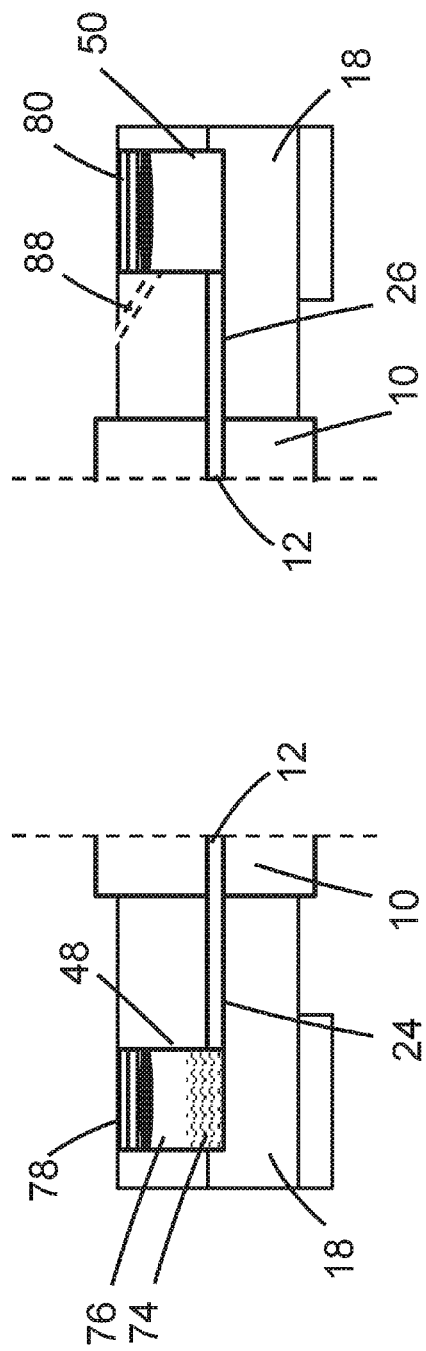
Figure 6A

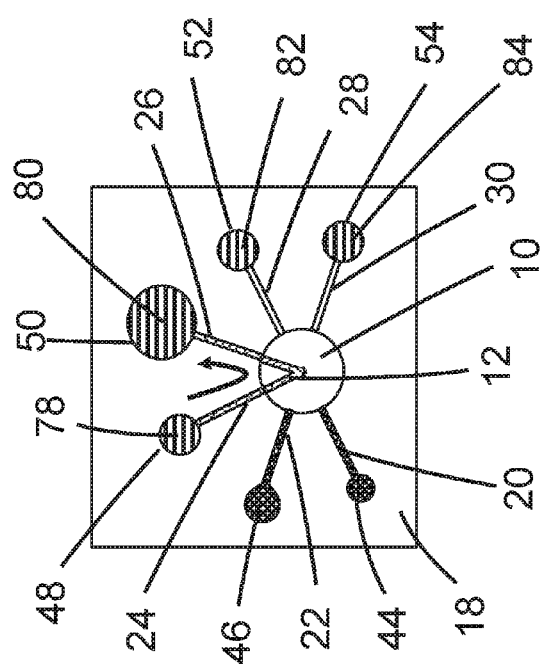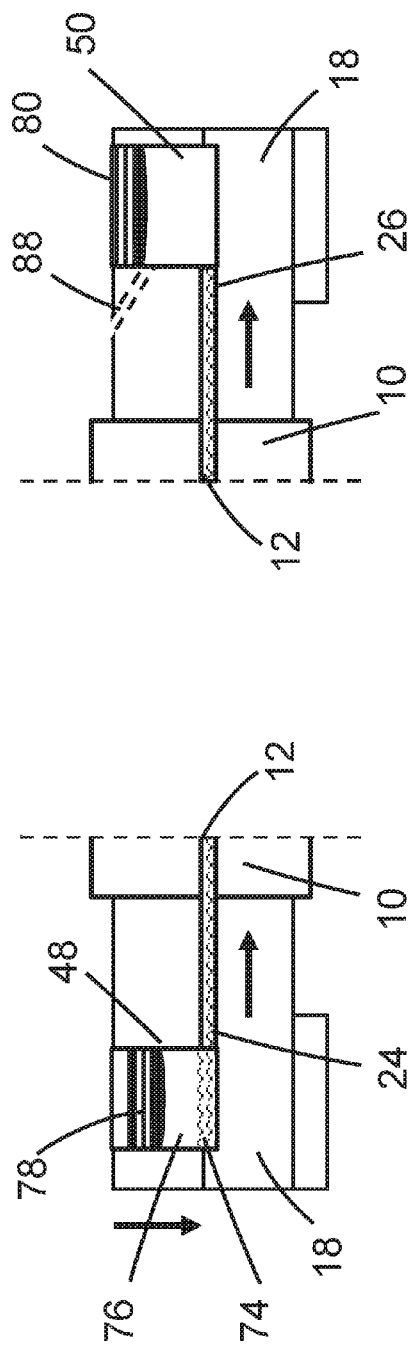

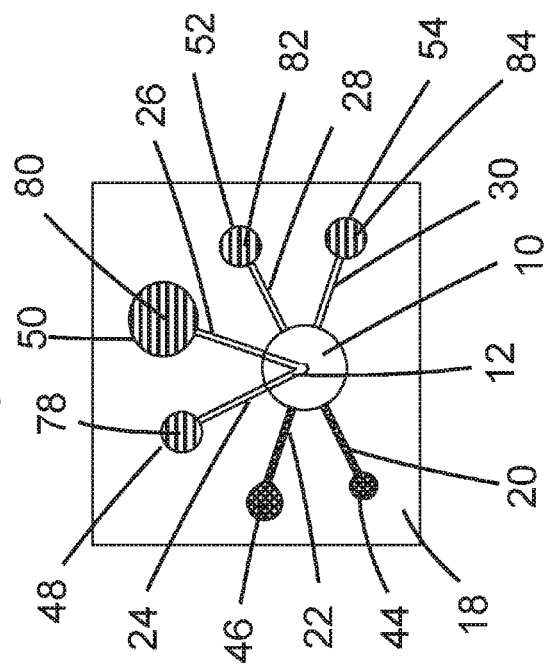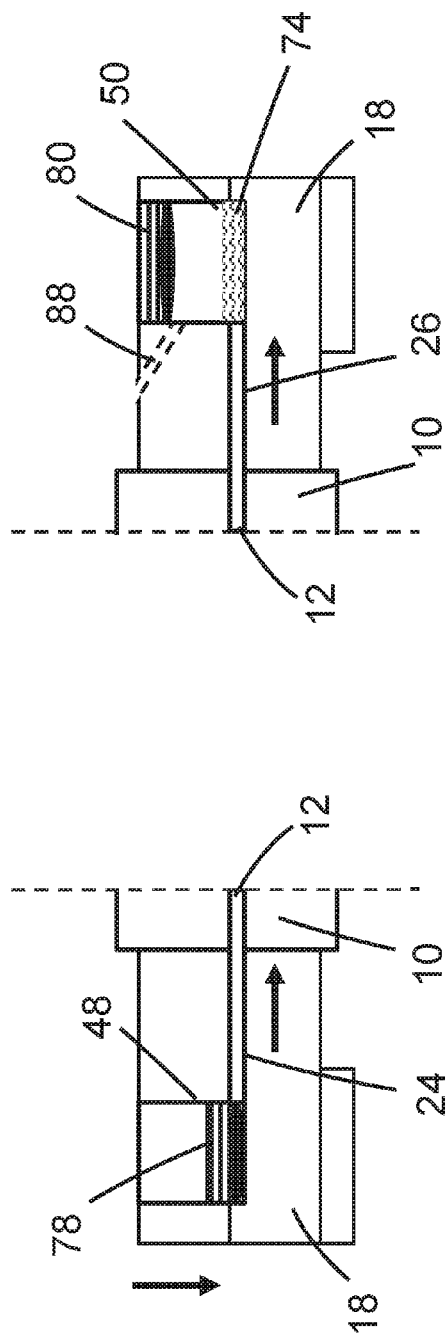

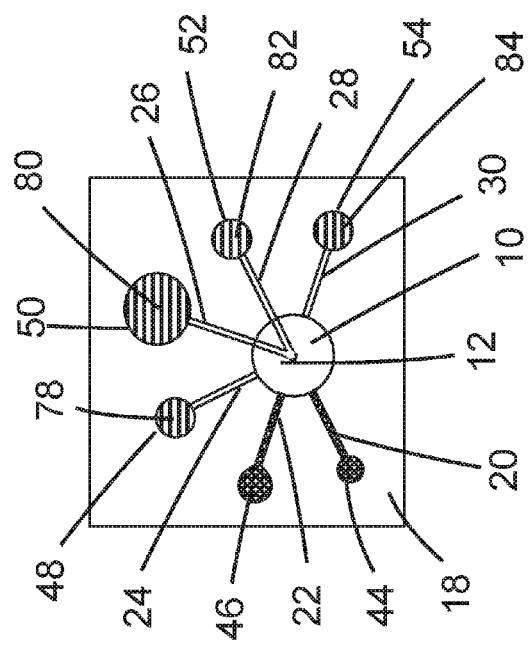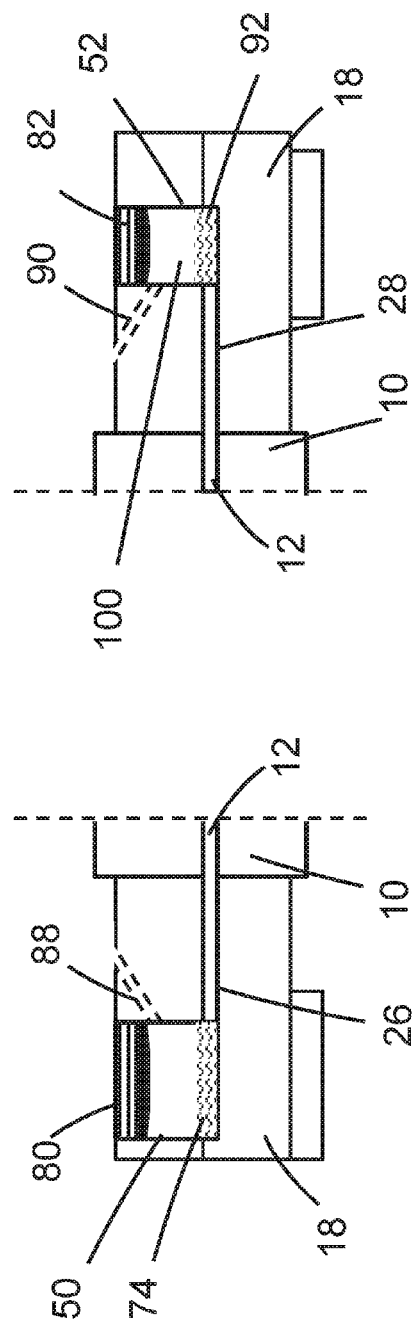

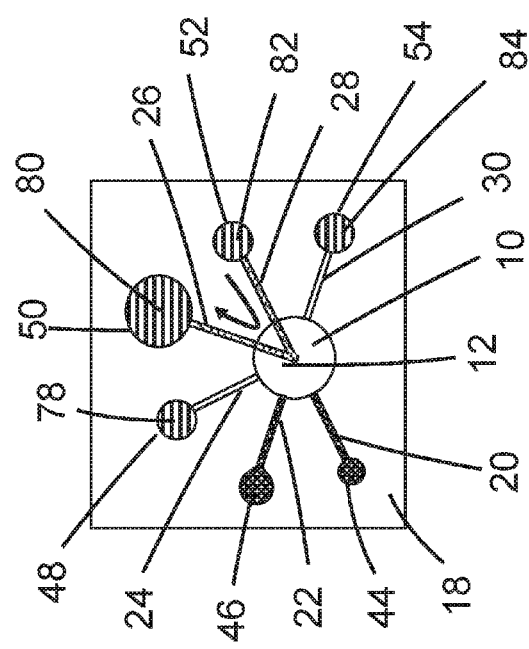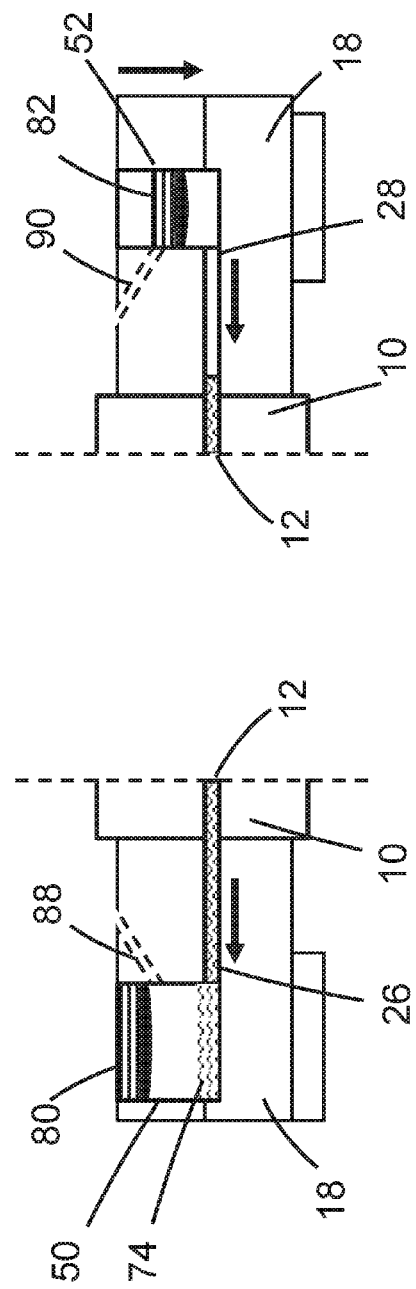

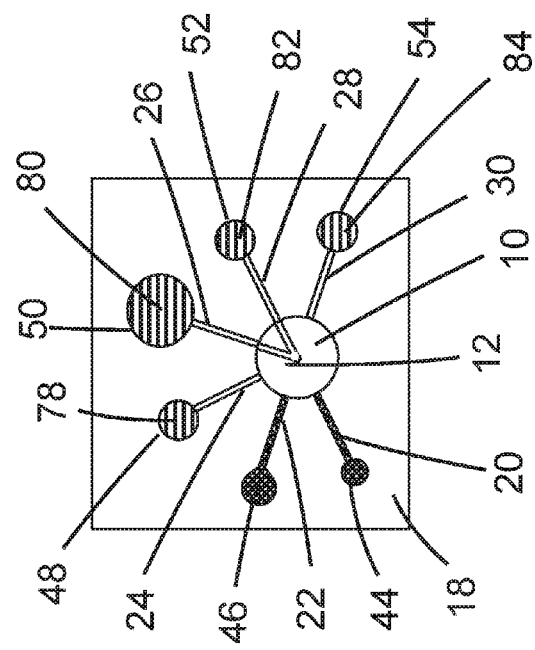
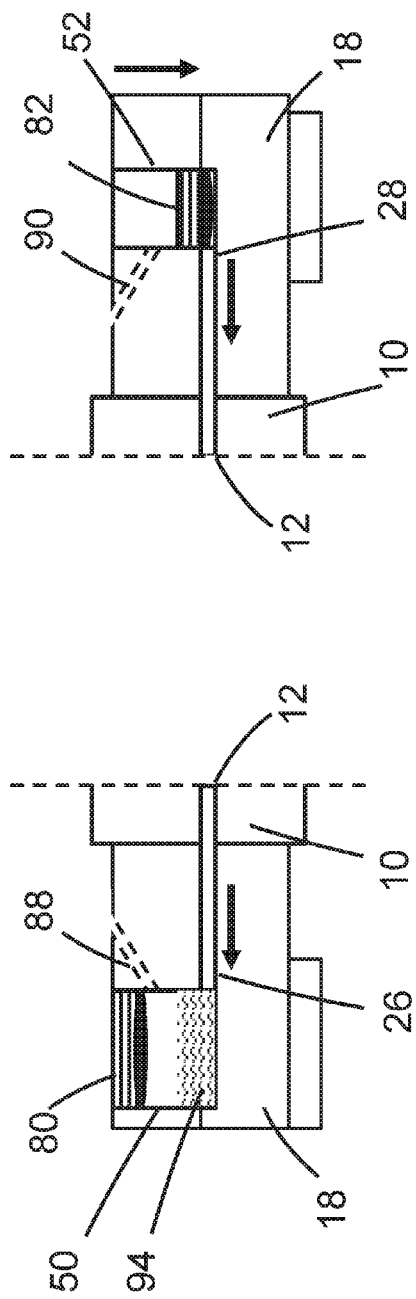
Figure 6F

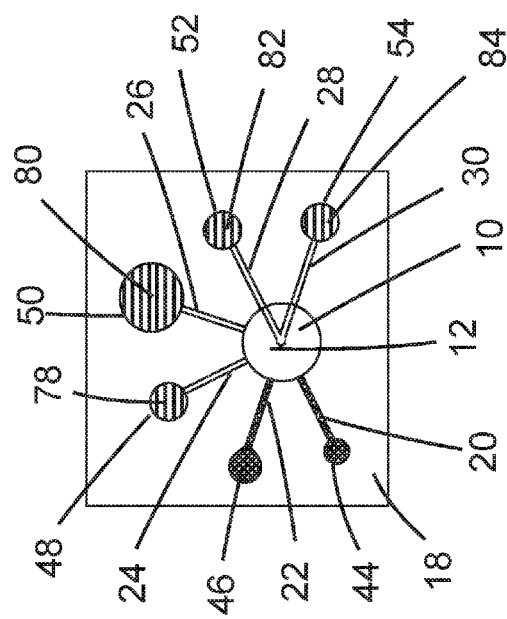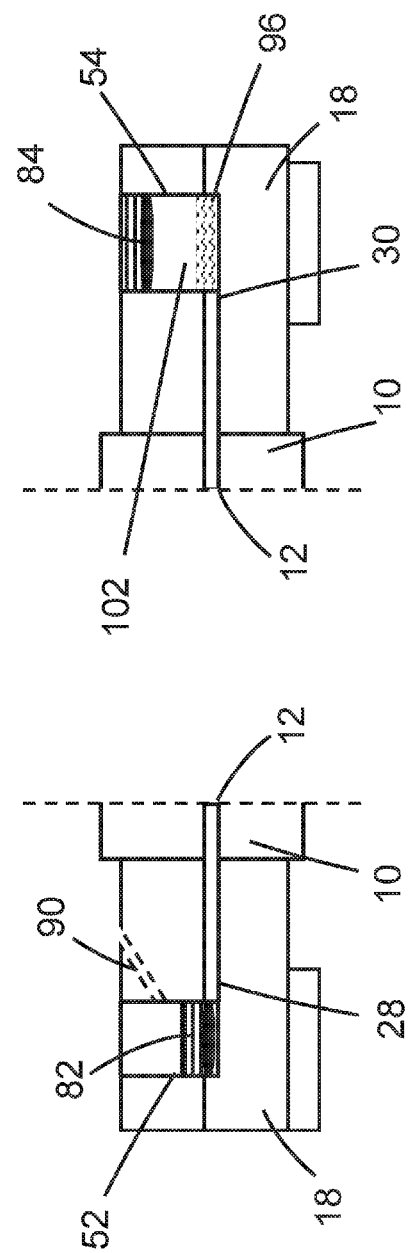
Figure 6G

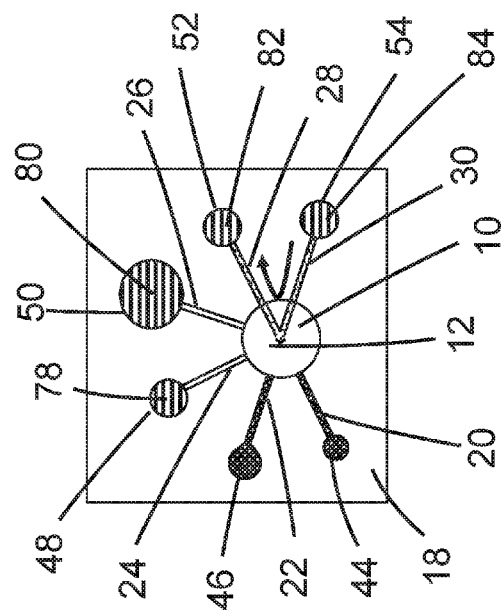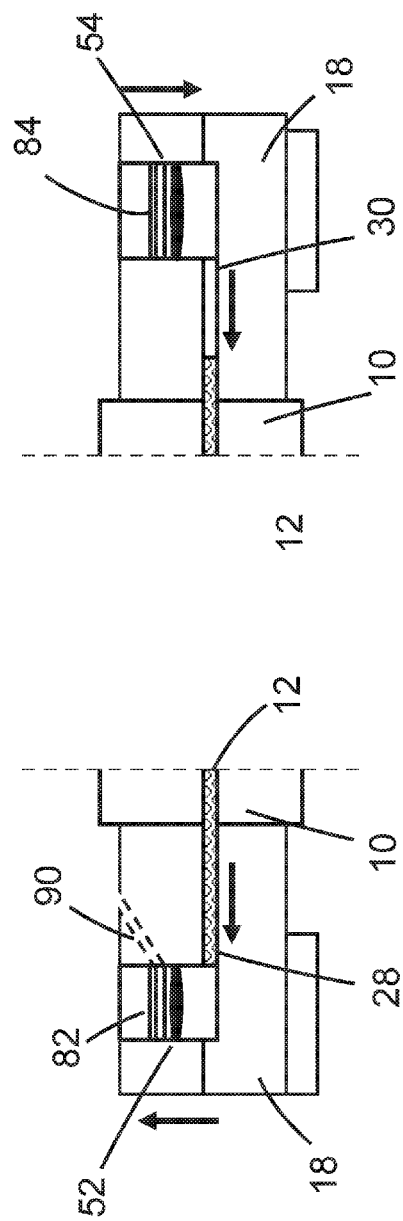

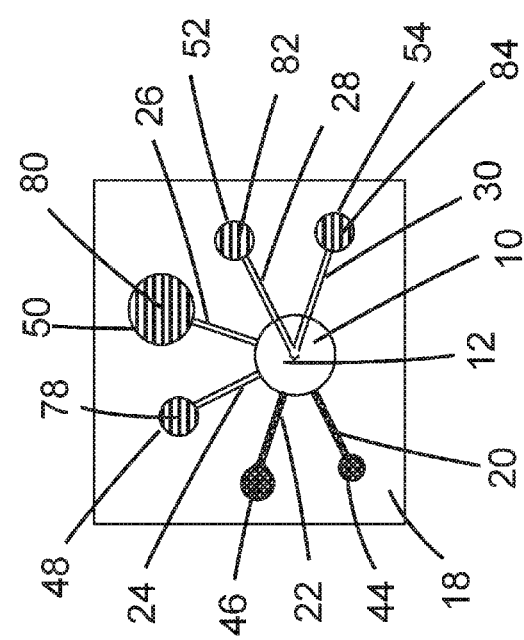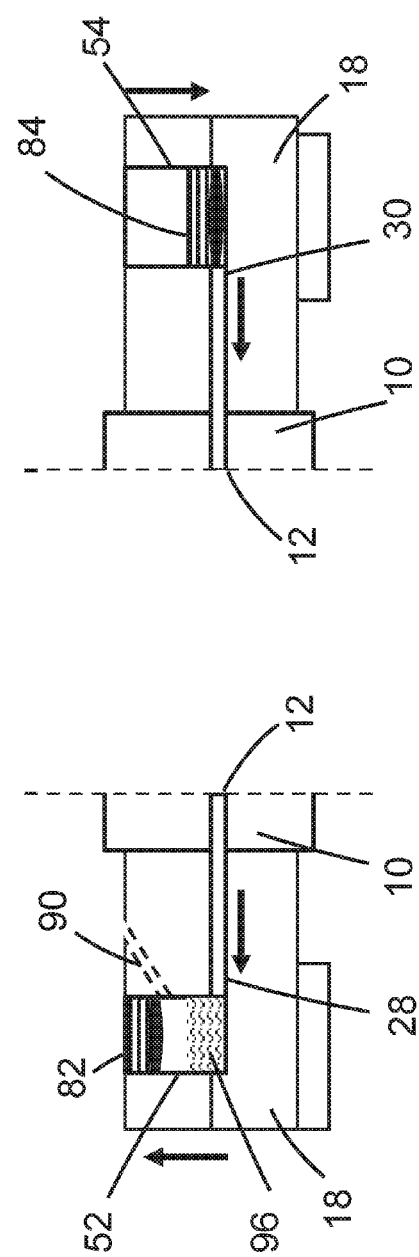
Figure 6I

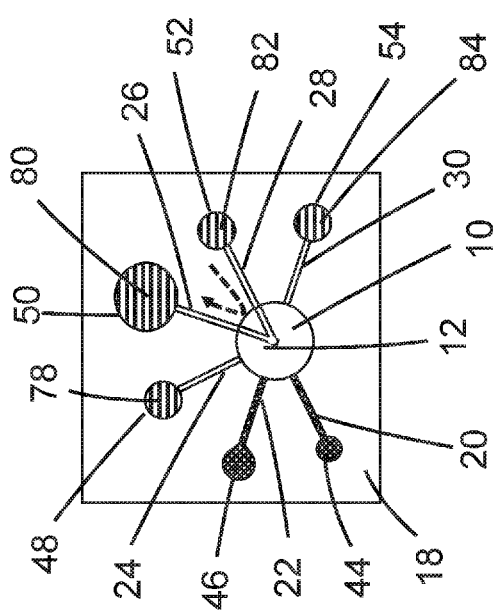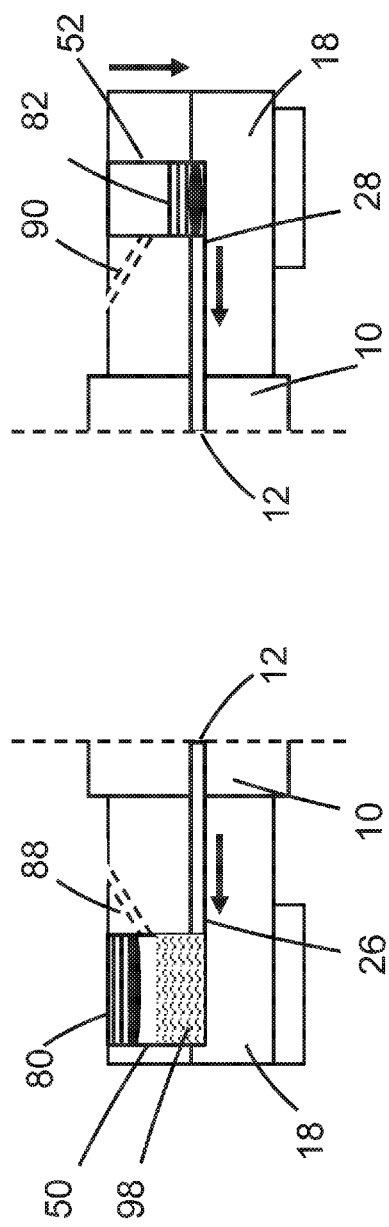

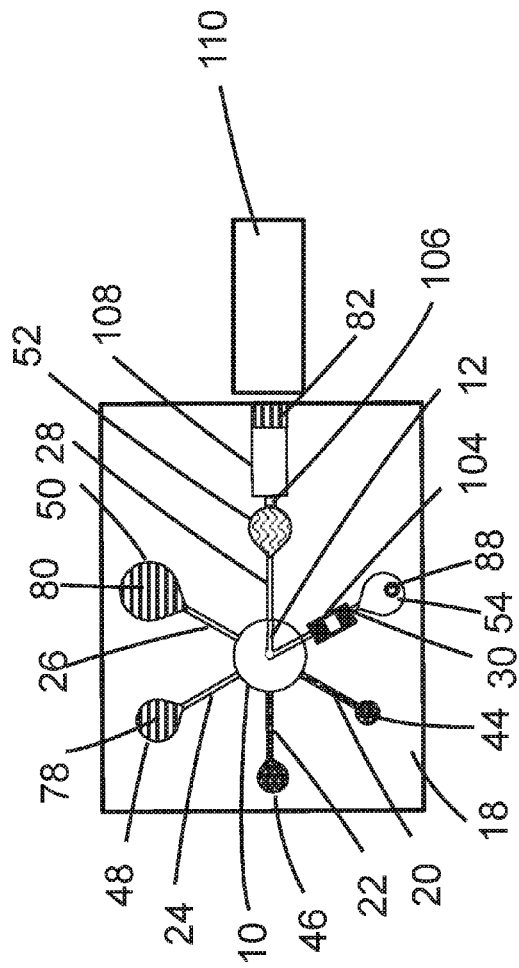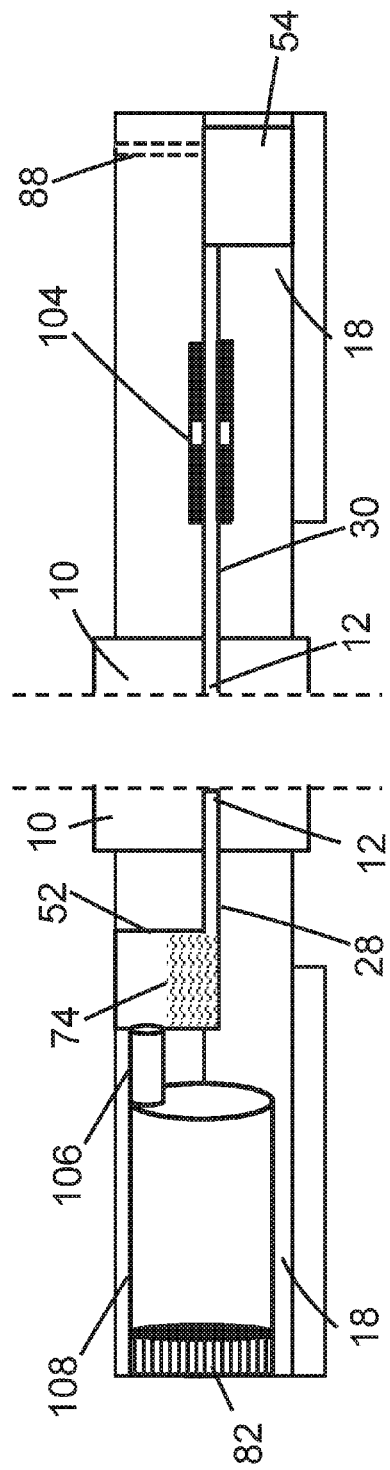
Figure 7A

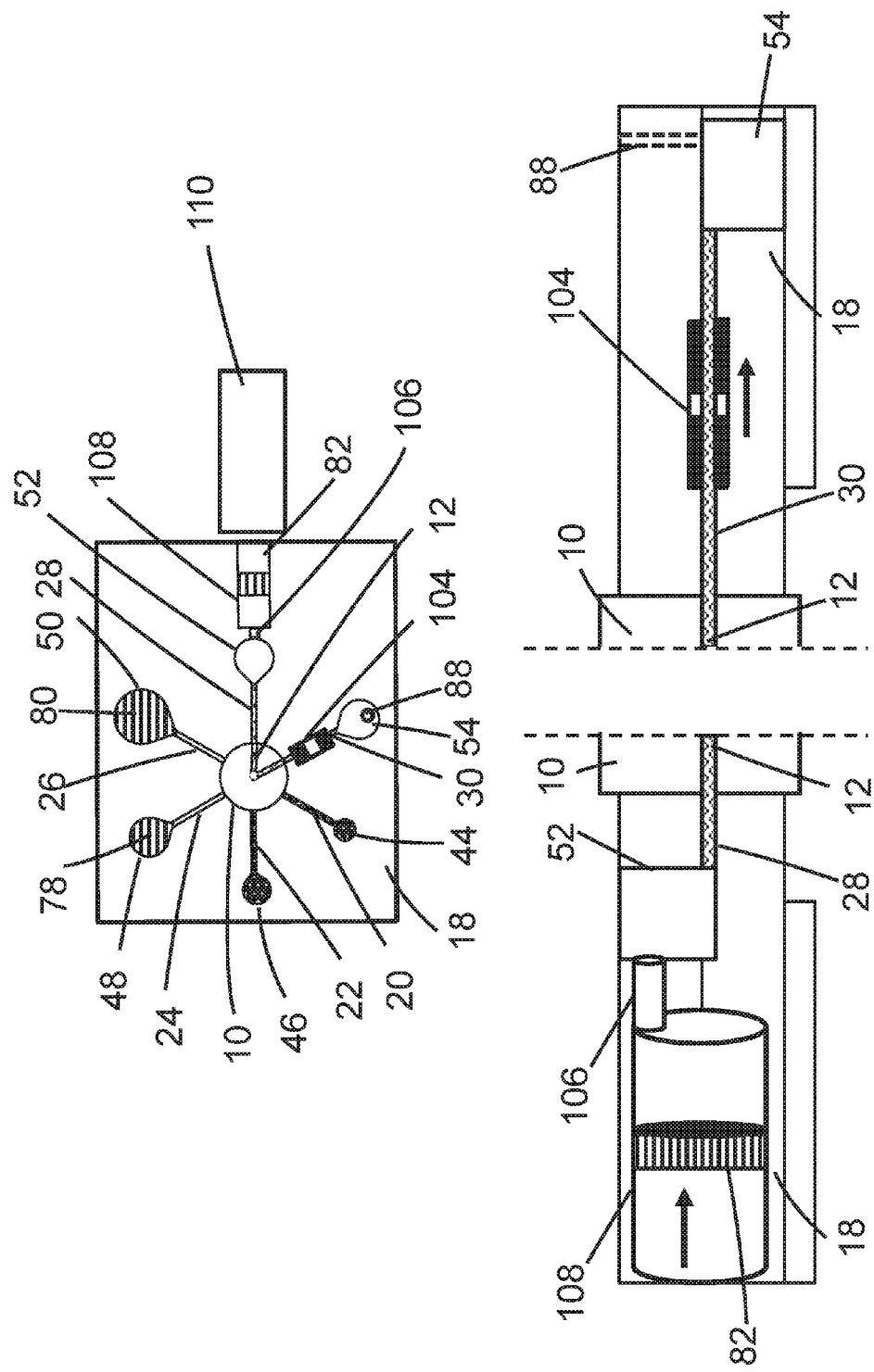

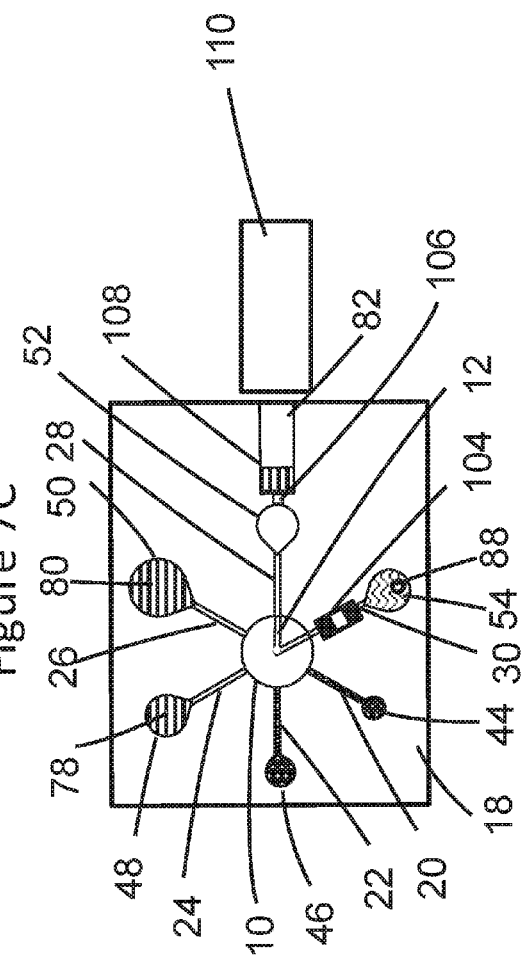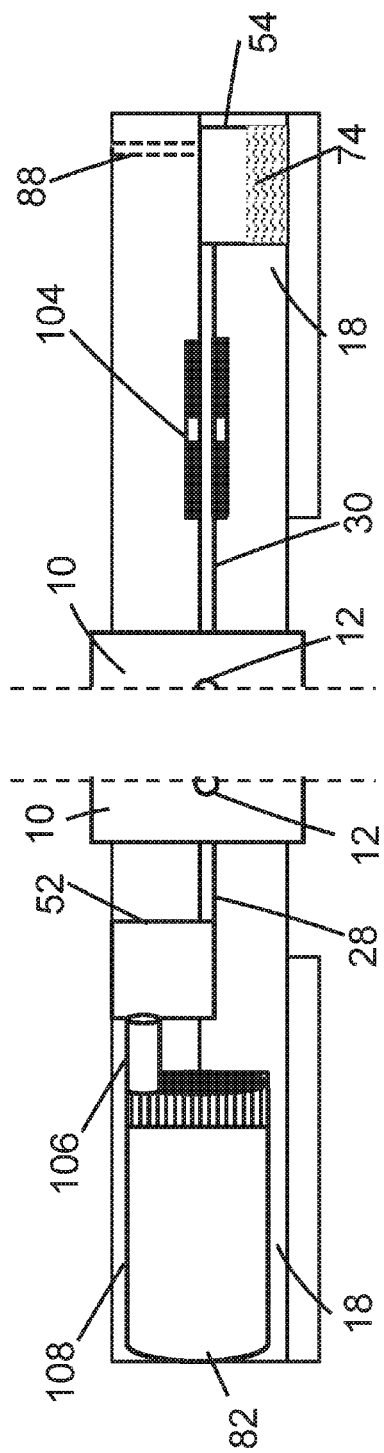
Figure 7C

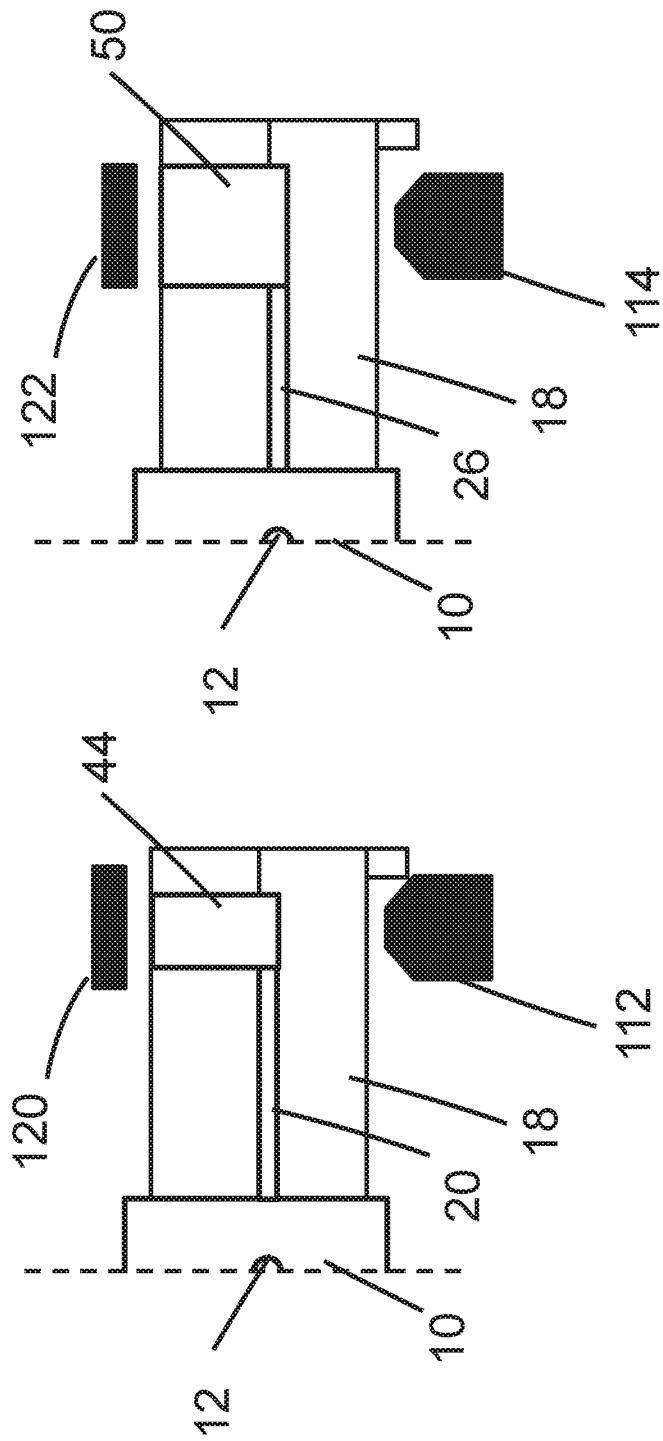

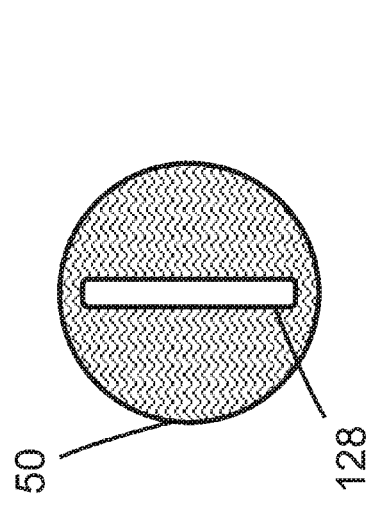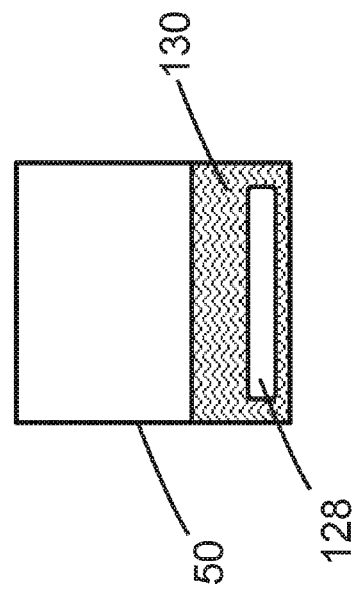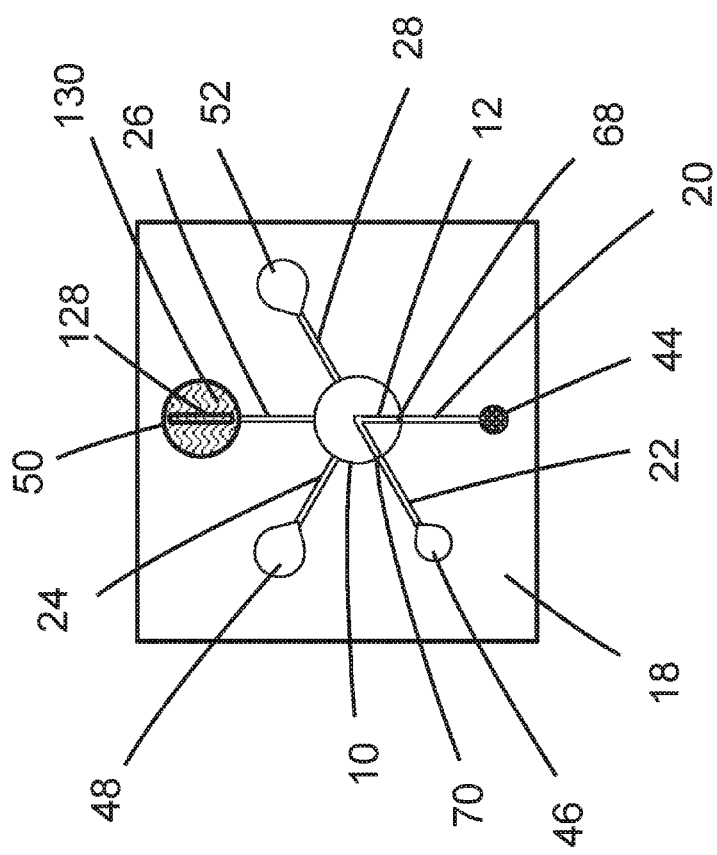

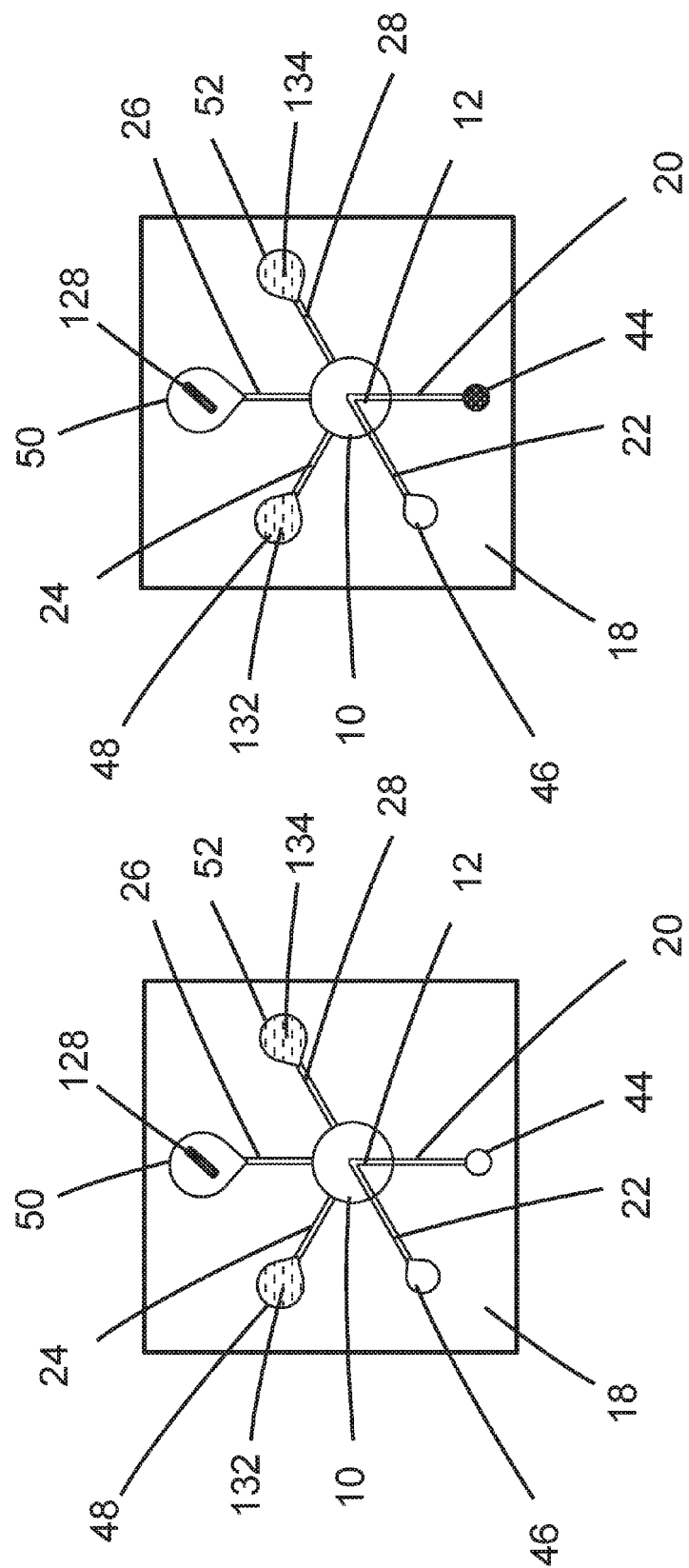

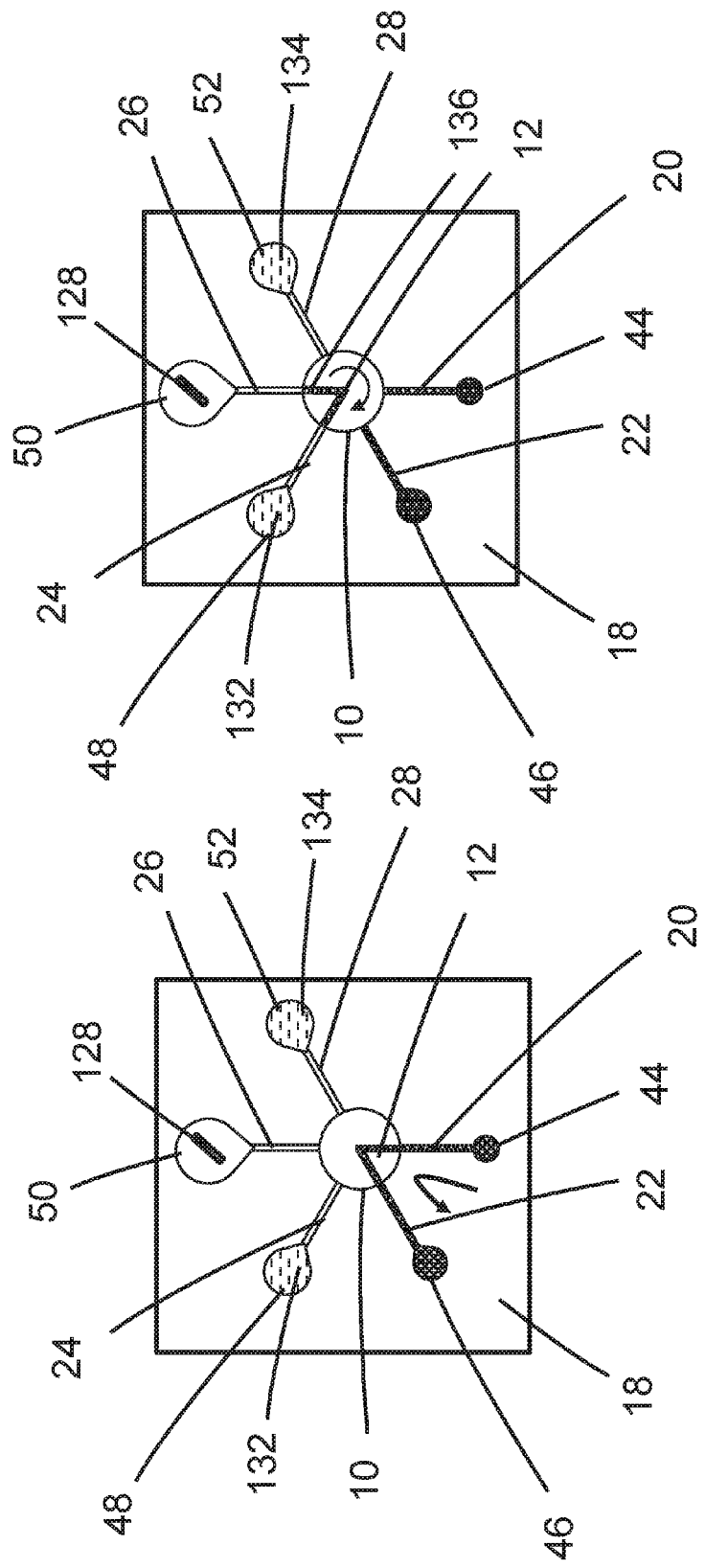

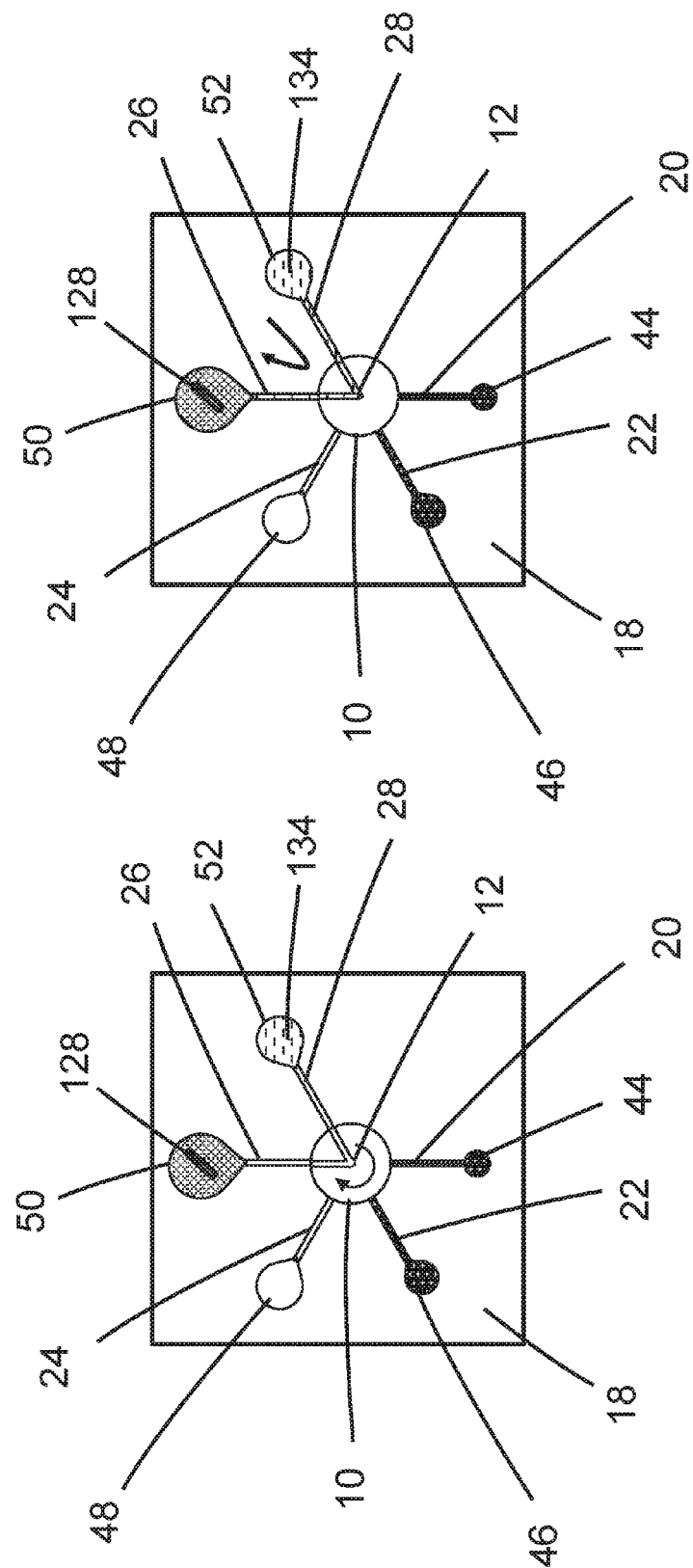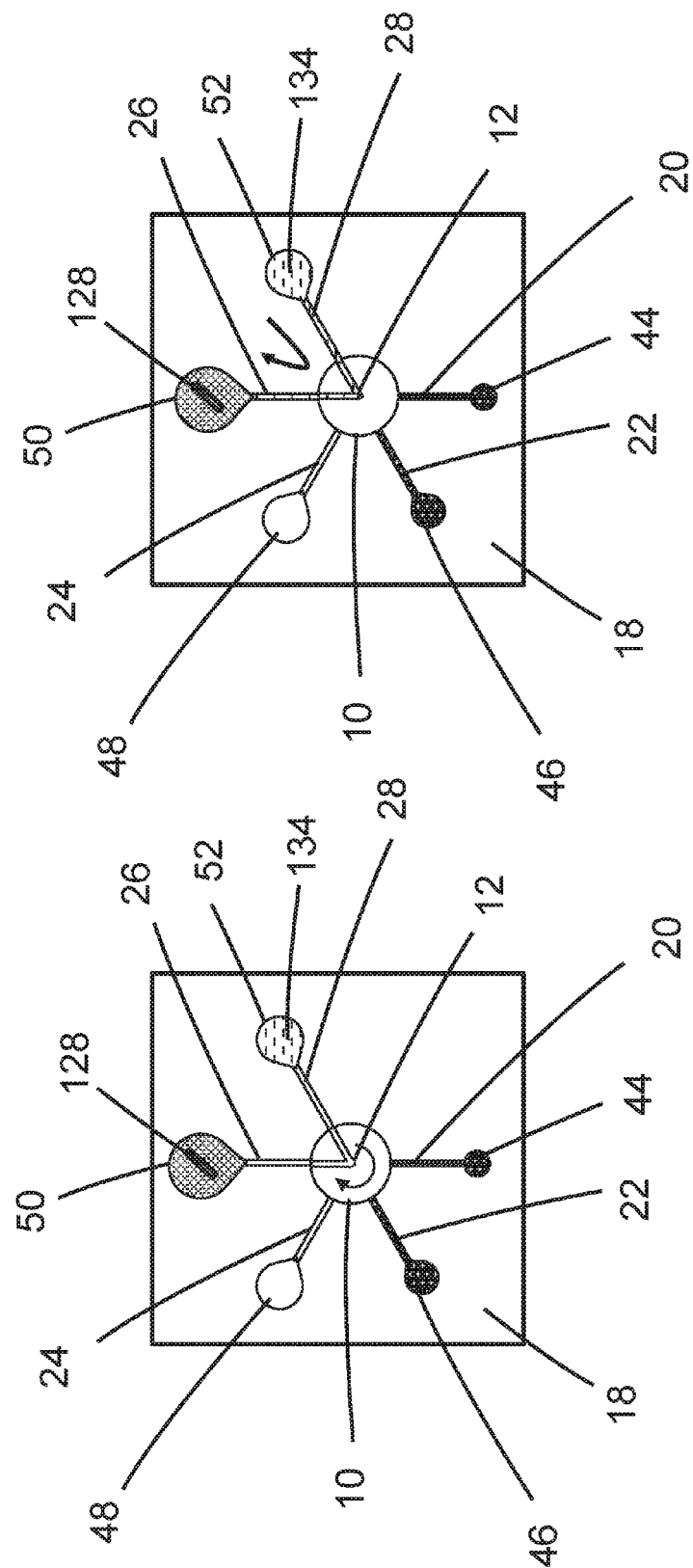

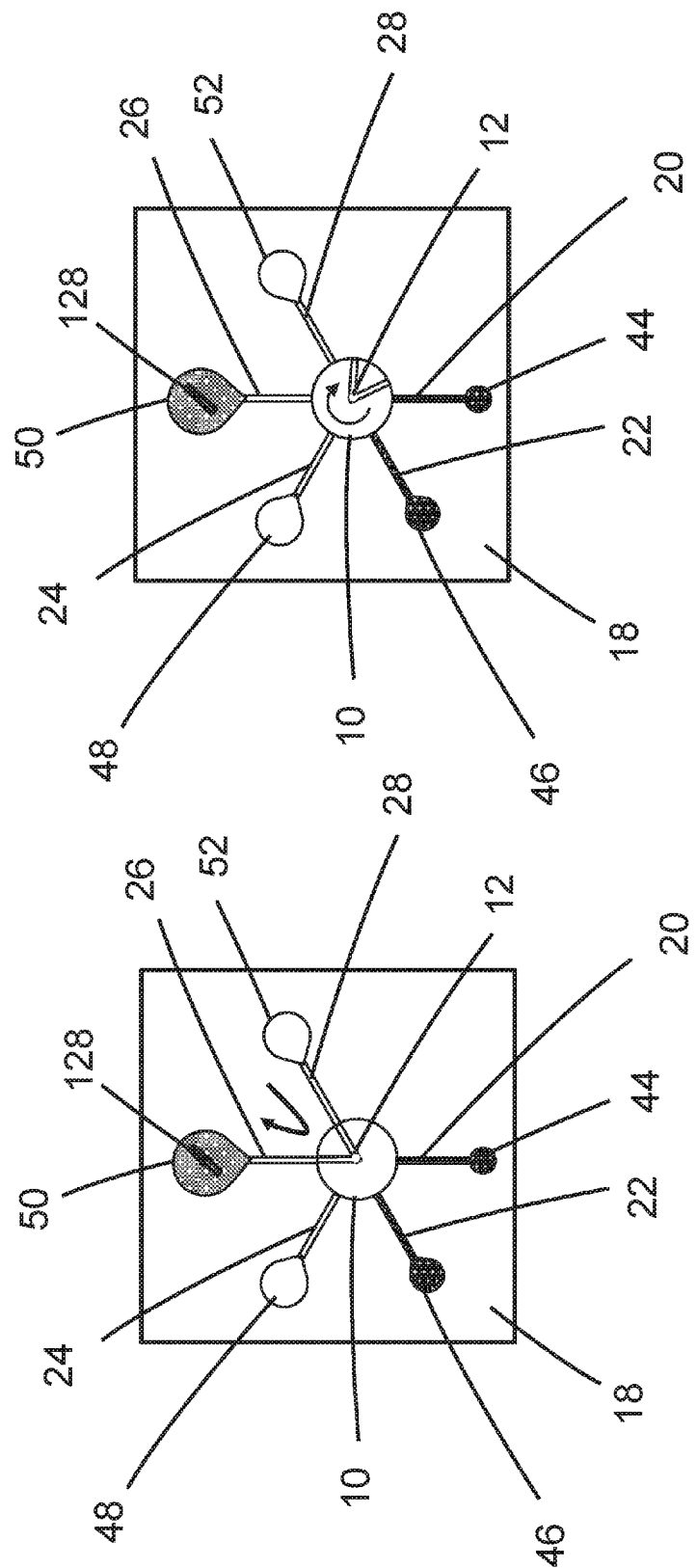

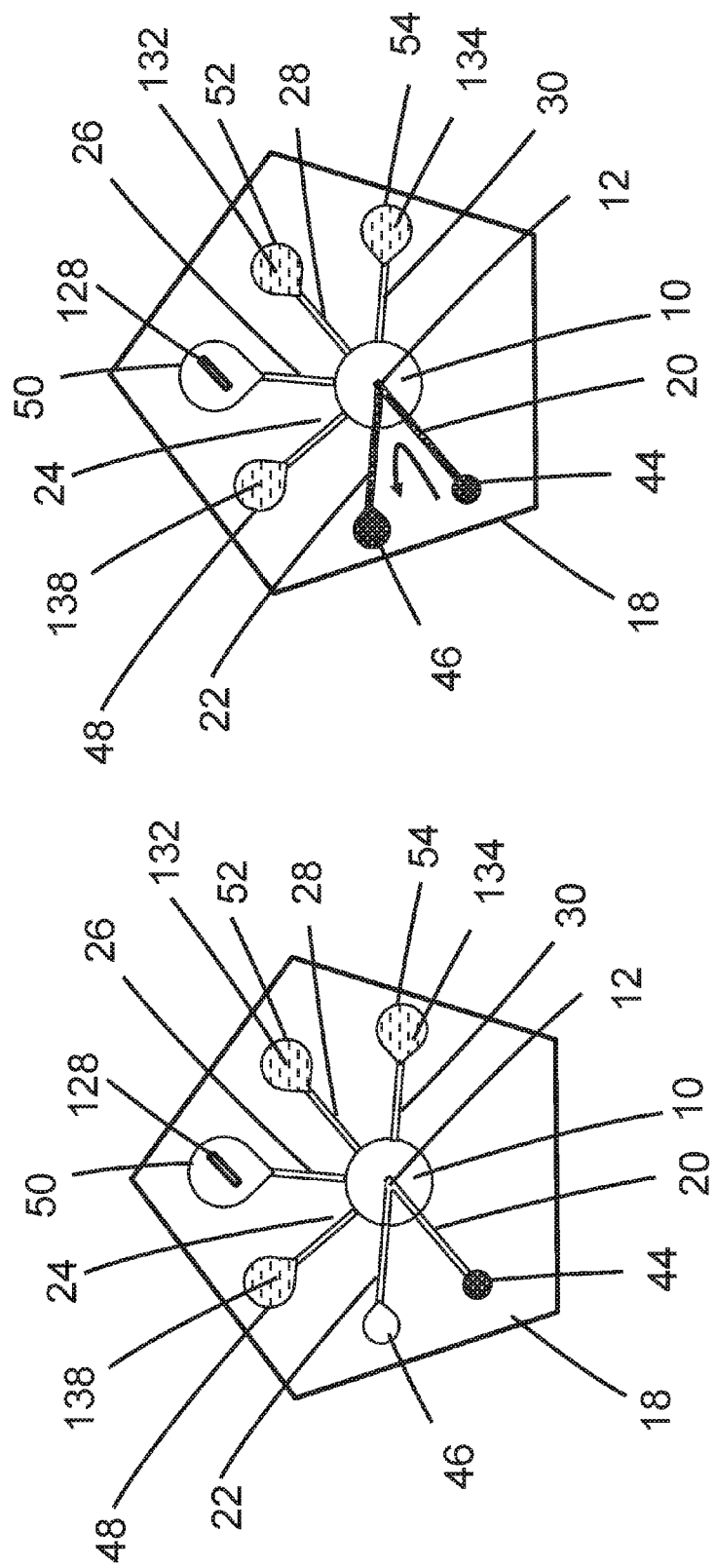

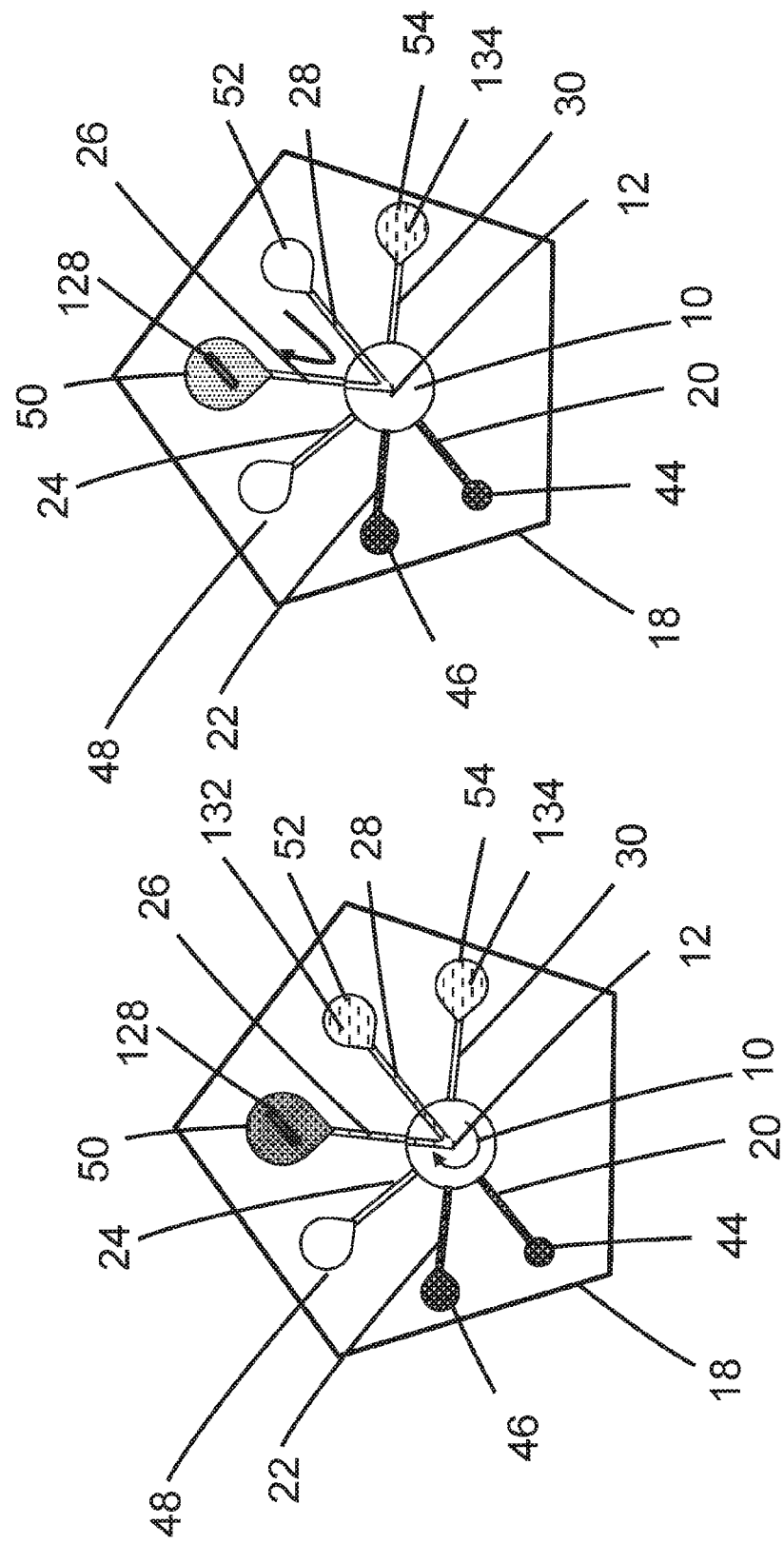

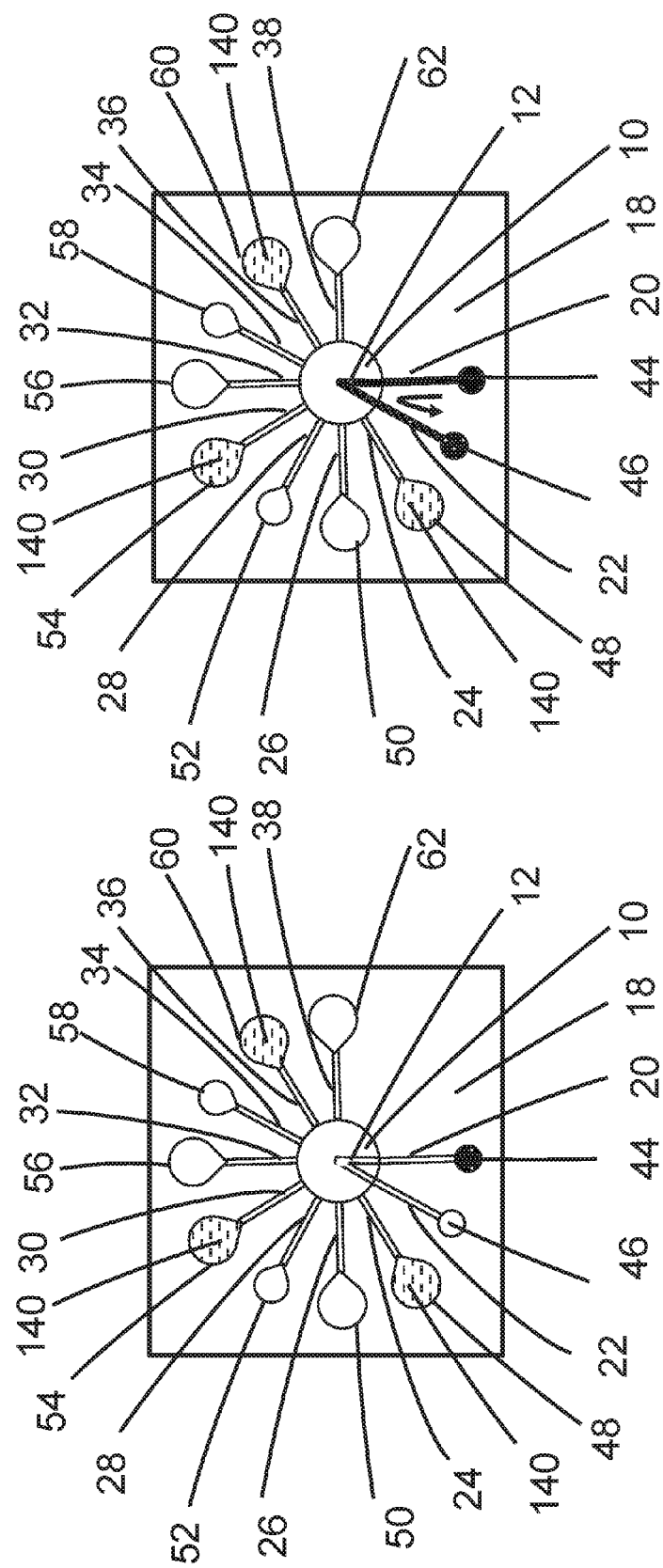

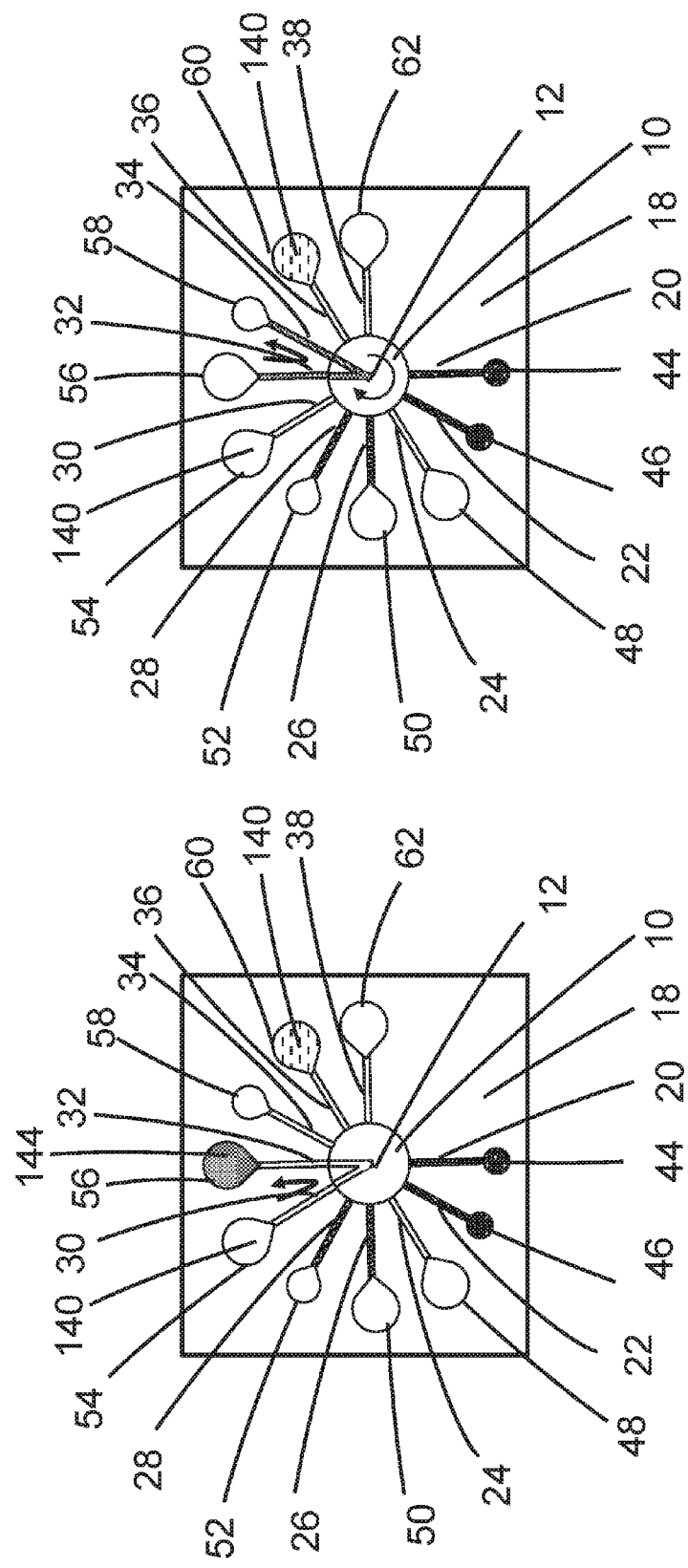

MICROFLUIDIC DEVICE FOR SERIAL FLUIDIC OPERATIONS

RELATED APPLICATION DATA

This application is a divisional application of U.S. Nonprovisional application Ser. No. 13/963,215 filed on Aug. 9, 2013, the contents of which is incorporated here by reference.

TECHNICAL FIELD

This invention relates to apparatuses for metering a volume of liquid. In particular, the invention relates to a microfluidic device that can accurately meter a small volume of fluid, and perform a series of fluidic operations on the metered sample.

BACKGROUND ART

The known art describes microfluidic metering apparatuses that use a linear, straight through metering channel within a rotating valve to meter a small volume of fluid. Only two fluidic conduits can be connected via the linear, straight through internal channel in the rotating valve in the prior art. The known art is limited in operational functionality, as it can only transfer the fluid contents of a first fluidic chamber, via the linear metering channel in the rotating valve, to a second fluidic chamber that is directly opposite the first chamber. It may be desirable, however, to transfer fluid contents as between more than two fluidic chambers, which generally cannot be done in conventional systems.

Patents Berndtsson et al. WO98/22797 (published May 18, 1998), Berndtsson WO99/01742 (published Jan. 14, 1999), and related patent applications Rodriguez et al. WO02/089760 A1 (published Nov. 14, 2002), Larsen et al. WO03/104770 A2 (published Dec. 18, 2003), Larsen et al. WO03/104771 A1 (published Dec. 18, 2003), and Larsen WO03/104772 A1 (published Dec. 18, 2003), all disclose conventional microfluidic metering devices. As being representative of such devices, FIG. 1A depicts such a device including a rotating valve 2 with a straight through channel 4 that is in communication with a first pair of opposing fluidic conduits 6 in a housing. The rotating valve is turned through 90 degrees, thus metering a small volume of fluid within the valve, and connecting a second pair of opposing fluidic conduits 8 as illustrated in FIG. 1B.

Berndtsson WO03/044488 A1 (published May 30, 2003) discloses a rotating valve with three straight through channels that all extend directly through the axial centre of the rotating valve. Each straight through channel is rotationally positioned at an angle with respect to the other two straight through channels within the valve. At any one time, two different straight through channels in the rotating valve can connect two different pairs of opposing fluidic conduits in a housing. The two different pairs of opposing fluidic conduits have no means of communicating with each other via the internal channels within the rotating valve. Mototsu EP1535667 A1 (published Jun. 1, 2005) discloses a rotating valve with a concavity formed in the axial direction of the rotating valve and in the outer wall of the rotating valve. The concavity is capable of metering a defined volume of fluid. The rotating valve can join two external conduits that are offset from each other along the axial direction of the rotating valve.

While the prior art discloses the use of linear, straight through channels that can meter a defined volume of fluid and connect two opposing fluidic conduits, they are limited in their ability to carry out a variety of different fluidic operations that require a plurality of fluidic conduits and/or chambers beyond just two, e.g. in conventional devices the entire fluidic contents of a first fluidic chamber can only be transferred to a second fluidic chamber that is directly opposite the first fluidic chamber via the straight through channel in the rotating valve. Other configurations that require transfers of fluid other than between two directly opposite fluidic chambers, including additional chambers beyond two, cannot be performed.

SUMMARY OF INVENTION

There exists a need in the art for a microfluidic device that can carry out a variety of different fluidic operations, in series, in a plurality of sequentially connectable conduits and/or chambers centered around a rotating valve, wherein the adjacent fluidic conduits and/or chambers are connected via an internal channel in said rotating valve.

The disclosed invention has the ability to put two fluidic conduits within a housing in communication with each other via an angled internal channel in a rotating valve. The same internal channel within the rotating valve can then be used to bring one of the said first two fluidic conduits into communication with a third fluidic conduit, then, optionally, to bring the third fluidic conduit into communication with a fourth fluidic conduit and so on. Therefore, in addition to metering, the invention has the ability to move the entire fluidic contents of one fluidic chamber to a second adjacent fluidic conduit and/or chamber, and then to a third fluidic conduit and/or chamber and, optionally, to a fourth fluidic conduit and/or chamber via the internal channel in the rotating valve in a series of fluidic operations, and so on.

The invention thus accurately meters a small volume of fluid in a channel contained within a rotating valve, which in turn is positioned within a housing. The housing contains a plurality of fluidic conduits centered around the rotating valve. Adjacent fluidic conduits are brought into communication with each other, sequentially, via the internal channel within the rotating valve. Fluidic operations including mixing, lysing, quenching, labeling, diluting, and others can be performed on the metered sample via the fluidic conduits and the internal channel in the rotating valve.

The disclosed invention thus connects two fluidic conduits in a housing, via an angled internal channel in the rotating valve, and then connects one of the said first two fluidic conduits to a third fluidic conduit via said single internal channel in the rotating valve. The disclosed invention can connect a first fluidic conduit and/or chamber and a second fluidic conduit and/or chamber in the housing together via an angled internal channel in the rotating valve. Rotating the valve then brings the second fluidic conduit and/or chamber into communication with a third fluidic conduit and/or chamber via the said internal channel in the rotating valve. The rotating valve can be rotated further to bring the third fluidic conduit and/or chamber into communication with a fourth fluidic conduit and/or chamber via the said internal channel in the rotating valve, and so on.

The basic concept of the invention is a fluidic device for metering a sample of fluid and carrying out fluidic operations on the metered sample including:

A housing with a number "n" of integrated microfluidic conduits and/or chambers, wherein n is at least three;

A rotating valve with at least one internal channel wherein the entrance port and exit port are greater than or equal to 10 degrees and less than or equal to 60 degrees angularly separated;

Whereby the rotating valve can be positioned to connect two sequentially adjacent fluidic conduits in the housing together via the at least one internal channel in the rotating valve;

Whereby, upon rotating the rotating valve, the next two sequentially adjacent fluidic conduits in the housing can be brought into communication via the internal channel in the rotating valve; and Where n may be a number between 5 and 36.

By rotating the rotating valve, sequentially connectable fluidic conduits and/or chambers can be brought into communication with each other via the internal channel in the rotating valve. For example, the rotating valve can be positioned to connect a first fluidic conduit and/or chamber and a second fluidic conduit and/or chamber in the housing together via the internal channel in the rotating valve. The rotating valve can then be rotated so that the second fluidic conduit and/or chamber can be brought into communication with a third fluidic conduit and/or chamber in the housing via the internal channel within the rotating valve, and so on for the n fluidic conduits in the housing.

A plurality of fluidic operations can be performed, in series or in parallel, on fluids contained within separate, preferably adjacent, fluidic conduits and/or chambers in the housing. The fluidic operations may include, but are not limited to, any combination of metering, re-metering, mixing, labelling, incubating, lysing, quenching, diluting, titrating, separating, and the transferring of fluid between adjacently connectable fluidic conduits and/or chambers.

The advantages of one or more embodiments of the invention include:

The ability to meter a defined volume of fluid within the at least one internal channel within the rotating valve;

Providing a flexible platform that allows a wide variety of fluidic operations to be carried out on a single fluidic device;

The ability to carry out a number of different fluidic operations in series;

Segregation of different fluids/reagents in the fluidic device;

The ability to transfer the entire fluid contents of one fluidic conduit and/or chamber to an adjacent fluidic conduit and/or chamber, then a further adjacent fluidic conduit and/or chamber and so on;

A reduction in the amount of reagents required to carry out complex chemical and/or biochemical reactions;

Ease of use by a semi-skilled operator;

Means of sealing the device so that biological samples and/or chemicals are enclosed within the device and do not provide a contamination hazard;

Fully integrated fluidic control mechanisms;

Methods of self-calibration to confirm the actual volume of fluid metered in the internal channel in the rotating valve;

Methods of carrying out fluidic operations in series on two or more different samples in parallel using a single device;

Means of integrating sensors into the fluidic conduits to analyze the fluids in the microfluidic device.

BRIEF DESCRIPTION OF DRAWINGS

In the annexed drawings, like references indicate like parts or features:

FIGS. 1A-B show conventional devices for fluid metering in a rotating valve.

FIGS. 2A-C show three embodiments of an exemplary internal channel within the rotating valve in relation to the invention.

FIG. 3A-E show six exemplary embodiments of the invention each having a different conduit configuration.

FIGS. 4A-C each show a plan view and two cross-sections of an exemplary embodiment of the invention demonstrating integrated fluid control with respect to the invention.

FIGS. 5A-B each show a plan view and a cross-section of an exemplary embodiment of fluidic chamber geometries within a housing with respect to the invention.

FIGS. 6A-J each show a plan view and two cross-section views of a further exemplary embodiment of integrated fluid control with respect to the invention.

FIGS. 7A-C each show a plan view and two cross-section views of yet a further exemplary embodiment of integrated fluid control with respect to the invention.

FIGS. 8A-E depict an example of how optical measurements may be made in the fluidic device according to an exemplary embodiment of the invention.

FIG. 9A-C depict an example of how a magnetic flea may be optimized for lysing and/or mixing fluidic operations according to an exemplary embodiment of the invention.

FIGS. 10A-J depict how the invention is used in accordance with the described Example 1.

FIGS. 11A-H depict how the invention is used in accordance with the described Example 2.

FIGS. 12A-J depict how the invention is used in accordance with the described Example 3.

DESCRIPTION OF REFERENCE NUMERALS

Figure 3A:
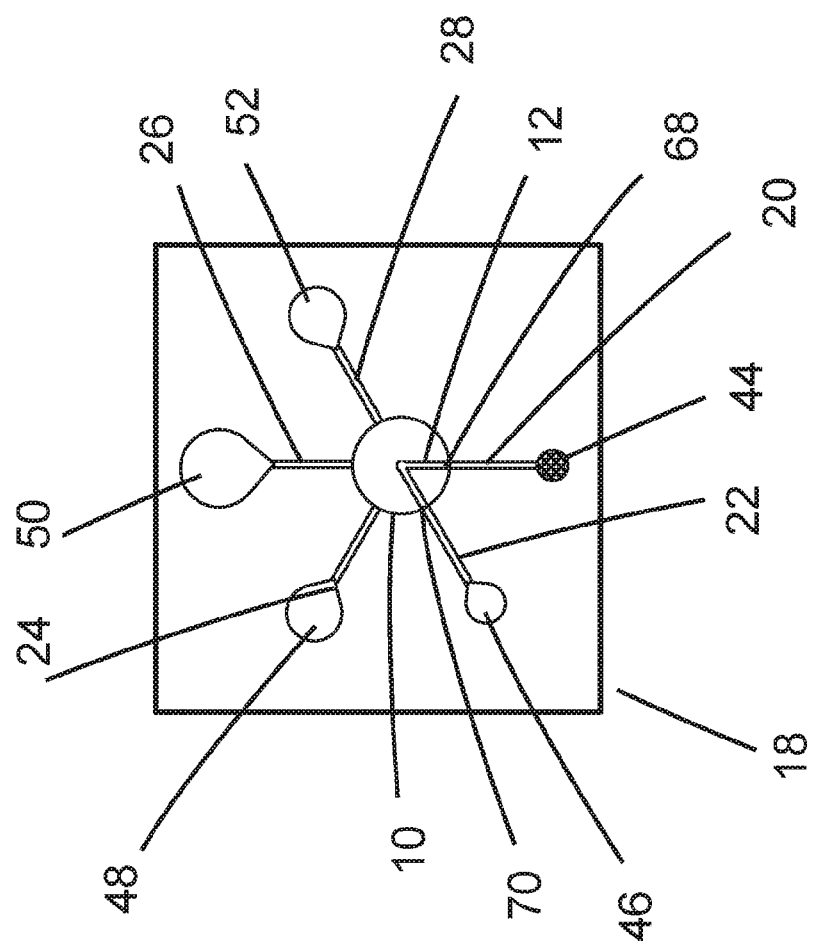

2 Prior art rotating valve
4 Straight through channel
6 First pair of opposing fluidic conduits
8 Second pair of opposing fluidic conduits
10 Rotating valve
12 'V' shaped internal channel
14 'U' shaped internal channel
16 'L' shaped internal channel
18 Housing
20 First fluidic conduit
22 Second fluidic conduit
24 Third fluidic conduit
26 Fourth fluidic conduit
28 Fifth fluidic conduit
30 Sixth fluidic conduit
32 Seventh fluidic conduit
34 Eighth fluidic conduit
36 Ninth fluidic conduit
38 Tenth fluidic conduit
40 Eleventh fluidic conduit
42 Twelfth fluidic conduit
44 First fluidic chamber
46 Second fluidic chamber
48 Third fluidic chamber
50 Fourth fluidic chamber
52 Fifth fluidic chamber
54 Sixth fluidic chamber
56 Seventh fluidic chamber
58 Eighth fluidic chamber 60 Ninth fluidic chamber
62 Tenth fluidic chamber
64 Eleventh fluidic chamber
66 Twelfth fluidic chamber
68 Input port
70 Output port
72 Second V shaped internal channel
74 Defined volume of fluid
76 Defined volume of gas
78 First moveable piston
80 Second moveable piston
82 Third moveable piston
84 Fourth moveable piston
86 Metered volume of fluid
88 First integral air vent
90 Second integral air vent
92 Second defined volume of fluid
94 Third defined volume of fluid
96 Fourth defined volume of fluid
98 Fifth defined volume of fluid
100 Second defined volume of gas
102 Third defined volume of gas
104 Sensor
106 Gas communication conduit
108 Piston housing
110 Stepping motor
112 First light source
114 Second light source
116 Third light source
118 Fourth light source
120 First photodetector
122 Second photodetector
124 Third photodetector
126 Fourth photodetector
128 Magnetic flea
130 Volume of fluid with an aspect ratio of 0.38
132 Predefined volume of lysis reagent
134 Predefined volume of quench reagent
136 First metered volume of blood
138 Predefined volume of a fluorescent label reagent
140 64.5 ul of a diluting reagent
142 1:21.5 diluted blood sample
144 1:462.25 diluted blood sample
146 1:9,938 diluted blood
148 Fluidic cartridge
150 Predefined volume of diluting reagent
152 Second rotating valve
154 Thirteenth fluidic conduit
156 Fourteenth fluidic conduit
158 Fifteenth fluidic conduit
160 Sixteenth fluidic conduit
162 Thirteenth fluidic chamber
164 First microfluidic cell counter
166 Second microfluidic cell counter
168 Haemoglobin measurement chamber
170 Waste chamber
172 Defined volume of carboxylic acid solution
174 Defined volume of activating agent
176 Defined volume of n-hydroxysuccinimide
178 Defined volume of pH 8 buffer
180 Defined volume of an amine solution

DETAILED DESCRIPTION OF INVENTION

The invention is a fluidic device that comprises a housing with a rotating valve. The housing contains a plurality of fluidic conduits that extend towards the rotating valve. Each individual fluidic conduit may, optionally, also be in communication with a fluidic chamber located within the housing. The fluidic conduits in the housing are centered around the rotating valve with a defined angular separation. An internal channel within the rotating valve can be positioned to connect any two sequentially adjacent fluidic conduits in the housing together.

An aspect of the invention is an integrated microfluidic device for carrying out a series of fluidic operations. Generally, the integrated microfluidic device includes a housing including a plurality of n microfluidic conduits, wherein n is at least three, and a rotating valve having an internal channel with an entrance port and an exit port that are angularly separated. The rotating valve is positionable in a first position to connect two of the n fluidic conduits via the internal channel, and upon rotating the valve to a second position, two of the n fluidic conduits, including at least one fluidic conduit different from the fluidic conduits connected in the first position, are connected by the internal channel. The device further may include one or more fluidic chambers in fluid communication with respective fluidic conduits. Fluid contained in one fluidic chamber is transferrable by application of positive or negative gas pressure through associated fluidic conduits into another fluidic chamber via the internal channel. As described in more detail below, the device may be utilized to perform a variety of fluidic operations.

The channel within the rotating valve may be any shape or length, provided that the angle between the input and output ports can connect any two sequentially adjacent fluidic conduits in the housing together. Preferably, the internal channel in the rotating valve will have input and output ports that have the same defined angular separation as the surrounding fluidic conduits. Preferably, the input and output ports of the internal channel will be greater than or equal to 10 degrees and less than or equal to 60 degrees apart. Preferably, the internal channel within the rotating valve will be circular, rectilinear, or square in cross-section and be substantially 'V', 'U' or 'L' shaped. One particularly suitable embodiment for a variety of applications has a channel within the rotating valve being substantially 'V' shaped with a circular cross-section.

FIG. 2A teaches one embodiment of the rotating valve 10 with a substantially 'V' shaped internal channel 12.

FIG. 2B teaches a second embodiment of the rotating valve 10 with a substantially 'U' shaped internal channel 14.

FIG. 2C shows a third embodiment of the rotating valve 10 with a substantially 'L' shaped internal channel 16.

The internal channel in the rotating valve provides two main advantages:
  To provide a means of putting two, preferably sequentially adjacent, fluidic conduits in the housing in communication with each other.
  To enable accurate metering of small volumes of fluid where the metered volume of fluid is substantially equivalent to the volume of the internal channel.

For example, the channel within the rotating valve will have a volume of 1-50 ul, or a volume of 1-20 ul, or a volume of 1-5 ul. Optionally, the volume of the internal channel within the rotating valve may be less than 1 ul or more than 50 ul.

The housing contains a plurality of fluidic conduits that extend towards the rotating valve. Each individual fluidic conduit may, optionally, also be in communication with a fluidic chamber located within the housing. The fluidic conduits in the housing are centered round the rotating valve with a defined angular separation. A plurality of fluidic operations can be carried out between the plurality of separate, fluidic conduits and/or chambers in the housing via the internal channel in the rotating valve. The fluidic operations may be carried out between sequentially adjacent fluidic conduits and/or chambers. The fluidic conduits in the housing may be substantially circular, rectilinear, or square in cross-section.

In exemplary embodiments, at least three fluidic operations can be carried out in series between at least three separate, potentially adjacent fluidic conduits and/or chambers in the housing. The fluidic operations may include, but are not limited to, any combination of metering, re-metering, mixing, labelling, staining, incubating, lysing, quenching, diluting, titrating, separating, holding a metered volume of fluid within the internal channel in the rotating valve, and/or the transferring of fluid between adjacent external chambers. Such fluidic operations may be carried out in series.

Metering is defined as the ability to accurately measure, and then isolate, a small volume of fluid from a fluid sample.

Labelling is defined as the process of adding a marker, such as a fluorescent or radioactive marker, to e.g. a cell, bead, or other biological entity.

Incubating is defined as providing favourable conditions for specific processes, e.g. fluorescent labelling of blood cells, to take place.

Lysing is defined as the destruction or dissolution of cells, such as by chemical and/or mechanical means.

Quenching is defined as the halting, stopping or significant reduction in the rate of lysing, such as by chemical means.

Titrating is defined as the process carried out to ascertain the concentration of a given analyte (such as with some indicator fluid) by adding a titrant solution of known concentration in small volumes, and measuring the volume of titrant required to convert the analyte (or indicator) to a different form.

Separating is defined as sorting or isolating different components, or elements, within a fluid sample. This may be achieved using magnetic beads and magnets, covalent attachment, and the like.

Metering is achieved in this invention using the internal channel within the rotating valve. The metered volume of fluid is substantially equivalent to the volume of the internal channel within the rotating valve. Using one method, fluid can be metered by placing, for example, a first fluidic conduit and a second fluidic conduit in communication with each other via the internal channel in the rotating valve. Fluid introduced to the first fluidic conduit fills the first fluidic conduit, the internal channel in the rotating valve and at least partially fills the second fluidic conduit. Rotating the rotating valve isolates the internal channel in the rotating valve from the first fluidic conduit and the second fluidic conduit and thus contains a metered volume of fluid. Alternatively, the second fluidic conduit could contain a fluid repellent coating, such as for example, a hydrophobic coating to repel an aqueous based fluid. In this instance, fluid introduced to the first fluidic conduit would only fill the first fluidic conduit and the internal channel in the rotating valve. The second fluidic conduit simply acts as an air vent. The dimensions of the second fluidic conduit could be configured to act as a capillary stop. Rotating the rotating valve isolates the internal channel in the rotating valve from the first fluidic conduit, and thus contains a metered volume of fluid, with no overflow of fluid into the second fluidic conduit.

FIG. 3A shows one embodiment of the invention in which there are five fluidic conduits 20, 22, 24, 26, and 28 in the housing 18, centered around a rotating valve 10. The fluidic conduits are angularly separated by 60 degrees. The first fluidic conduit 20 is in communication with a first fluidic chamber 44. The second fluidic conduit 22 is in communication with a second fluidic chamber 46. The third fluidic conduit 24 is in communication with a third fluidic chamber 48. The fourth fluidic conduit 26 is in communication with a fourth fluidic chamber 50, and the fifth fluidic conduit 28 is in communication with a fifth fluidic chamber 52. The rotating valve has a substantially 'V' shaped internal channel 12 with the input port 68 and output port 70 being sixty degrees apart. The rotating valve can be rotated to sequentially connect any two adjacent fluidic conduits in the housing via the internal channel in the rotating valve.

Figure 3B:
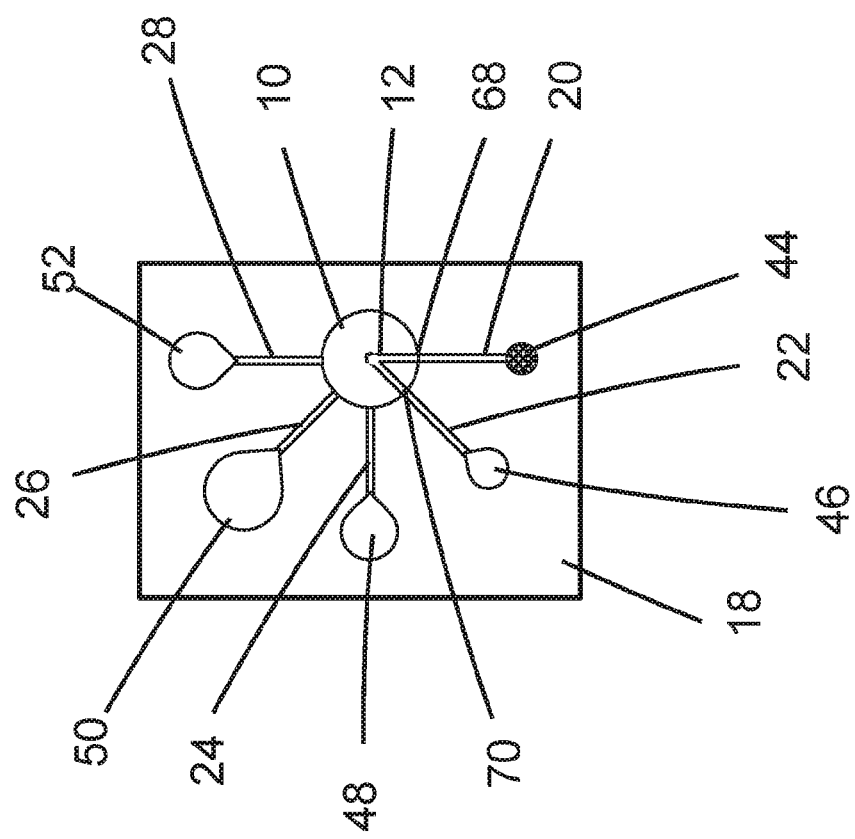

FIG. 3B shows one embodiment of the invention in which there are five fluidic conduits 20, 22, 24, 26, 28 in the housing 18, centered around a rotating valve 10, angularly separated by 45 degrees. The first fluidic conduit 20 is in communication with a first fluidic chamber 44. The second fluidic conduit 22 is in communication with a second fluidic chamber 46. The third fluidic conduit 24 is in communication with a third fluidic chamber 48. The fourth fluidic conduit 26 is in communication with a fourth fluidic chamber 50, and the fifth fluidic conduit 28 is in communication with a fifth fluidic chamber 52. The rotating valve has a substantially 'V' shaped internal channel 12 with the input port 68 and output port 70 being forty-five degrees apart. The internal channel, located within the rotating valve, can be rotated to connect any two sequentially adjacent fluidic conduits in the housing.

Figure 3C:
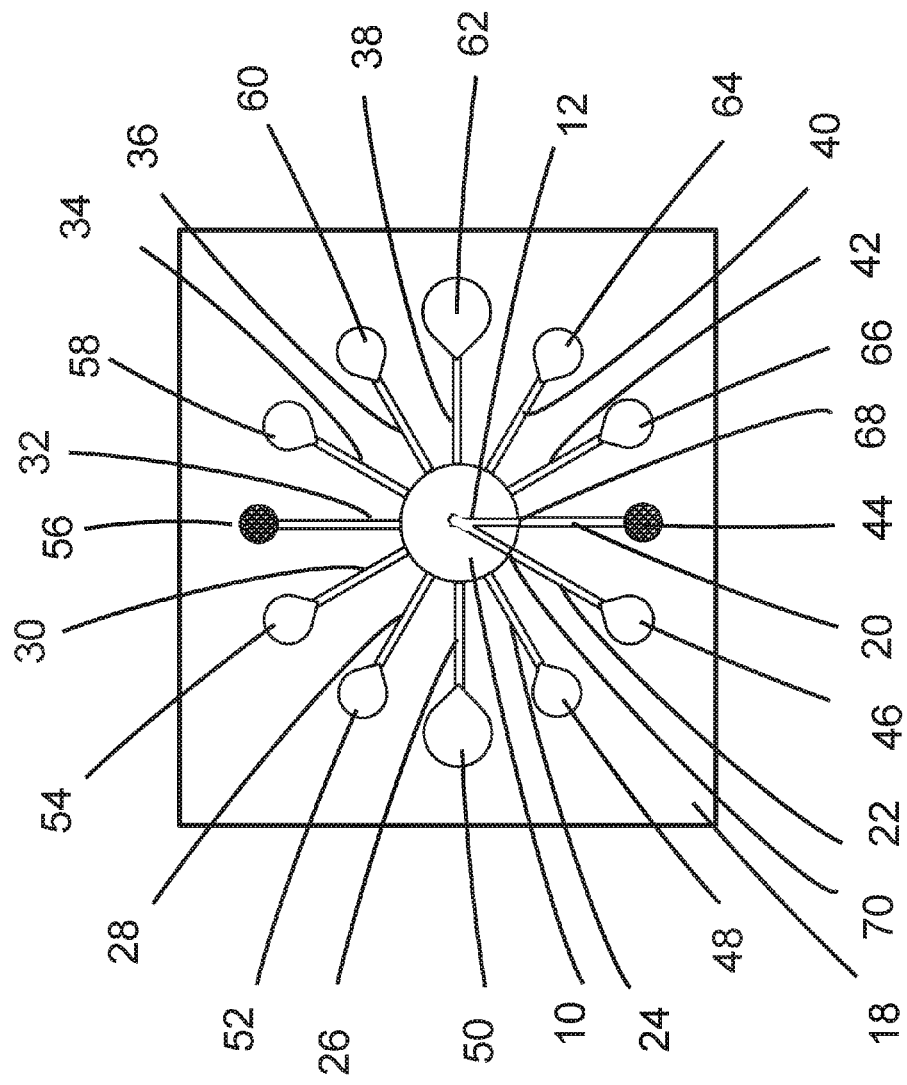

FIG. 3C shows one embodiment of the invention in which there are twelve fluidic conduits 20, 22, 24, 26, 28, 30, 32, 34, 36, 38, 40, 42 in the housing 18, centered round a rotating valve 10, angularly separated by 30 degrees. The first fluidic conduit 20 in is communication with a first fluidic chamber 44. The second fluidic conduit 22 is in communication with a second fluidic chamber 46. A third fluidic conduit 24 is in communication with a third fluidic chamber 48. A fourth fluidic conduit 26 is in communication with a fourth fluidic chamber 50. A fifth fluidic conduit 28 is in communication with a fifth fluidic chamber 52. A sixth fluidic conduit 30 is in communication with a sixth fluidic chamber 54. A seventh fluidic conduit 32 is in communication with a seventh fluidic chamber 56. An eighth fluidic conduit 34 is in communication with an eighth fluidic chamber 58. A ninth fluidic conduit 34 is in communication with a ninth fluidic chamber 60. A tenth fluidic conduit 38 is in communication with a tenth fluidic chamber 62. An eleventh fluidic conduit 40 is in communication with an eleventh fluidic chamber 64, and a twelfth fluidic conduit 42 is in communication with a twelfth fluidic chamber 66. The rotating valve has a substantially 'V' shaped internal channel 12 with the input port 68 and output port 70 being thirty degrees apart. The rotating valve can be rotated to sequentially connect any two adjacent fluidic conduits in the housing via the internal channel in the rotating valve.

FIG. 3D teaches one embodiment of the invention in which there are twelve fluidic conduits 20, 22, 24, 26, 28, 30, 32, 34, 36, 38, 40, 42 in a housing 18 centered round a rotating valve 10, with adjacent conduits angularly separated by 30 degrees. The first fluidic conduit 20 in is communication with a first fluidic chamber 44. The second fluidic conduit 22 is in communication with a second fluidic chamber 46. A third fluidic conduit 24 is in communication with a third fluidic chamber 48. A fourth fluidic conduit 26 is in communication with a fourth fluidic chamber 50. A fifth fluidic conduit 28 is in communication with a fifth fluidic chamber 52. A sixth fluidic conduit 30 is in communication with a sixth fluidic chamber 54. A seventh fluidic conduit 32 is in communication with a seventh fluidic chamber 56. An eighth fluidic conduit 34 is in communication with an eighth fluidic chamber 58. A ninth fluidic conduit 34 is in communication with a ninth fluidic chamber 60. A tenth fluidic conduit 38 is in communication with a tenth fluidic chamber 62. An eleventh fluidic conduit 40 is in communication with an eleventh fluidic chamber 64, and a twelfth fluidic conduit 42 is in communication with a twelfth fluidic chamber 66. The rotating valve has two substantially 'V' shaped internal fluidic channels 12,72 not in communication with each other, that are individually and simultaneously in communication with different adjacent fluidic conduits in the housing. The first substantially 'V' shaped internal fluidic channel 12 is in communication with the first fluidic conduit 20 and second fluidic conduit 22. The second substantially 'V' shaped internal fluidic channel 72 is in communication with the seventh fluidic conduit 32 and eighth fluidic conduit 34. This embodiment enables two fluidic samples to be input, metered and simultaneously subjected to a series of fluidic operations on the same device. Optionally, the two internal channels within the rotating valve may be configured such that only one internal channel is in communication with a pair of adjacent fluidic conduits within the housing at any one time. This embodiment also could be configured to carry out any given or particular fluidic process in triplicate, or quadruplicate, or to perform at least one sample measurement and a control measurement.

Figure 3E:
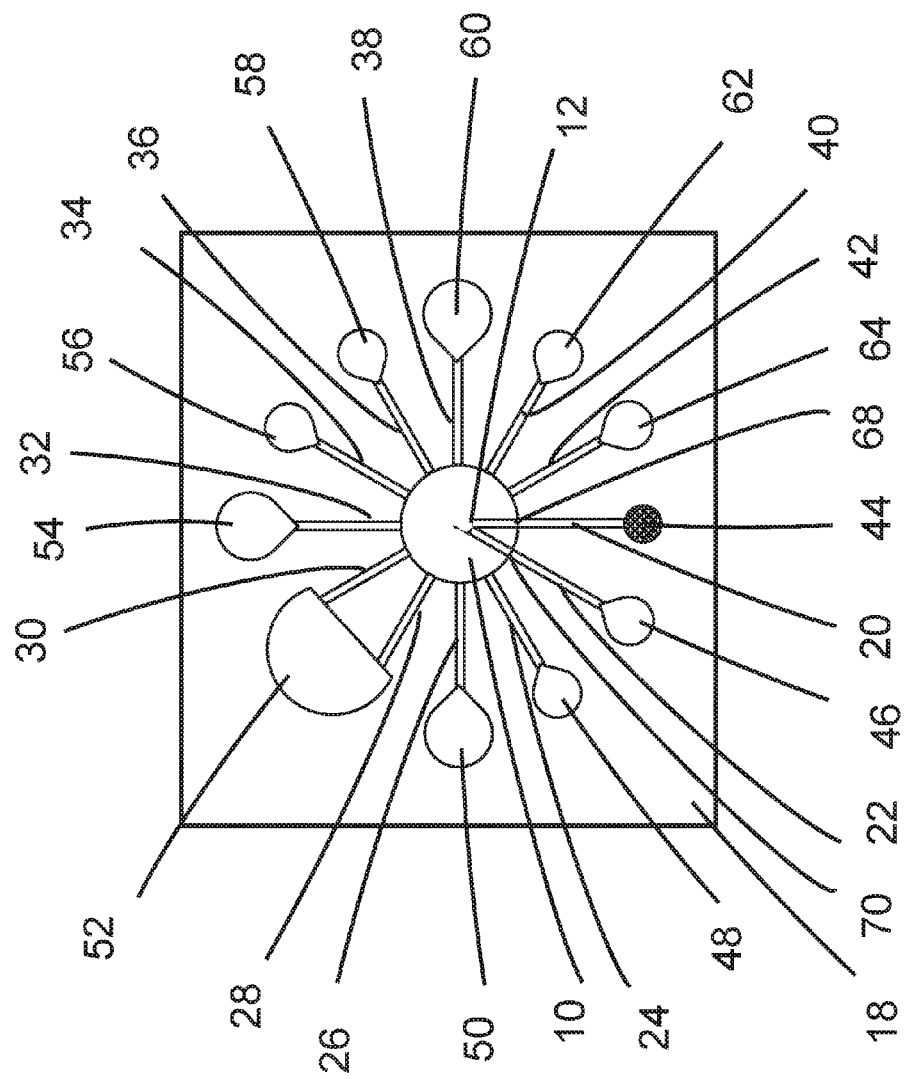

FIG. 3E illustrates a further embodiment of the invention with twelve fluidic conduits 20, 22, 24, 26, 28, 30, 32, 34, 36, 38, 40, 42 contained within a housing 18, centered round a rotating valve, with adjacent fluidic conduits angularly separated by 30 degrees. The first fluidic conduit 20 in is communication with a first fluidic chamber 44. The second fluidic conduit 22 is in communication with a second fluidic chamber 46. A third fluidic conduit 24 is in communication with a third fluidic chamber 48. A fourth fluidic conduit 26 is in communication with a fourth fluidic chamber 50. The fifth fluidic conduit 28 and the sixth fluidic conduit 30 are both in communication with the fifth fluidic chamber 52. A seventh fluidic conduit 32 is in communication with a sixth fluidic chamber 54. An eighth fluidic conduit 34 is in communication with a seventh fluidic chamber 56. A ninth fluidic conduit 34 is in communication with an eighth fluidic chamber 58. A tenth fluidic conduit 38 is in communication with a ninth fluidic chamber 60. An eleventh fluidic conduit 40 is in communication with a tenth fluidic chamber 62, and a twelfth fluidic conduit 42 is in communication with an eleventh fluidic chamber 64. The rotating valve 10 has a single substantially 'V' shaped internal channel 12 which can be positioned to sequentially connect any two adjacent fluidic conduits in the housing.

The internal channel in the rotating valve may substantially extend along the same longitudinal axis as the conduit in the housing with which it is in communication. The cross-section of the internal channel in the rotating valve may be the same as or different from the conduit in the housing with which it is in communication. The cross-section of the internal channel in the rotating valve may match the cross-section of the conduit with which it is in communication.

The volumes of the fluidic chambers can be designed to hold a desired volume of fluid. For example, the volume of the fluidic chambers can be designed to be as small as 10 ul or as large as 10 ml. In exemplary embodiments, the volume of a fluidic chamber will be between 20 ul and 3 ml, or the volume of a fluidic chamber will be between 20 ul and 500 ul. The different fluidic chambers in a single microfluidic device do not need to be the same volume, and the volumetric design of each fluidic chamber can be optimized for any given or particular application.

The microfluidic device may be fabricated from any suitable material that is compatible with the operational fluids. Compatibility implies that the fluid does not substantially adhere or non-specifically bind to the surface of the material, and that the material is not damaged or dissolved by the fluid. Several engineering polymers may be used to fabricate the invention and include, but are not limited to, PMMA (Poly(methyl methacrylate)), PET (Polyethylene terephthalate), Polypropylene, PTFE (Polytetrafluoroethylene), and Nylon. The invention could be fabricated using any suitable manufacturing process, including injection molding, laser cutting, drilling and/or milling. Alternatively, the fluidic conduits in the housing may be patterned in resist using soft lithography techniques and processed using e.g. wet etching and/or dry etching techniques, and the like.

The input and metered fluid could be chemical, e.g. test reagents, reducing agents, functionalized beads etc., biological, e.g. blood, urine, saliva, DNA etc., environmental, e.g. water samples, ice core samples etc, or for monitoring food quality and/or safety, e.g. milk, water etc. It will be apparent that the invention can be used to carry out titrations, binding reactions, chemical functionalization processes, fluorescent labeling processes, fluid sample preparation processes, peptide synthesis processes, serial dilutions, and any other suitable processes. It will be further apparent that the microfluidic device described could form part of a point-of-care diagnostics system.

Fluids can be moved around the microfluidic device using capillary forces, and/or positive and/or negative gas pressure, and/or positive and/or negative displacement pressure. It will be further apparent that the fluid control mechanisms could be external to the microfluidic housing, or could be integrated into the microfluidic device housing. In one aspect of the invention, specific individual fluidic chambers within the microfluidic device could each be connected to an external gas supply to pump the fluids between chambers.

FIGS. 4A-C teach one embodiment in which the fluid is pumped between adjacent fluidic conduits using integrated, moveable pistons. A housing 18 contains a rotating valve 10 with a substantially 'V' shaped internal channel 12. Five fluidic conduits are angularly separated by 30 degrees around one half of the rotating valve. The first fluidic conduit 20 in is communication with a first fluidic chamber 44, which is open to ambient surroundings. The second fluidic conduit 22 is in communication with a second fluidic chamber 46 which is open to ambient surroundings. A third fluidic conduit 24 is in communication with a third fluidic chamber 48 which is sealed using a first moveable piston 78. A fourth fluidic conduit 26 is in communication with a fourth fluidic chamber 50 which is sealed using a second moveable piston 80. A fifth fluidic conduit 28 is in communication with a fifth fluidic chamber 52 which is sealed using a third moveable piston 82. In this particular embodiment, the third fluidic chamber 48 is pre-filled with a defined volume of fluid 74. In FIG. 4A, the first moveable piston 78 seals the defined volume fluid 74 within the third fluidic chamber 48, and is held in a first position at a height "h" above the base of the third fluidic chamber. It follows that the sealed third fluidic chamber contains a pre-defined volume of fluid 74 with a defined volume of gas 76 separating the first moveable piston 78 from the pre-loaded defined volume of fluid. The fourth fluidic chamber 50, which is empty, is sealed with a second moveable piston 80 held at a second position at a height h=0 above the base of the fourth fluidic chamber. In FIG. 4B, the rotating valve 10 is rotationally positioned to join the third fluidic conduit 24 and the fourth fluidic conduit 26 together. In this embodiment, the third fluidic chamber 48 and fourth fluidic chamber 50 are of equivalent volume. As the first moveable piston 78 is depressed, the defined volume of fluid 74 is forced through the third fluidic conduit 24, through the internal channel 12 in the rotating valve, and into the fourth fluidic conduit 26 and then subsequently into the fourth fluidic chamber 50. As a consequence, the second moveable piston 80 is forced vertically to a height equivalent to the height that the first moveable piston 78 is depressed. Once the first moveable piston 78 has been depressed to a height h=0 above the base of the third fluidic chamber 48, all of the fluid from the third fluidic chamber has been forced through the internal channel 12 in the rotating valve 10 and into the fourth fluidic chamber 50 as shown in FIG. 4C. The final position of the second moveable piston 80 is at a height h above the base of the fourth fluidic chamber 50. The fourth fluidic chamber now contains the defined volume of fluid 74.

The defined volume of gas 76 must be sufficient to force the defined volume of fluid 74 through the third fluidic conduit 24, through the internal channel 12 in the rotating valve 10, through the fourth fluidic conduit 26 and into the fourth fluidic chamber 50.

The fifth fluidic chamber 52, which is empty in this example, is sealed with a third moveable piston 82 held at a height h=0 above the base of the fifth fluidic chamber. The total volume of the fifth fluidic chamber is equivalent to the total volume of the fourth fluidic chamber. The rotating valve 10 can be rotated through 45 degrees in the clockwise direction, bringing the fourth fluidic conduit 26 and the fifth fluidic conduit 28 into communication via the internal channel 12 in the rotating valve 10, and the same process is repeated to continue moving fluids from e.g. the fourth fluidic chamber 50, through the fourth fluidic conduit 26, through the internal channel 12 in the rotating valve, through the fifth fluidic conduit 28 and into the fifth fluidic chamber 52 by depressing the second moveable piston 80. The third moveable piston 82 will be displaced vertically upwards by a height equivalent to the height that the second moveable piston 80 is depressed.

Optionally, the internal channel in the rotating valve may contain a metered volume of fluid at the start of the described fluid moving operation. A fluid may be metered by positioning the rotating valve such that the internal channel within the rotating valve is in communication with both the first fluidic conduit and the second fluidic conduit. As a consequence of inputting an input fluid through the first fluidic conduit, into the internal channel in the rotating valve, and at least partially into the second fluidic conduit, and then, with reference to the embodiment depicted in FIGS. 4A-C, rotating the rotating valve 90 degrees in the clockwise direction, a metered volume of input fluid is contained within the internal channel. The internal channel in the rotating valve further brings the third fluidic conduit and the fourth fluidic conduit into communication. In this instance, when the first moveable piston is depressed, the defined volume of fluid and the defined volume of gas in the third fluidic chamber flush the metered volume of fluid in the internal channel in the rotating valve into the fourth fluidic conduit, and then into the fourth fluidic chamber.

It will be apparent to one skilled in the art that not all of the fluidic chambers need to be of the same volume, and that the geometries of the chambers and/or pistons can be designed as to best accommodate (a) the volume fluid that a chamber is pre-loaded with and/or (b) the volume of fluid that needs to be moved between chambers and/or (c) the maximum volume of fluid that a particular chamber will have to hold during operation.

It will be further apparent to one skilled in the art that different fluidic chambers can be designed as to best accommodate their purpose, e.g. as taught in FIG. 5A for specifically dispensing fluid or in FIG. 5B for specifically receiving fluid. If, for example, third fluidic chamber 48 is specifically designed only to dispense fluid, then the base of the third fluidic chamber can be designed to facilitate the dispensing of fluid, for example by curving the base of the third fluidic chamber 48 so that fluid naturally comes into communication with a third fluidic conduit 24 positioned at the base of the dispensing third fluidic chamber as shown in FIG. 5A. Alternatively, for chambers that only receive fluid, it is possible to design the microfluidic device such that, for example, the fourth fluidic conduit 26 that is in communication with the internal channel 12 within the rotating valve 10 further communicates with the top of the receiving fourth fluidic chamber 50 as taught in FIG. 5B.

FIGS. 6A-J teach one embodiment in which the fluid is pumped between different fluidic conduits, via the internal channel in the rotating valve, using integrated, moveable pistons, where any excess gas within the device can be vented. The housing contains a rotating valve with a substantially 'V' shaped internal channel and six fluidic conduits angularly separated by 45 degrees centered round the rotating valve (FIG. 6A). The first fluidic conduit 20 in is communication with a first fluidic chamber 44, which is open to ambient surroundings. The second fluidic conduit 22 is in communication with a second fluidic chamber 46 which is open to ambient surroundings. A third fluidic conduit 24 is in communication with a third fluidic chamber 48 which is closed using a first moveable piston 78. A fourth fluidic conduit 26 is in communication with a fourth fluidic chamber 50 which is closed using a second moveable piston 80. A fifth fluidic conduit 28 is in communication with a fifth fluidic chamber 52 which is closed using a third moveable piston 82. A sixth fluidic conduit 30 is in communication with a sixth fluidic chamber 54 which is closed using a fourth moveable piston 84. The fluid receiving fourth fluidic chamber 50 is in communication with a first integral air vent 88, and the fifth fluidic chamber 52 in communication with a second integral air vent 90. In this illustrative embodiment, the third fluidic chamber 48 is pre-filled with a defined volume of fluid 74. The first moveable piston 78 encloses the defined volume of fluid within the third fluidic chamber 48, and is held in a first position a height "h" above the base of the third fluidic chamber. It follows that the enclosed third fluidic chamber contains a pre-defined volume of fluid 74, with a defined volume of gas 76 separating the first moveable piston from the pre-loaded defined volume of fluid. A fourth fluidic chamber 50, which is empty, is sealed with a second moveable piston 80 held at a second position a height "h" above the base of the fourth fluidic chamber. A first integral air vent 88 is in communication with the fourth fluidic chamber and the ambient surroundings. The rotating valve, which optionally contains a metered volume of fluid in the internal channel, is rotationally positioned to join the third fluidic conduit 24 and the fourth fluidic conduit together 26. As the first moveable piston 78 is depressed (FIG. 6B), the defined volume of fluid 74 is forced through the third fluidic conduit 24, through the internal channel 12 in the rotating valve 10, and into the fourth fluidic conduit 26 and into the fourth fluidic chamber 50. Once the first moveable piston 78 has been depressed to a height h=0 above the base of the chamber, (FIG. 6C), all of the defined volume of fluid 74 from the third fluidic chamber 48 has been forced through the third fluidic conduit 24, the internal channel 12 in the rotating valve 10, the fourth fluidic conduit 26 and into the fourth fluidic chamber 50. The defined volume of gas 76 must be sufficient to force the defined volume of fluid 74 through the third fluidic conduit, through the internal channel 12 in the rotating valve 10, through the fourth fluidic conduit 26 and into the fourth fluidic chamber 50. Any excess gas can be bubbled through the defined volume of fluid 74 in the fourth fluidic chamber 50 and vented through the first integral air vent 88. If the defined volume of gas and defined volume of fluid originally contained within the third fluidic chamber is greater than the total capacity of the fourth fluidic chamber, the first moveable piston can still be depressed to its full extent as all excess gas is vented through the first integral air vent, provided that the capacity of the fourth fluidic chamber is sufficient to hold the defined volume of fluid. This is advantageous as fine depression control of the first moveable piston is not required. The first integral air vent 88 preferably contains a fluid repellent coating and/or membrane to prevent the fluid pumped into the fourth fluidic chamber 50 from accidentally leaking out of the device.

The rotating valve is then rotated 45 degrees in the clockwise direction to bring the fourth fluidic conduit 26 into communication with the fifth fluidic conduit 28 (FIG. 6D). The third moveable piston 82 encloses a second defined volume of fluid 92 within the fourth fluidic chamber 48, and is held in a first position a height "h" above the base of the fourth fluidic chamber. The third fluidic chamber is in communication with a second integral air vent 90. It follows that the enclosed fourth fluidic chamber contains a pre-defined second volume of fluid 92, with a second defined volume of gas 100 separating the third moveable piston 82 from the pre-loaded second defined volume of fluid 92. The fourth fluidic chamber 50, already contains a defined volume of fluid 74. As the third moveable piston 82 is depressed, the second defined volume of fluid 92 is forced through the fifth fluidic conduit 28, through the internal channel 12 in the rotating valve 10, and into the fourth fluidic conduit 26 and into the fourth fluidic chamber 50 (FIG. 6E). Once the third moveable piston 82 has been depressed to a height h=0 above the base of the fifth fluidic chamber 52, all of the second defined volume of fluid 92 from the fifth fluidic chamber 52 has been forced through the fifth fluidic conduit 28, the internal channel 12 in the rotating valve 10, the fourth fluidic conduit 26 and into the fourth fluidic chamber 50. The second defined volume of gas 100 must be sufficient to force the second defined volume of fluid 92 through the fifth fluidic conduit 28, through the internal channel 12 in the rotating valve 10, through the fourth fluidic conduit 26 and into the fourth fluidic chamber 50. The fourth fluidic chamber 50 now contains a third defined volume of fluid 94 equal to the sum of the first defined volume of fluid 74 and the second defined volume of fluid 92 (FIG. 6F). It follows that the capacity of the fourth fluidic chamber 50 must be sufficient to hold both the first defined volume of fluid and the second defined volume of fluid. Any excess gas forced through the fifth fluidic conduit, through the internal channel in the rotating valve, through the fourth fluidic conduit and into the fourth fluidic chamber as a result of fully depressing of the third moveable piston 82 in the fifth fluidic chamber 52 can be bubbled through the third defined volume of fluid 94, in the fourth fluidic chamber 50 and vented through the first integral air vent 88.

The second integral air vent 90 preferably contains a fluid repellent coating and/or membrane to prevent the any fluid in the fifth fluidic chamber 52 accidentally leaking out of the device via said second integral air vent.

The rotating valve is then rotated a further 45 degrees in the clockwise direction to bring the fifth fluidic conduit 28 into communication with the sixth fluidic conduit 30 (FIG. 6G). The fourth moveable piston 84 seals a fourth defined volume of fluid 96 within the sixth fluidic chamber 54, and is held in a first position a height "h" above the base of the sixth fluidic chamber. It follows that the enclosed sixth fluidic chamber contains a pre-defined fourth volume of fluid 96, with a third defined volume of gas 102 separating the fourth moveable piston 84 from the pre-loaded fourth defined volume of fluid 96. The fifth fluidic chamber 52 is empty and the third moveable piston 82 is at a height h=0 above the base of the fifth fluidic chamber. As the fourth moveable piston 84 is depressed, the fourth defined volume of fluid 96 is forced through the sixth fluidic conduit 30, through the internal channel 12 in the rotating valve 10, and into the fourth fluidic conduit 28 and into the fifth fluidic chamber 52 (FIG. 6H). As a consequence, the third moveable piston 82 is forced vertically upwards as a result of the pressure being exerted upon it. Once the fourth moveable piston 84 has been depressed to a height h=0 above the base of the sixth fluidic chamber 54, all of the fourth defined volume of fluid 96 from the sixth fluidic chamber 54 has been forced through the sixth fluidic conduit 30, the internal channel 12 in the rotating valve 10, the fifth fluidic conduit 28 and into the fifth fluidic chamber 52. The third defined volume of gas 102 must be sufficient to force the fourth defined volume of fluid 96 through the sixth fluidic conduit 30, through the internal channel 12 in the rotating valve 10, through the fifth fluidic conduit 28 and into the fifth fluidic chamber 52. The fifth fluidic chamber 52 now contains the fourth defined volume of fluid 96 (FIG. 6I). It follows that the capacity of the fifth fluidic chamber 52 must be sufficient to hold the fourth defined volume of fluid. Once the third moveable piston 82 reaches its maximum height "h" above the base of the fifth fluidic chamber 52, any excess gas forced through the sixth fluidic conduit 30, through the internal channel 12 in the rotating valve 10, through the fifth fluidic conduit 28 and into the fifth fluidic chamber 52 as a result of fully depressing of the fourth moveable piston 84 in the sixth fluidic chamber 54 can be bubbled through the fourth defined volume of fluid 96, in the fifth fluidic chamber 52 and vented through the second integral air vent 90.

The rotating valve may then be rotated 45 degrees in the anti-clockwise direction so that the internal channel in the rotating valve brings the fourth fluidic conduit and the fifth fluidic conduit into communication. The third moveable piston 82 can then be fully depressed to force the fourth defined volume of fluid from the fifth fluidic chamber 52, through the fifth fluidic conduit 28, through the internal channel 12 in the rotating valve 10, into the fourth fluidic conduit 26 and into the fourth fluidic chamber 50. The fourth fluidic chamber 50 will then contain a fifth defined volume of fluid 98 equal to the sums of the first defined volume of fluid 74, the second defined volume of fluid 92 and the fourth defined volume of fluid 96 (FIG. 6J). It follows that the capacity of the fourth fluidic chamber 50 should be sufficient to hold the fifth defined volume of fluid 98. Any excess gas may be vented through the first integral vent 88.

In some embodiments, a sensor may be combined with and/or integrated into a microfluidic chip to monitor fluids in one or more fluidic conduits and/or one or more fluidic chambers. The sensor can be any sensor used for monitoring chemical, optical and/or electrical properties and/or constituents of a fluid, and may comprise, but not be limited to, impedance sensors, particle counters, lasers, LEDs, photodiodes, PMTs, pH sensors, EWOD, AM-EWOD, and other suitable sensor devices.

FIGS. 7A-C teach one embodiment in which fine fluid control is achieved through the use of at least one integral piston positioned orthogonally to at least one fluidic chambers. In particular, the pistons are designed to flow a fluid through at least one sensor in at least one fluidic conduit at a constant flow rate. In this illustrative embodiment, the housing contains a rotating valve with a substantially 'V' shaped internal channel and six fluidic conduits angularly separated by 60 degrees centered round the rotating valve (FIG. 7A). The first fluidic conduit 20 in is communication with a first fluidic chamber 44, which is open to ambient surroundings. The second fluidic conduit 22 is in communication with a second fluidic chamber 46 which is open to ambient surroundings. A third fluidic conduit 24 is in communication with a third fluidic chamber 48 which is closed using a first moveable piston 78. A fourth fluidic conduit 26 is in communication with a fourth fluidic chamber 50 which is closed using a second moveable piston 80. A fifth fluidic conduit 28 is in communication with a fifth fluidic chamber 52 which is further in communication with a third moveable piston 82 positioned within a piston housing 108 orthogonal to the fifth fluidic chamber 52 via a gas communication conduit 106. The piston housing 108 extends to the edge of the microfluidic device housing 18 where the piston housing can be integrated with an external stepping motor 110. A sixth fluidic conduit 30 is in communication with a sixth fluidic chamber 54 with a first integral air vent 88. The sixth fluidic conduit 30 is further in communication with a sensor 104. It is assumed that a series of fluidic operations has been carried out between the first fluidic conduit, second fluidic conduit, third fluidic conduit, fourth fluidic conduit and the fifth fluidic conduit such that there is a defined volume of fluid 74 residing in the fifth fluidic chamber 52. The gas communication conduit 106 may contain a fluid repellent coating and/or membrane to prevent the pre-loaded fluid in the fifth fluidic chamber 52 from accidentally passing through into the piston housing 108. The hydrophobic properties of the gas communication conduit, for example, repels aqueous based liquids whilst still allowing pressurized gas to pass through from the piston housing 108, via the gas communication conduit 106 and into the fifth fluidic chamber 52.

The rotating valve is positioned to bring the fifth fluidic conduit 28 and the sixth fluidic conduit 30 into communication via the internal channel 12 in the rotating valve 10. The third moveable piston 82 is depressed at a constant rate from the external edge of the piston housing 108 using the stepping motor 110, forcing the pre-defined volume of fluid 74 from the fifth fluidic chamber 52, through the fifth fluidic conduit 28, through the internal channel 12 in the rotating valve 10 and into the sixth fluidic conduit 30 (FIG. 7B). The defined volume of fluid passes through the sensor 104 in the sixth fluidic conduit, preferably at a constant flow rate determined by the rate at which the piston is depressed by the stepping motor 110, and analysed as it flows through the sensor 104. A first integral air vent 88 positioned above the sixth fluidic chamber 54 allows excess air to escape.

The third moveable piston 82 continues to be depressed at a constant rate until its final position where it makes contact with the gas communication conduit 106 (FIG. 7C). There is a sufficient volume of gas contained in the piston housing 108 to force the entire defined volume of fluid out of the fifth fluidic chamber 52 through the fifth fluidic conduit 28, the internal channel 12 in the rotating valve 10, the sixth fluidic conduit 30 and into the sixth fluidic chamber 54.

The sensor can be any sensor used for monitoring chemical, optical, thermal or electrical properties and/or constituents of a fluid, and may comprise, but not be limited to, impedance sensors, particle counters, lasers, LEDs, photodiodes, PMTs, pH sensors, EWOD, AM-EWOD, flow sensors, temperature sensors and other suitable sensor devices.

In a further embodiment, multiple sensors may be used to accurately determine the volume of fluid metered within the internal channel in the rotating valve. Engineering tolerances may be such that a rotating valve with an internal channel designed to be 5 ul may actually be 5+/−0.5 ul, e.g. +/−10%. For applications that require accurate, quantitative sample analysis, this could mean accidentally reporting, for example, a false negative or a false positive result. Therefore, one embodiment of the invention is to provide a self-calibrating microfluidic fluidic operations device. In one aspect, the actual volume of fluid metered within the internal channel in the rotating valve may be determined. This can be achieved by taking optical measurements before and/or after each fluidic operation at appropriate fluidic conduits and/or fluidic chambers. The values measured before and/or after each fluidic operation can then be compared to a calibration curve for the process in question, e.g. metering, diluting, lysing, mixing, binding, titrating etc. For metering operations, the technique enables any change in metered fluid, such as for example due to variations in engineering tolerances, or due to the presence of air bubbles in the internal channel in the rotating valve, to be accurately accounted for. The technique may additionally be employed to confirm that the correct volumes of fluid have been moved between conduits and/or chambers, for example 50 ul of fluorescent material has been accurately mixed with 50 ul of buffer, by comparing the actual output with a calibration curve for the process.

Figure 8A:
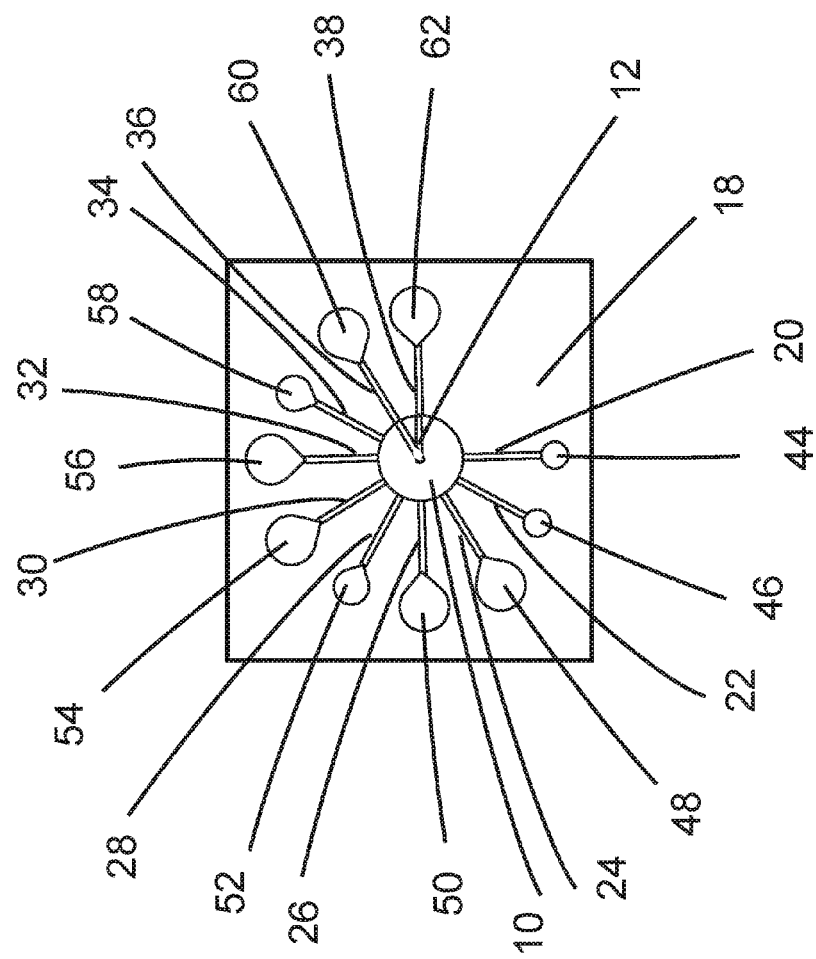
Figure 8E:
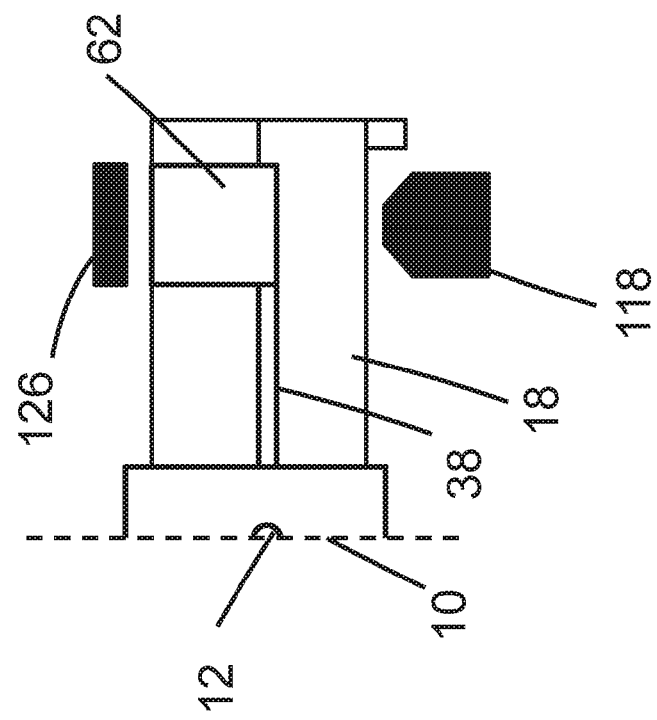
Figure 8D:
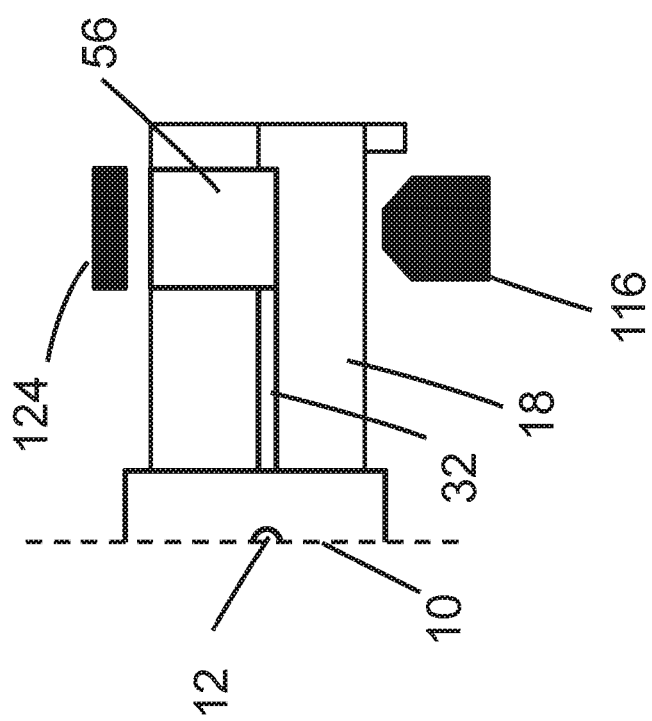

FIGS. 8A-E depict one embodiment of a microfluidic device with ten fluidic conduits and ten fluidic chambers within a housing 18, and a rotating valve 10 with a substantially 'V' shaped internal channel 12 (FIG. 8A) in which external sensors are strategically placed for taking optical measurements of the fluids being processed in fluidic chambers within the microfluidic device to produce a microfluidic device that can be individually calibrated whilst in use. The first fluidic conduit 20 in is communication with a first fluidic chamber 44. The second fluidic conduit 22 is in communication with a second fluidic chamber 46. A third fluidic conduit 24 is in communication with a third fluidic chamber 48. A fourth fluidic conduit 26 is in communication with a fourth fluidic chamber 50. A fifth fluidic conduit 28 is in communication with a fifth fluidic chamber 52. A sixth fluidic conduit 30 is in communication with a sixth fluidic chamber 54. A seventh fluidic conduit 32 is in communication with a seventh fluidic chamber 56. An eighth fluidic conduit 34 is in communication with an eighth fluidic chamber 58. A ninth fluidic conduit 34 is in communication with a ninth fluidic chamber 60, and a tenth fluidic conduit 38 is in communication with a tenth fluidic chamber 62. FIG. 8B teaches a first light source 112 placed below the first fluidic chamber 44, and a first photodetector 120 placed above the first fluidic chamber 44. FIG. 8C teaches a second light source 114 placed below the fourth fluidic chamber 50, and a second photodetector 122 placed above the fourth fluidic chamber 50. FIG. 8D depicts a third light source 116 placed below the seventh fluidic chamber 56, and a third photodetector 124 placed above the seventh fluidic chamber 56. FIG. 8E shows a fourth light source 118 placed below the tenth fluidic chamber 62, and a fourth photodetector 126 placed above the tenth fluidic chamber 62. The light sources may be an LED, laser or other suitable light source, and the photodetectors may be a photodiode, PMT, or other suitable photodetector for sensing light from an associated light sensor. Alternatively, a single light source and photodetector could be used, and the microfluidic device rotated such that optical measurements could be made at the first fluidic chamber 44, the fourth fluidic chamber 50, the seventh fluidic chamber 56, and the tenth fluidic chamber 62 respectively.

In a further aspect of the invention, a magnetic flea is used to mix, and/or lyse fluids in one or more fluidic chambers. For the most effective mixing and/or lysing conditions in a fluidic chamber with a magnetic flea to be realized, the volume of fluid in the fluidic chamber, the geometry of the mixing well, the size of the magnetic flea, and the rotational velocity of the magnetic flea should be optimized.

The aspect ratio of the volume of fluid within the fluidic chamber is defined as the ratio of the height of fluid in the chamber to the width of fluid in the chamber. Lower aspect ratios are associated with more efficient lysing and/or mixing. In a specific embodiment of the invention, the lysing and/or mixing fluidic chambers will have an aspect ratio between 0.1 and 4. The aspect ratio may be between 0.1 and 2, or between 0.2 and 0.95.

The edge of the magnetic flea may be flush against the internal wall of the fluidic chamber, or may be spaced away from the wall of the fluidic chamber. In a specific embodiment, the ratio of the length of the magnetic flea to the diameter of the fluidic chamber is greater than 0.5, and may be greater than 0.6 or greater than 0.7.

In a specific embodiment, the ratio of the height of the fluid to the height of the magnetic flea is at least 1.

The faster the magnetic flea rotates, the more efficient the mixing and/or lysing. In one embodiment, the magnetic flea may rotate at greater than 300 rpm, or greater than 500 rpm, or at 1400 rpm.

FIGS. 9A-C teach one embodiment where a magnetic flea and well geometry are optimized for lysing and mixing. FIG. 9A shows a microfluidic housing 18 with five fluidic conduits, five fluidic chambers, and a rotating valve 10 with a substantially 'V' shaped internal channel 12. The first fluidic conduit 20 is in communication with a first fluidic chamber 44. The second fluidic conduit 22 is in communication with a second fluidic chamber 46. A third fluidic conduit 24 is in communication with a third fluidic chamber 48. A fourth fluidic conduit 26 is in communication with a fourth fluidic chamber 50, with a magnetic flea 128 residing within the fourth fluidic chamber 50. A fifth fluidic conduit 28 is in communication with a fifth fluidic chamber 52. FIG. 9B depicts a fourth fluidic chamber 50 with a magnetic flea 128 in which the ratio of the length of the magnetic flea to the diameter of the fluidic chamber is 0.82. FIG. 9C furthers shows the fourth fluidic chamber 50 with a magnetic flea 128 containing a volume of fluid 130 with an aspect ratio of 0.38 as defined by the ratio of the height of fluid in the chamber to the width of fluid in the chamber.

The following describes examples that may be performed utilizing microfluidic devices configured in accordance with one or more of the embodiments described above. The following examples generally are illustrative of methods of performing a series of fluid operations in an integrated microfluidic device. The methods may include steps of providing a housing including a plurality of n microfluidic conduits, wherein n is at least three; providing a rotating valve having an internal channel with an entrance port and an exit port that are angularly separated; positioning the rotating valve in a first position to connect two of the n fluidic conduits via the internal channel; transferring a fluid from a first one of the n fluidic conduits into a second one of the n fluidic conduits connected to the first fluidic conduit via the internal channel; rotating the rotating valve to a second position in which a third one of the n fluidic conduits is connected via the internal channel to the second fluidic conduit; transferring the fluid from the second fluidic conduit to the third fluidic conduit via the internal channel; and performing at least one fluid operation on the fluid. The fluid operations performed may include at least one of metering or re-metering the fluid; mixing constituents within the fluid; labelling, incubating, lysing, quenching, diluting, titrating, or separating constituents within the fluid; and/or transferring the fluid between external conduits or chambers in fluid communication with one or more of the n fluidic conduits. Additional details of these various types of fluid operations are described in connection with the following examples.

Example 1—Lysing Red Blood Cells from a Whole Blood Sample 1 ul of whole human blood contains ~5 million red blood cells (RBCs), ~10,000 white blood cells (WBCs), and ~500,000 platelets. In order to accurately count the number of WBCs, the RBCs must be removed, i.e., lysed.

FIGS. 10A-J teach how the invention can be used to lyse RBCs from a whole blood sample enabling the WBCs to be counted.

In this embodiment, the fluidic device has five fluidic conduits centered round a rotating valve with an angular separation of 60 degrees between each of the fluidic conduits. The rotating valve 10 contains a substantially 'V' shaped internal channel 12 with the input and output ports separated by 60 degrees. The internal channel 12 defines a known volume enabling accurate metering of a sample of fluid, in this example blood. The first fluidic chamber 44 acts as the sample input chamber, and the first fluidic conduit 20 acts as the sample input conduit. The second fluidic conduit 22 serves as an overflow channel, and the second fluidic chamber 46 operates as an air vent. The third fluidic chamber 48 holds a predefined volume of lysis reagent 132, while the fifth fluidic chamber 52 holds a predefined volume of quench reagent 134. The fourth fluidic chamber 50 contains a magnetic flea 128 for carrying out the lysing and quenching reactions. The required volumes of lysis and quench reagent are calculated based on the volume of the internal channel in the rotating valve, which will be used to meter a defined volume of whole blood.

The rotating valve 10 is set to a first position where the internal channel 12 in the rotating valve connects the first fluidic conduit 20 and the second fluidic conduit 22 (FIG. 10A). Whole blood is introduced to the device via the first fluidic chamber 44 (FIG. 10B). The blood capillary fills the first fluidic conduit 20, the internal channel 12 in the rotating valve 10, and starts to fill at least a portion of the second fluidic conduit 22 (FIG. 10C). The internal channel 12 in the rotating valve 10 also is filled with blood. The rotating valve is rotated 60 degrees in a clockwise direction, placing the second fluidic conduit in communication with the third fluidic conduit. The second and third fluidic conduits are held at equal pressure, thus holding the metered volume of fluid within the internal channel in the rotating valve. This prevents any of the metered fluid accidentally entering the second or third fluidic conduits. The rotating valve is rotated another 60 degrees in a clockwise direction, thus metering a first metered volume of blood 136 within the internal channel in the rotating valve (FIG. 10D). The action of this rotation further acts to isolate the first metered volume of blood 136 from the first fluidic conduit 20, and the second fluidic conduit 22, and places the third fluidic conduit 24 in communication with the fourth fluidic conduit 26.

Figure 10F:
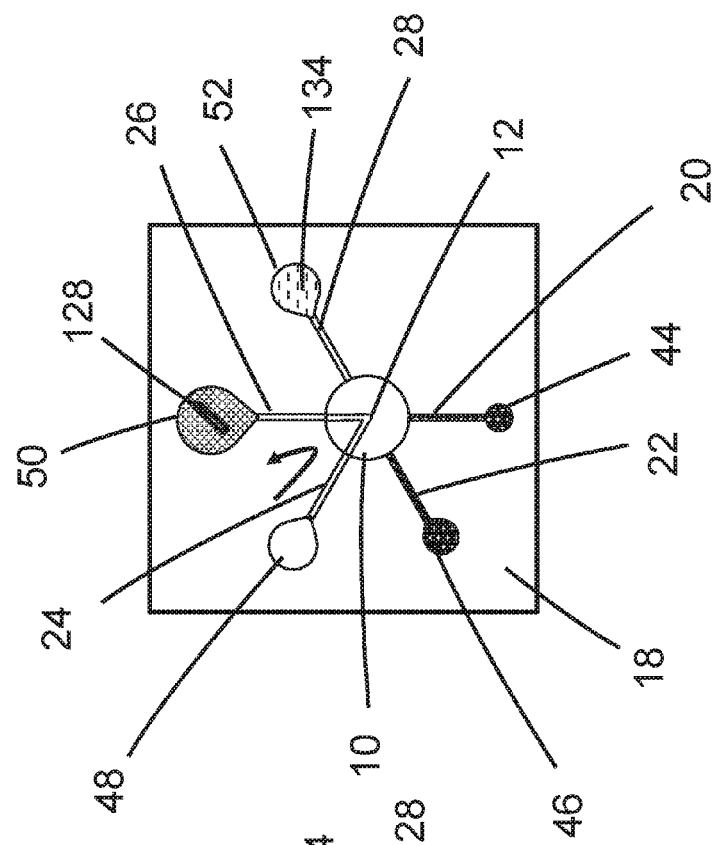
Figure 10E:
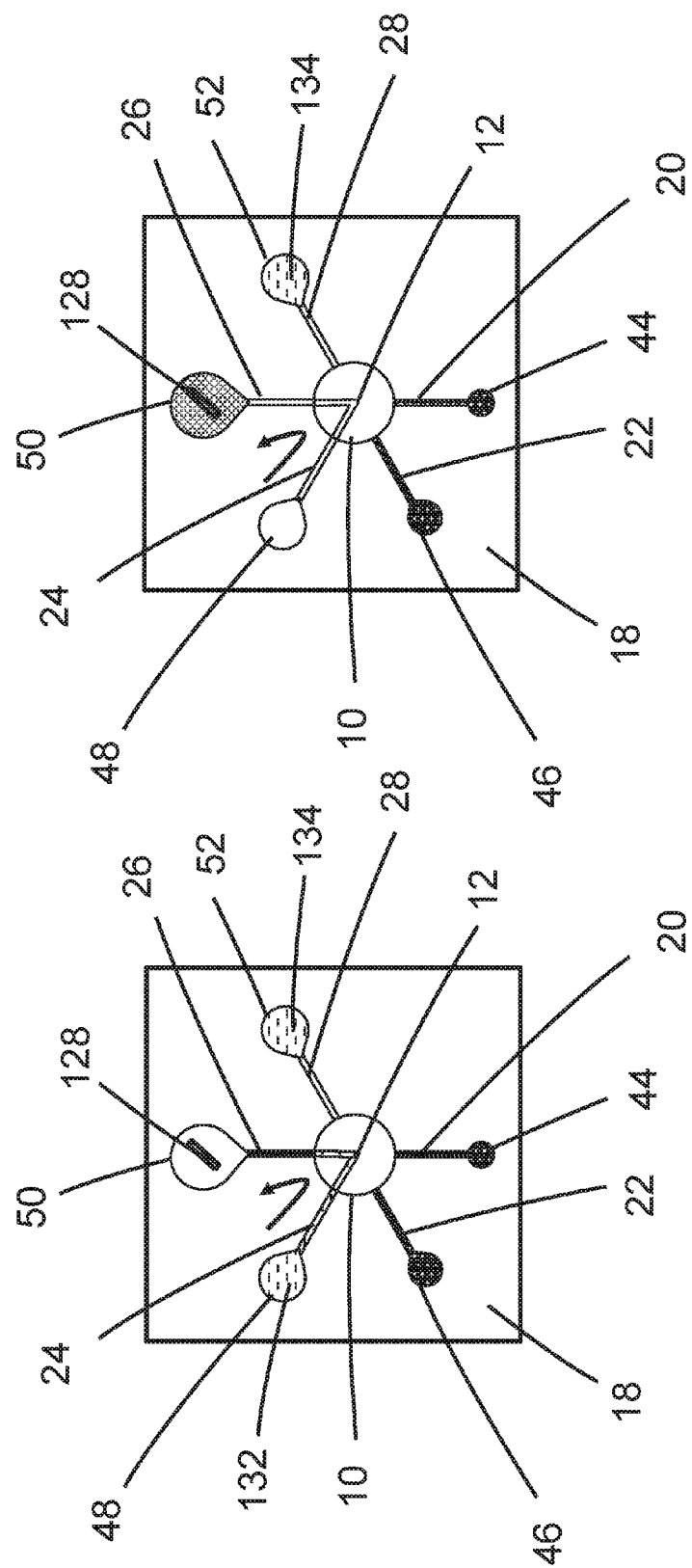

Positive gas pressure is used to displace the defined volume of lysis reagent 132 from the third fluidic chamber 48, flush the first metered volume of blood 136 out of the internal channel 12 within the rotating valve 10, and into the fourth fluidic chamber 50 (FIG. 10E). The magnetic flea 128 mixes the first metered volume of blood 136 and defined volume of lysis reagent 132 for a predetermined length of time, introducing a minimum amount of shear required for optimal lysing of the red blood cells (FIG. 10F).

The rotating valve 10 is then rotated a further 60 degrees in a clockwise direction to connect the fifth fluidic conduit 28 and the fourth fluidic conduit 26 (FIG. 10G). Positive gas pressure is used to displace the defined volume of quench reagent 134 from the fifth fluidic chamber 52, through the internal channel 12 in the rotating valve 10 and into the fourth fluidic chamber 50 (FIG. 10H). The magnetic flea 128 is then used to mix the defined volume of quench reagent with the lysed blood already present in the fourth fluidic chamber 50 to halt the lysis reaction and preserve the white blood cells for counting (FIG. 10I).

The rotating valve 10 can, optionally, then be moved to a final position where the internal channel 12 does not connect any fluidic conduits in the housing together, thus preventing accidental movement of fluid around the device (FIG. 10J). The sample can then be removed and analysed using a suitable haematology cell counter.

Preferably, the blood that is input into the device will be exposed to an anti-coagulant agent, e.g. EDTA salts, heparin or the like. Preferably, the first fluidic chamber 44, the first fluidic conduit 20 and/or the internal channel 12 in the rotating valve 10, will have their surfaces pre-treated with such an anti-coagulation agent. Such compounds may be adhered to the surfaces of the conduit walls. Alternatively, anti-coagulation agents may be added to the pre-loaded defined volume of lysis reagent 132 in the third fluidic chamber 48.

The lysis reagent is any reagent mixture containing a chemical known to lyse RBCs, such as for example saponins, quarternary ammonium salts, or the like. Preferably, the lysis reagent used contains saponin. The lysis reagent may be 0.12% v/v formic acid and 0.05% w/v saponin. The quench reagent is any reagent mixture known to halt or substantially reduce the rate of RBC lysis. The quench reagent may be 0.6% w/v sodium carbonate and 3% w/v sodium chloride. In exemplary embodiments, the blood:lysis:quench reagents are mixed in a ratio of 1:12:5.3.

Example 2—Blood Cell Labelling, Lysing and Quenching

FIGS. 11A-H teach how white blood cells in whole blood sample can be fluorescently labelled in a microfluidic device and prepared for analysis.

In this embodiment, the fluidic housing 18 has six fluidic conduits centered around a rotating valve with an angular separation of 45 degrees between each of the fluidic conduits. The rotating valve 10 contains a substantially 'V' shaped internal channel 12 with the input and output ports separated by 45 degrees. This internal channel 12 defines a known volume enabling accurate metering of whole blood.

The device includes a first fluidic chamber 44 and a first fluidic conduit 20 which act as the blood sample input chamber and conduit. The third fluidic chamber 48 holds a predefined volume of a fluorescent label reagent 138 suitable for labeling a predefined marker on the white blood cells. The fourth fluidic chamber 50 contains a magnetic flea 128 and acts as the mixing, lysing, and quenching chamber. The fifth fluidic chamber holds a predefined volume of lysis reagent 132, and the sixth fluidic chamber holds a predefined volume of a quench reagent 134. The required predefined volumes of fluorescent label, lysis and quench reagents are calculated based on the volume of the internal channel in the rotating valve.

The rotating valve is set to a first position in which the internal channel 12 in the rotating valve 10 puts the first fluidic conduit 20 and the second fluidic conduit 22 into communication. Whole blood is introduced to the device via the first fluidic chamber 44 (FIG. 11A).

The blood capillary fills the first fluidic conduit 20, the internal channel 12 in the rotating valve 10, and starts to fill at least a portion of the second fluidic conduit 22. The internal channel 12 within the rotating valve 10 is completely filled with blood (FIG. 11B).

Figures 11C, 11D:
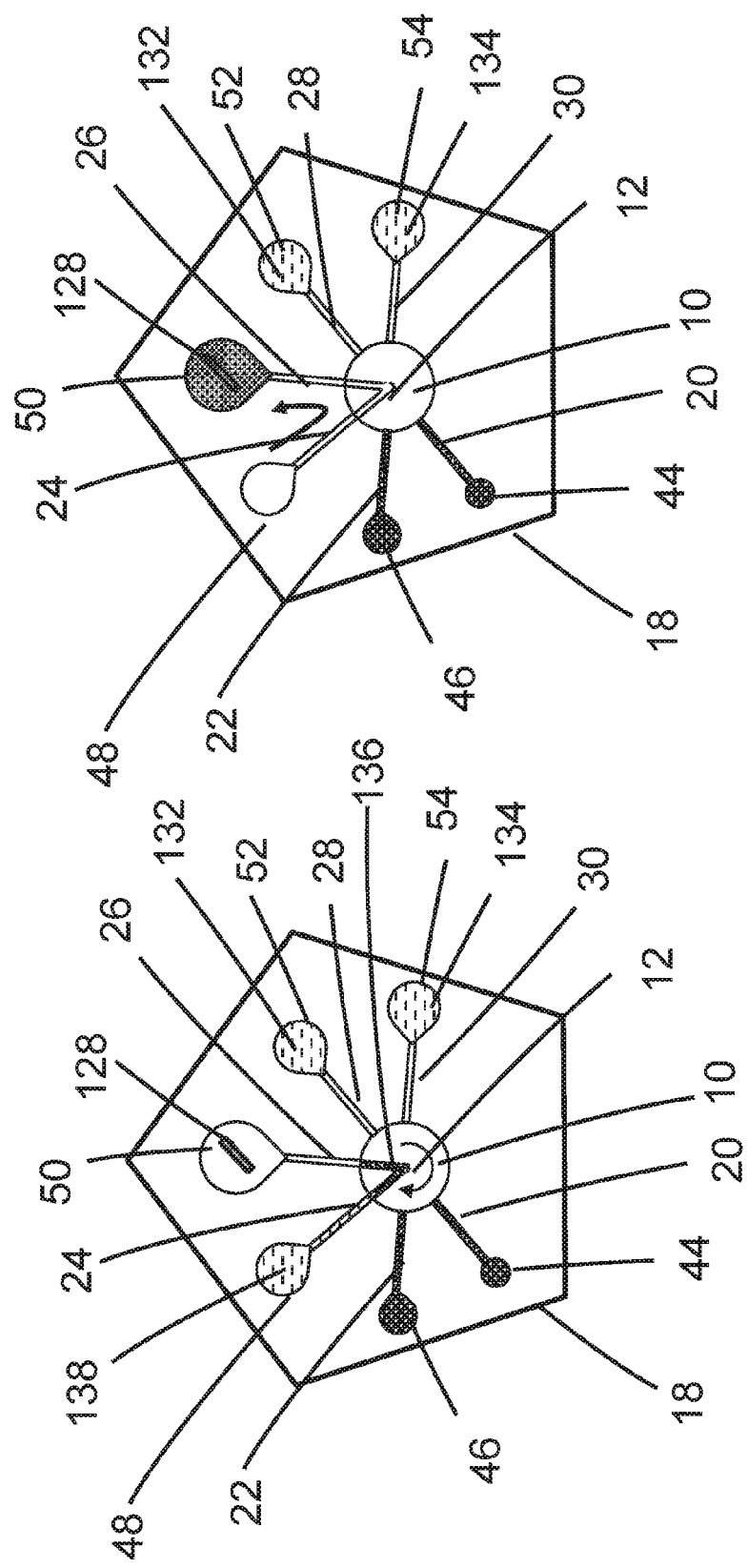

The rotating valve is rotated 45 degrees in a clockwise direction, placing the second fluidic conduit in communication with the third fluidic conduit via the internal channel in the rotating valve. The second and third fluidic conduits are held at equal pressure, thus preventing any of the fluid in the internal channel in the rotating valve accidentally exiting the internal channel in the rotating valve. The rotating valve is rotated a further 45 degrees in a clockwise direction, metering a defined volume of blood 136 within the internal channel 12 within the rotating valve 10 in the process. The metered volume of blood 136 is thus isolated from the first fluidic conduit 20 and the second fluidic conduit 22. The rotation of the rotating valve further puts the third fluidic conduit 24 in communication with the fourth fluidic conduit 24 via the internal channel 12 in the rotating valve 10, which contains the metered volume of blood 136 (FIG. 11C).

Positive gas pressure is used to displace the defined volume of fluorescent label reagent 138 out of the third fluidic chamber 48, through the third fluidic conduit 24, to flush the metered volume of blood 136 out of the internal channel 12 within the rotating valve 10, and into the fifth fluidic chamber 50 via the fifth fluidic conduit 26 for incubation. This provides an environment to facilitate the binding of the fluorescent label to the white blood cells (FIG. 11D). The magnetic flea gently agitates the whole blood and fluorescent label reagent for incubation of a predetermined length of time. One role of the magnetic flea at this point is to help prevent sedimentation of the sample.

The rotating valve 10 is then rotated a further 45 degrees in the clockwise direction so that the internal channel 12 within the rotating valve 10 puts the fourth fluidic conduit 26 in communication with the fifth fluidic conduit 28 (FIG. 11E).

Positive gas pressure is used to displace the defined volume of lysis reagent 132 from the fifth fluidic chamber 52, through the internal channel 12 in the rotating valve 10 and into the fourth fluidic chamber 50 via the fourth fluidic conduit 26 (FIG. 11F). The magnetic flea is then used to mix the defined volume of lysis reagent with the fluorescently labeled white blood cells in order to lyse, e.g. remove, the red blood cells.

Figure 11G:
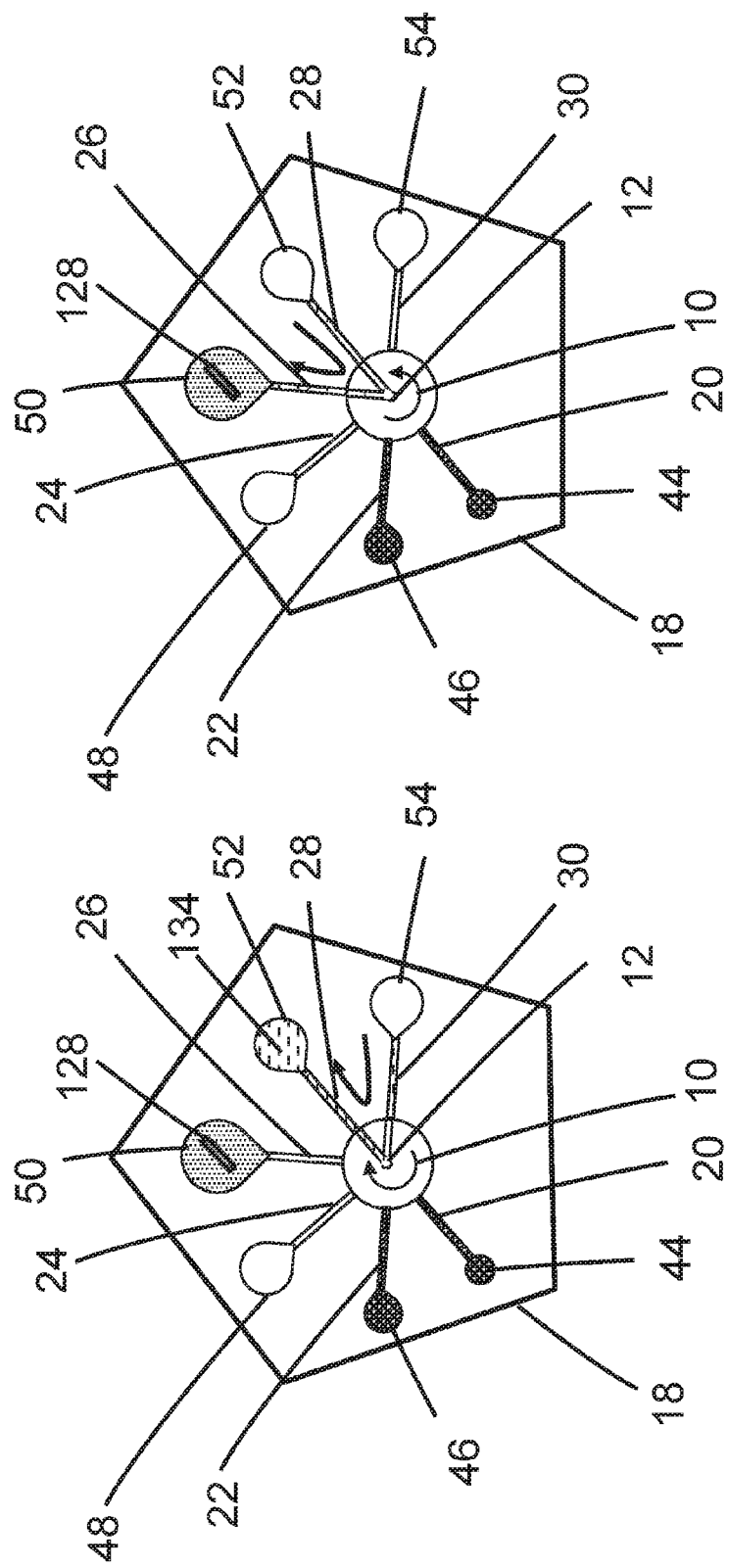

While the labeled blood is being lysed, the rotating valve 10 is rotated clockwise by 45 degrees for the internal channel 12 within the rotating valve 10 to connect the fifth fluidic conduit 28 with the sixth fluidic conduit 30. Positive gas pressure is applied to the sixth fluidic chamber 54 containing the defined volume of quench reagent 134. The positive gas pressure forces the defined volume of quench reagent 134 through the sixth fluidic conduit 30, through the internal channel 12 in the rotating valve 10, through the fifth fluidic conduit 28 and into the fifth fluidic chamber (FIG. 11G).

Figure 11H:
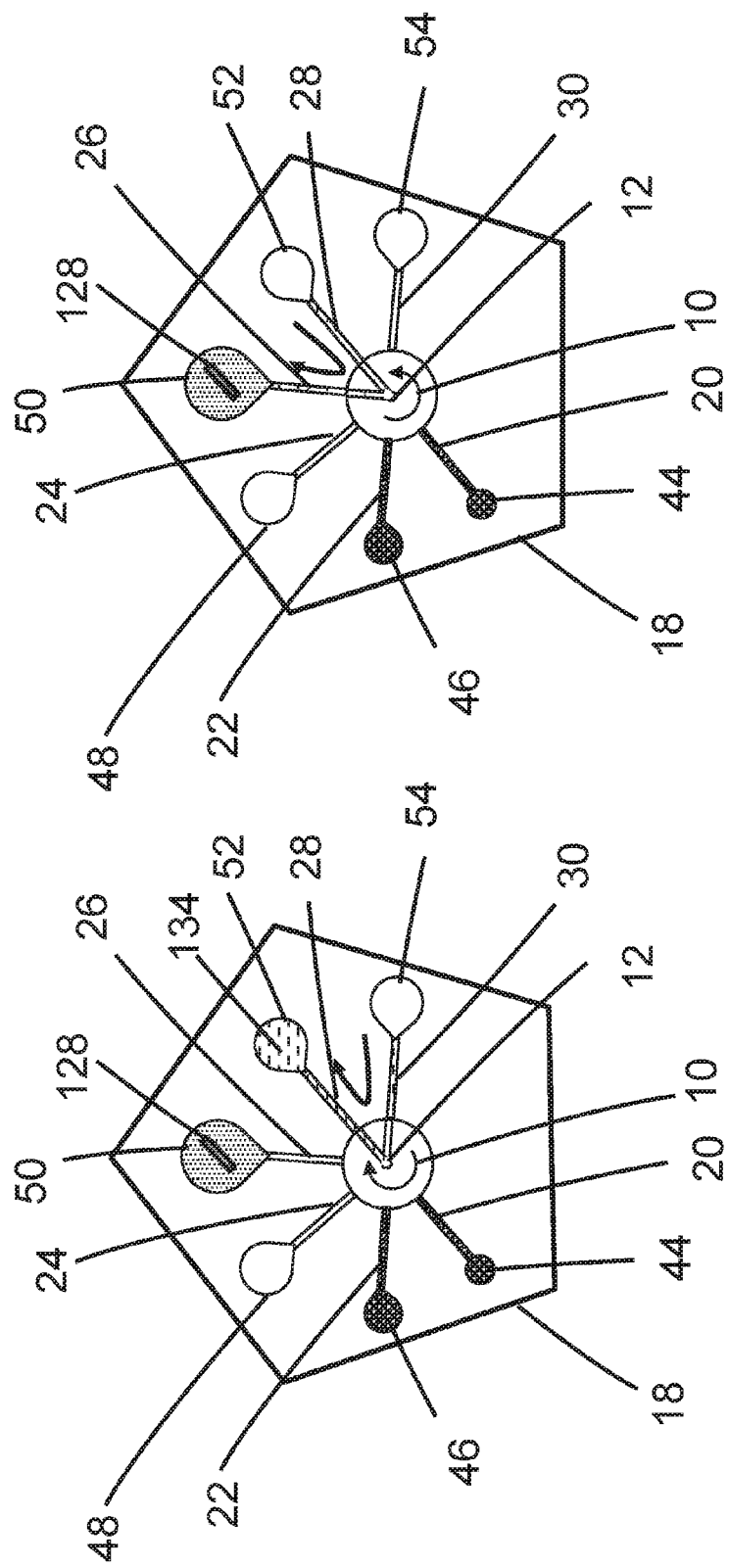

The rotating valve is then rotated anti-clockwise by 45 degrees to reconnect the fourth fluidic conduit 26 to the fifth fluidic conduit 28 via the internal channel 12 in the rotating valve 10. Positive gas pressure applied to the fifth fluidic chamber 52 forces the defined volume of quench reagent through the fifth fluidic conduit 28, the internal channel 12 in the rotating valve 10 and into the fourth fluidic chamber 50, where it neutralizes the lysis reaction (FIG. 11H).

If desired, the rotating valve can then be moved to a final position where it does not connect any fluidic conduits in the housing, thus preventing accidental movement of fluid around the device. The labeled and lysed blood sample can then be analysed using any suitable haematology cell counter with fluorescence monitoring capabilities.

The blood that is input into the device may be exposed to an anti-coagulant agent, such as for example EDTA salts, heparin or the like. The first fluidic chamber 44, the first fluidic conduit 20 and/or the internal channel 12 in the rotating valve 10, may have their surfaces pre-treated with such an anti-coagulation agent. Such compounds may be adhered to the surfaces of the channel walls. Alternatively, anti-coagulation agents may be added to the pre-loaded defined volume of fluorescent label reagent 138 in the third fluidic chamber 48.

The lysis reagent is any reagent mixture containing a chemical known to lyse RBCs, such as for example saponins, quarternary ammonium salts or the like. The lysis reagent used may contain saponin. The lysis reagent may be 0.12% v/v formic acid and 0.05% w/v saponin. The quench reagent is any reagent mixture known to halt or substantially reduce the rate of RBC lysis. The quench reagent may be 0.6% w/v sodium carbonate and 3% w/v sodium chloride. In exemplary embodiments, the blood:lysis:quench reagents are mixed in a ratio of 1:12:5.3.

The fluorescent label may be one designed to bind to a CD marker on the surface of a WBC. Is some embodiments, the fluorescent label reagent may comprise several different fluorescent labels that bind to different CD markers.

Example 3—High Ratio Serial Dilution of a Sample 1 ul of whole human blood contains ~5 million red blood cells (RBCs). In particular, this example demonstrates how the invention can be used to carry out a high ratio dilution of whole blood so that red blood cells and platelets can be counted. FIGS. 12A-J teach how a whole blood sample can be diluted in a ~1:10,000 ratio using a substantially reduced volume of diluting reagent compared to a conventional single step dilution (e.g. 1 ul whole blood into 10 ml of diluting regent).

In this example, the fluidic device has ten fluidic conduits centered around a rotating valve with an angular separation of 30 degrees between each of the adjacent conduits. The rotating valve 10 contains a 'V' shaped internal channel 12 with the input and output ports separated by 30 degrees. This internal channel 12 defines a known 3 ul volume enabling accurate metering of a sample of blood. The first fluidic chamber 44 acts as the blood input chamber and the first fluidic conduit 20 acts as the blood input conduit. The second fluidic conduit 22 serves as a first overflow conduit, and the second fluidic chamber 46 serves as an air vent. The third fluidic chamber 48, sixth fluidic chamber 54, and ninth fluidic chamber 60 each contain 64.5 ul of a diluting reagent. The fourth fluidic chamber 50, the seventh fluidic chamber 56, and the tenth fluidic chamber 62 each contain a magnetic flea (not shown for clarity). The fifth fluidic conduit 28 acts as a second overflow conduit, and the fifth fluidic chamber 52 serves as a second air vent. The eighth fluidic conduit 34 serves as a third overflow conduit, and the eighth fluidic chamber 58 serves as a third air vent.

The rotating valve is set to a first position such that the internal channel 12 in the rotating valve 10 brings the first fluidic conduit 20 and the second fluidic conduit 22 into communication (FIG. 12A).

The whole blood sample is introduced to the device via the first fluidic chamber 44. The whole blood sample capillary fills the first fluidic conduit 20, the internal channel 12 in the rotating valve 10, and starts to fill at least a portion of the second fluidic conduit 22. The internal channel 12 in the rotating valve 10 now contains a defined 3 ul volume of whole blood (FIG. 12B).

Figure 12C:
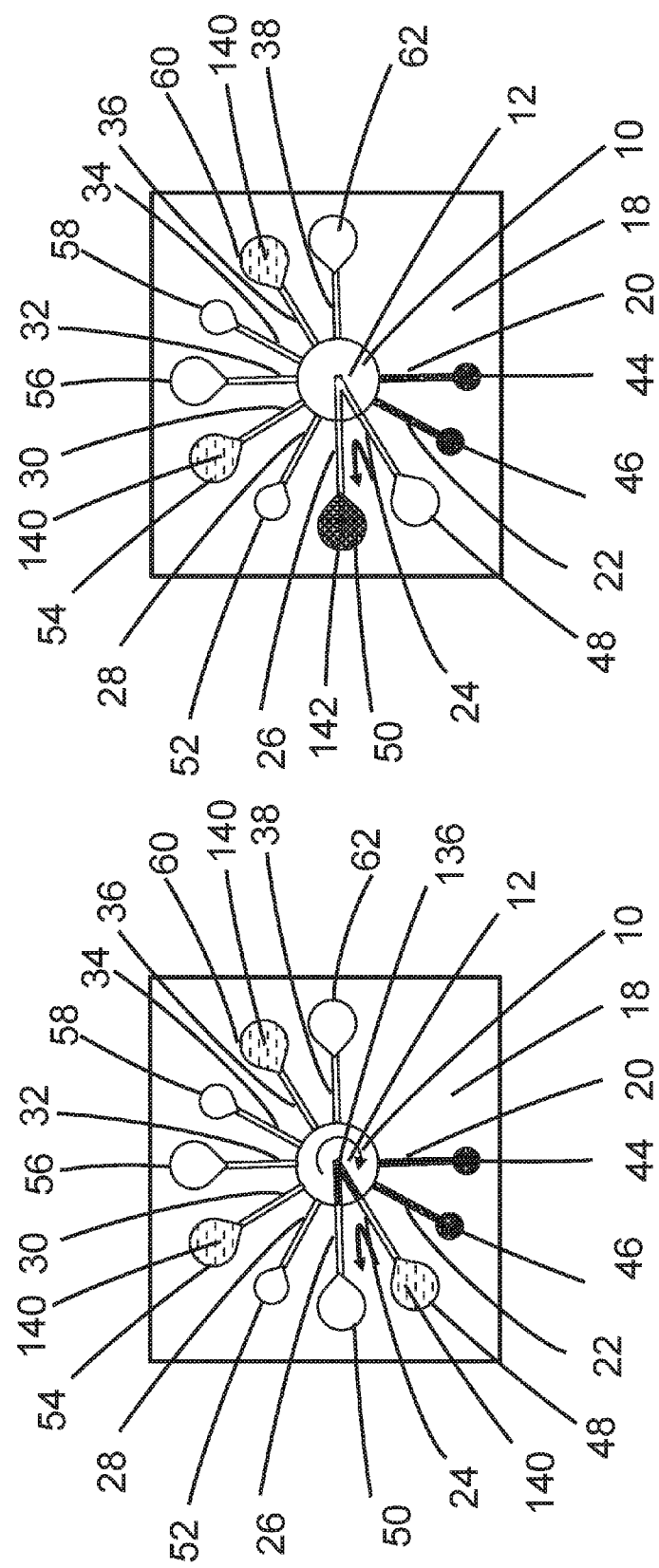

The rotating valve is rotated 60 degrees in a clockwise direction to isolate the first metered volume of blood 136 from the first fluidic conduit 20 and the second fluidic conduit 22, and to connect the third fluidic conduit 24 with the fourth fluidic conduit 26 (FIG. 12C). The second and third fluidic conduits are briefly placed in communication with each other via the internal channel in the rotating valve upon this rotation, but no fluidic operations are carried out between the second and third fluidic conduits; the volume of fluid within the internal channel within the rotating valve is maintained within the internal channel of the rotating valve.

Figure 12D:
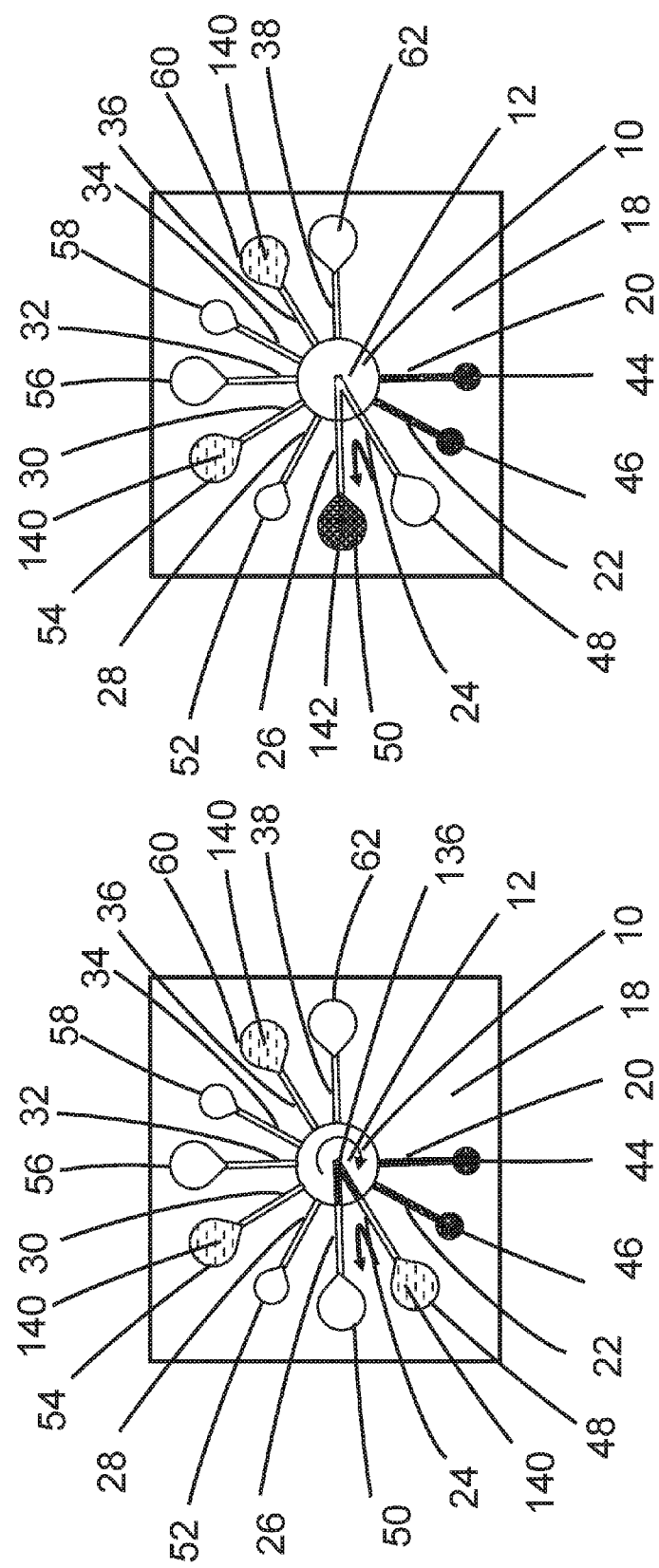

Positive gas pressure is used to displace the 64.5 ul of diluting reagent 140 from the third fluidic chamber 48, to flush the metered sample of blood 136 out of the internal channel 12 within the rotating valve 10, and into the fourth fluidic chamber 50 via the fourth fluidic conduit 26. A magnetic flea (not shown) in the fourth fluidic chamber 50 gently agitates the metered whole blood and diluting reagent to achieve complete mixing and the first 1:21.5 dilution (FIG. 12D). The fourth fluidic chamber 50 now contains a defined volume of a 1:21.5 diluted blood sample 142.

Figure 12E:
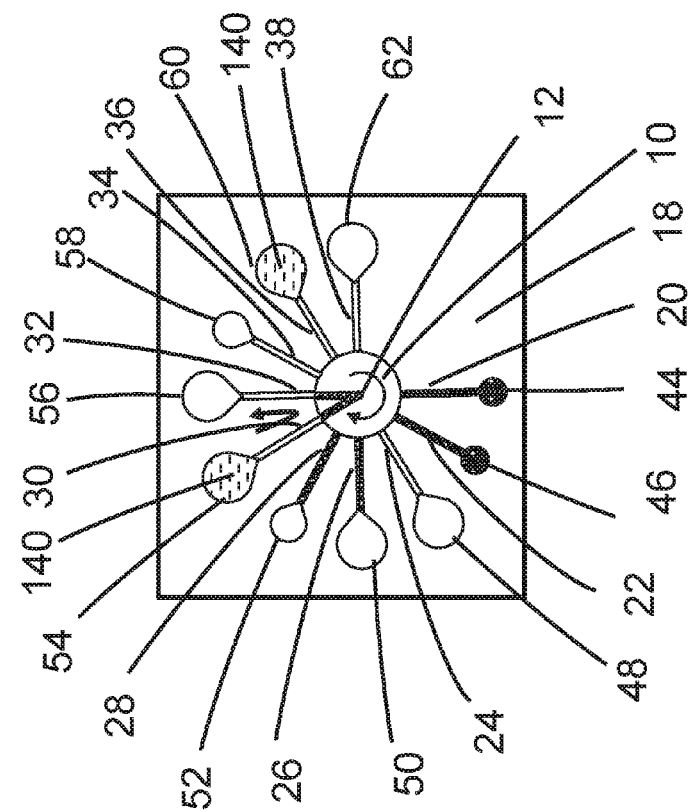

The rotating valve is then rotated another 30 degrees in the clockwise direction, joining the fourth fluidic conduit 26 to the fifth fluidic conduit 28 via the internal channel 12 in the rotating valve 10. Positive gas pressure is applied to the fourth fluidic chamber 50 to force the 1:21.5 diluted blood sample fluid sample into the fourth fluidic conduit 26, the internal channel 12 in the rotating valve 10 with at least a portion of the 1:21.5 diluted blood sample fluid entering the fifth fluidic conduit 28 (FIG. 12E). The internal channel 12 in the rotating valve 10 now contains 3 ul of 1:21.5 diluted blood sample.

Figure 12F:
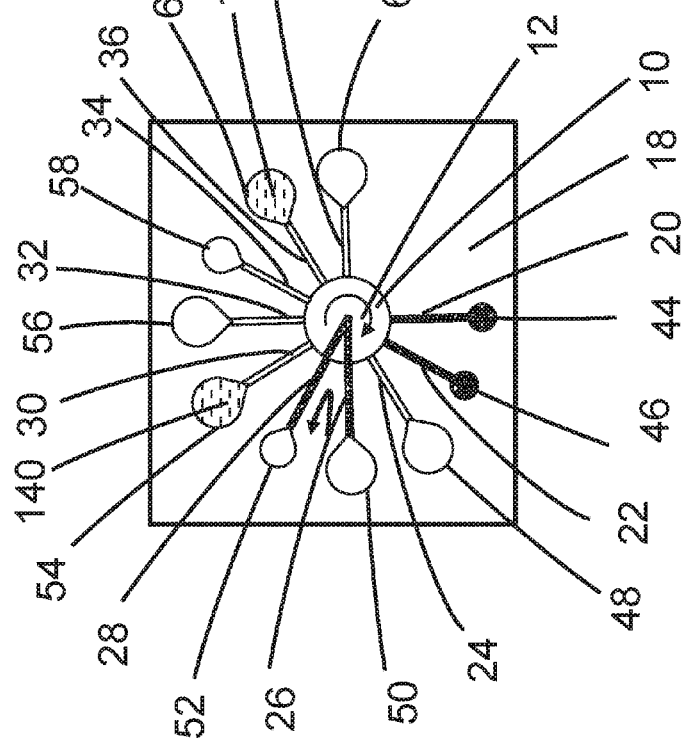

At this point the rotating valve is rotated 60 degrees in the clockwise direction to isolate the metered volume of 1:21.5 diluted blood sample fluid from the fourth fluidic conduit 26 and the fifth fluidic conduit 28, and bring the sixth fluidic conduit 30 into communication with the seventh fluidic conduit 32 via the internal channel 12 in the rotating valve that contains 3 ul of 1:21.5 diluted blood sample (FIG. 12F).

Positive gas pressure is used to displace the 64.5 ul of diluting reagent 140 from the sixth fluidic chamber 54, to flush the metered 1:21.5 diluted blood sample fluid out of the internal channel 12 within the rotating valve 10, and into the seventh fluidic chamber 56 via the seventh fluidic conduit 32. A magnetic flea (not shown for clarity) in the seventh fluidic chamber 56 gently agitates the sample to achieve complete mixing and the second 1:21.5 dilution (FIG. 12G). The total dilution at this stage is 1:462.25.

The rotating valve is then rotated another 30 degrees in the clockwise direction, joining the seventh fluidic conduit 32 with the eighth fluidic conduit 34 via the internal channel 12 of the rotating valve 10. Positive gas pressure is applied to the second mixing chamber to force the 1:462.25 diluted blood sample 144 fluid into the seventh fluidic conduit 32, into the internal channel 12 in the rotating valve 10 with at least a portion of the 1:462.25 diluted blood sample entering the eighth fluidic conduit 34. The internal channel in the rotating valve now contains 3 ul of 1:462.25 diluted blood sample (FIG. 12H).

Figures 12I, 12J:
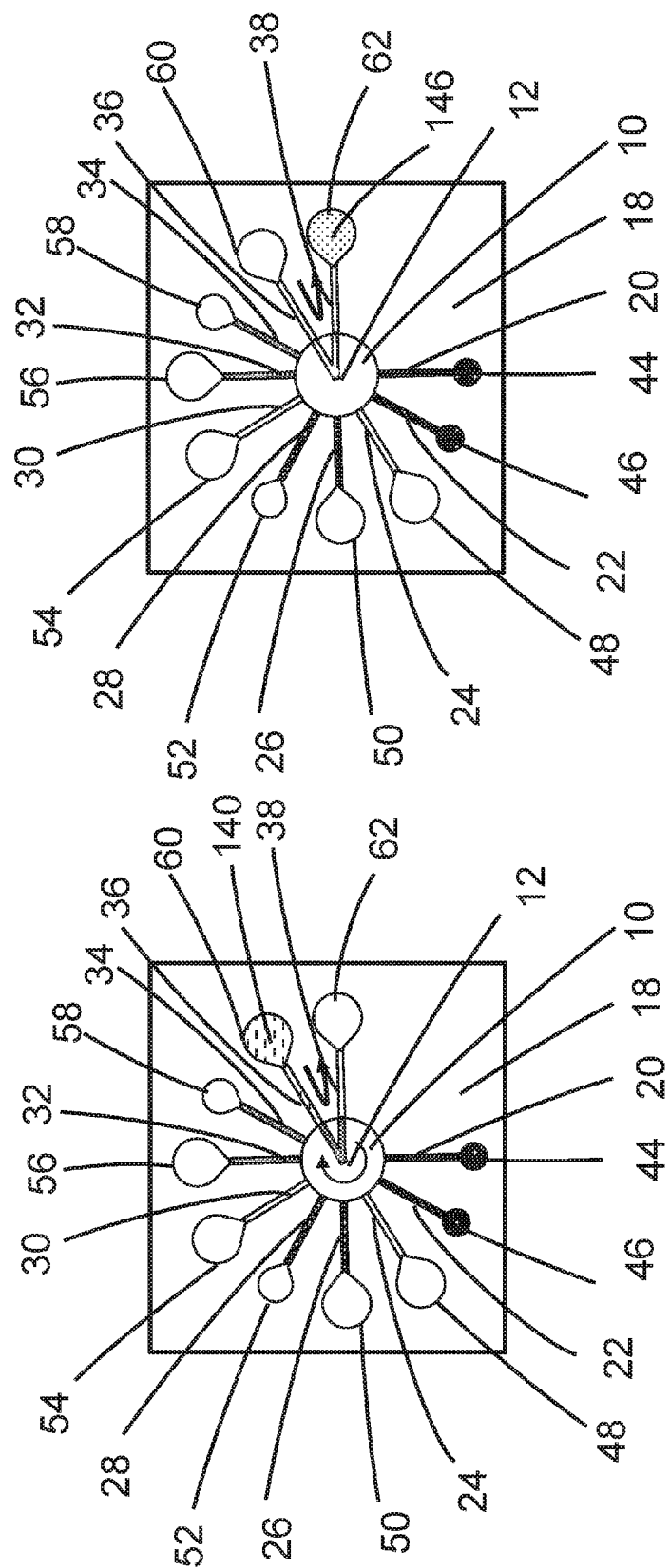

At this point the rotating valve is rotated 60 degrees in the clockwise direction to isolate the metered volume of 1:462.25 diluted blood sample in the internal channel 12 in the rotating valve 10 from the seventh fluidic conduit 32 and the eighth fluidic conduit 34, and bring the ninth fluidic conduit 36 into communication with the tenth fluidic conduit 38 via the internal channel 12 in the rotating valve 10 (FIG. 12I).

Positive gas pressure is used to displace the 64.5 ul of diluting reagent 140 from the ninth fluidic chamber 60, to flush the metered 1:462.25 diluted blood sample out of the internal channel 12 within the rotating valve 10, and into the tenth fluidic chamber 62. A magnetic flea (not shown for clarity) in the tenth fluidic chamber 62 gently agitates the sample to achieve complete mixing and the third 1:21.5 dilution. The final dilution ratio is 1:9,938, with the tenth fluidic chamber containing a defined volume of 1:9,938 diluted blood 146.

In this example, a 1:9,938 (21.5*21.5*21.5=9,938) dilution can be carried out using a total of 64.5*3=193.5 ul of diluting reagent. This is substantially less than the 9.938 ml of diluting reagent that would have been required if the dilution was carried out in a single step as performed conventionally. A similar device operated along similar principles could be used to carry out a ~1:10,000 dilution using the same 3 ul metering valve but in only two dilution steps. In this instance, there would be two fluidic chambers each holding 300 ul of diluting reagent. The first dilution step would dilute 3 ul of whole blood into 300 ul of diluting reagent (1:100 dilution). 3 ul of this diluted sample would then be metered in the internal channel in the rotating valve and diluted into a second fluidic chamber containing a further 300 ul of diluting reagent (a second 1:100 dilution). The final diluted solution would have been diluted by a ratio of 1:10,000 using a total of 600 ul of diluting reagent, still substantially less than then 10 ml required to complete the dilution in a conventional single step but over three times more than the 193.5 ul total volume of diluting reagent required to obtain a 1:9,938 dilution using the three step method described above.

Optionally, optical measurements, e.g. fluorescence and/or absorption measurements, can be made through at least three of the first fluidic chamber, the fourth fluidic chamber, the seventh fluidic chamber and/or the tenth fluidic chamber. By comparing the optical measurements from each of the fluidic chambers against a calibration curve for the dilution, and given that the volume of diluting reagent at each step is known, then the exact volume of fluid metered within the rotating valve at each metering stage can be determined. NOTE: It is highly unlikely that over a 10,000 fold dilution range that any calibration curve will be entirely linear. In turn, the exact dilution ratio after the three metering and dilution steps can be accurately calculated. This enables any change in the volume metered within the internal channel within the rotating valve, e.g. slight variations in the volume of the internal channel due to the tolerances in manufacturing process, to be accurately accounted for. Alternatively, the optical measurements may be made at the first fluidic conduit, the fourth fluidic conduit, the seventh fluidic conduit, and/or the tenth fluidic conduit.

It is important to know how much blood has been metered in the internal channel in the rotating valve, as any slight variation in metering can have a significant impact on the final dilution ratio, and hence could lead to inaccuracies in diagnoses. For example, assume that the engineering tolerance on producing a 3 uL internal channel within a rotating valve is +/−10%. The internal channel in the rotating valve may have a volume anywhere between 2.7 uL and 3.3 uL. Assuming that three 1:21.5 dilutions are carried out in series, e.g. 64.5 uL is preloaded into three fluidic chambers as described above, then the expected 1:9938 final dilution ratio is only correct if the internal channel within the rotating valve actually meters 3 uL. Assuming that 1 uL of whole human blood contains 5 million RBCs, this 1:9938 dilution results in an average of 503 RBCs/uL.

However, if the internal channel actually only meters 2.7 uL instead of 3 uL, the dilution ratio at each dilution stage is 1:23.89 rather than 1:21.5, giving a final dilution ration of 1:13633 and an average of 367 RBCs/uL. If the internal channel actually meters 3.3 uL instead of 3 uL, then the dilution ration at each dilution stage becomes 1:19.55 producing a final total dilution ratio of 1:7472 and an average of 669 RBCs/uL. These numbers are summarized in Table 1:

TABLE 1

| Volume of internal channel (uL) | Dilution ratio at each fluidic chamber (64 uL dilutent fluid) | Total dilution ratio at final fluidic chamber | Equivalent no of RBCs/uL after final dilution |
| --- | --- | --- | --- |
| 2.7 | 1.0:23.89 | $1:23.89^3 = 13633$ | 367 |
| 3.0 | 1.0:21.5 | $1:21.5^3 = 9938$ | 503 |
| 3.3 | 1.0:19.55 | $1:19.55^3 = 7472$ | 669 |

Assuming that an abnormally high number of RBCs after a 1:9938 dilution is 604 RBCs/uL, then it is apparent that if the internal channel meters 3.3 uL when it was expected to meter 3 uL that a false positive result may be returned as the 3.3 uL metered and diluted blood gives an equivalent of 669 RBCs/uL, which is greater than the 604 RBCs/uL cutoff, unless additional calibration measures are adopted.

Preferably, the sample fluid will be whole blood and the microfluidic device used to prepare a whole blood sample for RBC counting. The number of RBCs in the final diluted sample can then be analysed using any suitable cell counter.

Alternatively, this method of dilution can be used for any sample that requires diluting, particularly a final high ratio dilution.

Example 4—Full Blood Count 1 ul of whole human blood contains ~5 million red blood cells (RBCs), ~10,000 white blood cells (WBCs), and ~500,000 platelets. In order to accurately count the number of WBCs, the RBCs must be removed, i.e., lysed. To enable the RBCs to be counted accurately, a whole blood sample is diluted, for example in a 1:5,000 to 1:40,000 ratio. The whole blood sample may be diluted in a 1:10,000 to 1:20,000 ratio, or diluted in a 1:10,000 ratio. Platelets are counted preferably alongside the RBCs. It follows that there are two different sample preparation protocols; one for WBCs, and the other for RBCs and platelets combined.

Figure 13:
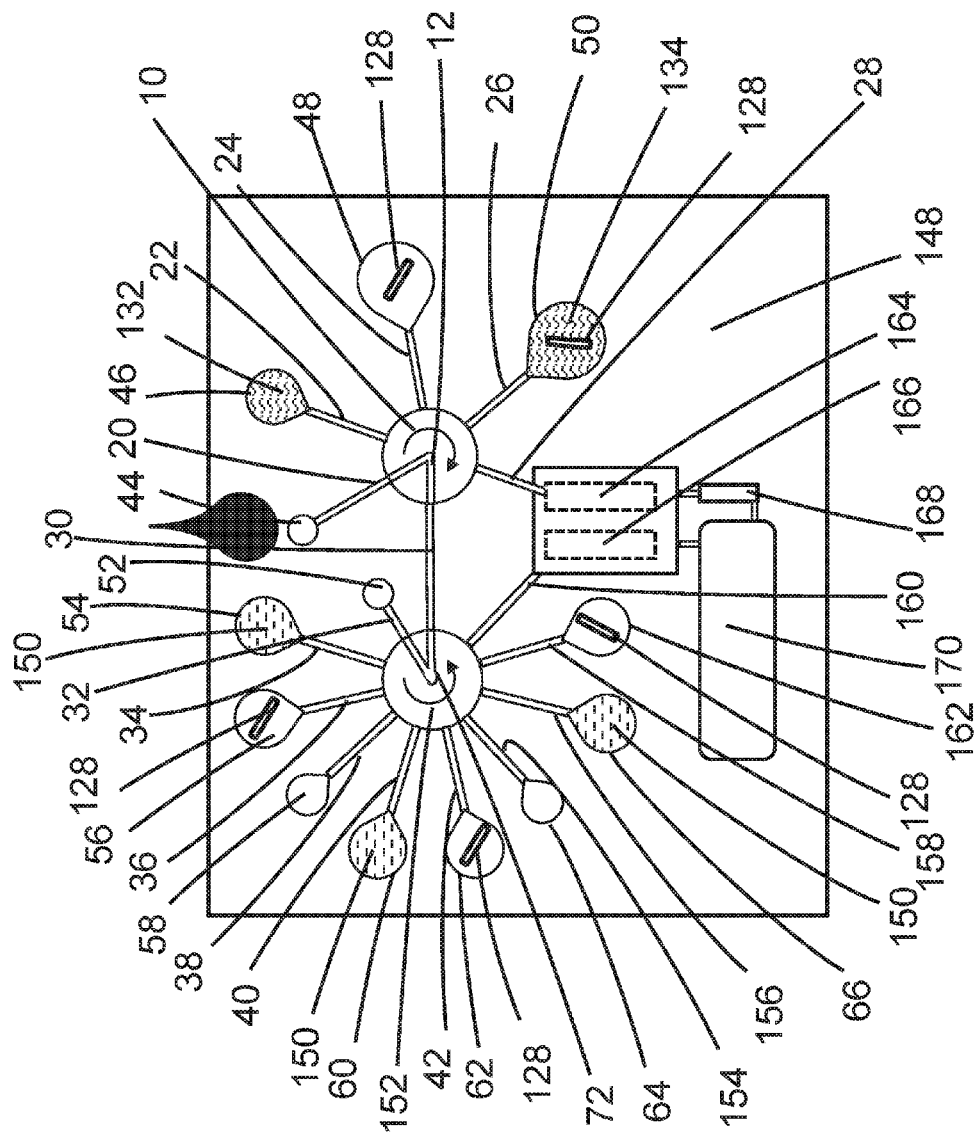
FIG. 13 depicts how the invention is used in accordance with the described Example 4.

FIG. 13 teaches how the invention can be used to prepare a whole blood sample so that WBCs, RBCs, and platelets can be counted using two separate integrated microfluidic cell counters in a single fluidic cartridge. The fluidic cartridge contains two rotating valve sample preparation devices, each of which meters a defined volume of blood from the same blood input sample.

The integrated fluidic cartridge 148 comprises a first fluidic chamber 44, which serves as the sample input chamber, a first fluidic conduit 20, a first substantially 'V' shaped internal channel 12 in a first rotating valve 10 where the input and output ports are separated by 60 degrees, a second fluidic conduit 22 connected to a second fluidic chamber 46 containing a predefined volume of lysis reagent 132, a third fluidic conduit 24 connected to a third fluidic chamber 48 containing a magnetic flea 128, a fourth fluidic conduit 26 connected to a fourth fluidic chamber 50 containing a magnetic flea 128 and a predefined volume of quench reagent 134. A fifth fluidic conduit 28 is in communication with a first integrated microfluidic cell counter 164, which is in communication with a haemoglobin measurement chamber 168, and then a waste chamber 170. A sixth fluidic conduit 30 serves to put the first rotating valve 10 in communication with the second rotating valve 152. The first fluidic conduit 20, the second fluidic conduit 22, the third fluidic conduit 24, the fourth fluidic conduit 26, the fifth fluidic conduit 28, and the sixth fluidic conduit 30 are all centered around the first rotating valve 10, with sequentially adjacent fluidic conduits angularly separated by 60 degrees.

The sixth fluidic conduit 30 is in communication with the second rotating valve 152, which contains a second substantially 'V' shaped internal channel 72. The second internal channel 72 has an input and output port separated by 30 degrees. The seventh fluidic conduit 32 is in communication with a fifth fluidic chamber 52 which serves as an air vent. An eighth fluidic conduit 34 is in communication with a sixth fluidic chamber 54, which contains a predefined volume of diluting reagent 150. The ninth fluidic conduit 36 is in communication with a seventh fluidic chamber 56 which contains a magnetic flea 128. The tenth fluidic conduit 38 is in communication with an eighth fluidic chamber 58, which serves as an air vent. The eleventh fluidic conduit 40 is in communication with a ninth fluidic chamber 60 which contains a predefined volume of diluting reagent 150. A twelfth fluidic conduit 42 is in communication with a tenth fluidic chamber 62 which contains a magnetic flea 128. A thirteenth fluidic conduit 154 is in communication with an eleventh fluidic chamber 64 which acts as an air vent. The fourteenth fluidic conduit 156 is in communication with a twelfth fluidic chamber 66 which contains a defined volume of diluting reagent 150. A fifteenth fluidic conduit 158 is in communication with a thirteenth fluidic chamber 162 which contains a magnetic flea 128. The sixteenth fluidic conduit 160 is in communication with a second microfluidic cell counter 166, which in turn is in communication with a waste chamber 170. The sixth fluidic conduit 30, the seventh fluidic conduit 32, the eighth fluidic conduit 34, the ninth fluidic conduit 36, the tenth fluidic conduit 38, the eleventh fluidic conduit 40, the twelfth fluidic conduit 42, the thirteenth fluidic conduit 154, the fourteenth fluidic conduit 156, the fifteenth fluidic conduit 158, and the sixteenth fluidic conduit 160 are all centered around the second rotating valve 152, with sequentially adjacent fluidic conduits angularly separated by 30 degrees.

The first rotating valve meters a first defined volume of blood that will be processed in order to count WBCs, while the second rotating valve meters a second defined volume of blood that will be processed in order to count RBCs and platelets. There are two integrated cell counters; one for counting the numbers of WBCs, and another for counting RBCs and platelets in the processed blood samples. The waste chamber collects and stores the processed blood after counting.

Whole blood is input via the first fluidic chamber 44, the first fluidic conduit 20, the first internal channel 12 in the first rotating valve 10, the sixth fluidic conduit 30, the second internal channel 72 in the second rotating valve 152, and at least partially into the seventh fluidic conduit 32. Preferably, capillary forces draw the blood sample into the first fluidic conduit 20, through the internal channel 12 in the first rotating valve 10, through the sixth fluidic conduit 30, into the second internal channel 72 of the second rotating valve 152 and into the seventh fluidic conduit 32.

The blood that is input into the device may be exposed to an anti-coagulant agent, e.g. EDTA salts, heparin and the like. The first fluidic chamber, the first fluidic conduit, the internal channel in the first rotating valve, the sixth fluidic conduit, and/or the internal channel in the second rotating valve may have their surfaces pre-treated with such an anti-coagulation agent. Such compounds may be adhered to the surfaces of the channel walls. Alternatively, anti-coagulation agents may be added to the pre-loaded fluid in the first fluidic chamber and the sixth fluidic chamber.

The blood that filled the internal channel 12 of the first rotating valve 10 will be processed as to enable the WBCs to be counted. The first rotating valve 10 is rotated clockwise by 120 degrees, metering a defined volume of whole blood in the internal channel 12 within the first rotating valve 10, and connecting the second fluidic conduit 22 to the third fluidic conduit 24 via the internal channel 12 in the first rotating valve 10. Positive gas pressure is used to force the defined volume of lysis reagent 132 out of the second fluidic chamber 46, flushing the metered blood sample out of the internal channel 12 in the first rotating valve 10, and into the third fluidic chamber 48 via the third fluidic conduit 24. The blood is lysed in the third fluidic chamber 48 for a pre-determined length of time with a magnetic flea 128 generating both mixing and shearing.

The first rotating valve 10 is rotated clockwise by 60 degrees joining the third fluidic conduit 24 to the fourth fluidic conduit 26. The fourth fluidic chamber 50 contains a pre-defined volume of quench reagent 134. Positive gas pressure is used to transfer the lysed blood from the third fluidic chamber 48 to the fourth fluidic chamber 50, via the third fluidic conduit 24, the internal channel 12 in the first rotating valve 10, and the fourth fluidic conduit 26, where the chemical lysing process is halted by the defined volume of quench reagent 134. A magnetic flea 128 mixes the lysed blood with the defined volume of quench reagent 134 for a pre-determined length of time.

The first rotating valve 10 is turned a further 45 degrees in the clockwise direction, connecting the fourth fluidic conduit 26 to the fifth fluidic conduit 28, which in turn is in communication with the first microfluidic cell counter 164. Positive gas pressure applied to the fourth fluidic chamber 50 forces the lysed and quenched blood sample through the first microfluidic cell counter 164 at a constant flow rate, via the fourth fluidic conduit 26, the internal channel 12 in the first rotating valve 10, and the fifth fluidic conduit 28, enabling the WBCs to be counted.

The lysis reagent is any reagent mixture that contains a chemical known to lyse RBCs, e.g. saponins, quarternary ammonium salts and the like. The lysis reagent used may contain saponin. The lysis reagent may be 0.12% v/v formic acid and 0.05% w/v saponin. The quench reagent is any reagent mixture known to halt or substantially reduce the rate of RBC lysis. The quench reagent may be 0.6% w/v sodium carbonate and 3% w/v sodium chloride. The blood:lysis:quench reagents may be mixed in a ratio of 1:12:5.3. The internal channel in the first rotating valve may have a volume 1-20 ul, or 1-10 ul, or 3-5 ul. The internal channel in the rotating valve may have a volume of 5 ul, and thus meter 5 ul of whole blood. 60 ul of 0.12% v/v formic acid and 0.05% w/v saponin may be pre-loaded into the second fluidic chamber, and 26.5 ul of 0.6% w/v sodium carbonate and 3% w/v sodium chloride may be pre-loaded into the fourth fluidic chamber. After metering, lysing and quenching, a total volume of lysed and quenched blood will be 91.5 ul.

The blood that filled the second 'V' shaped internal channel 72 of the second rotating valve 152 will be processed as to enable the RBCs and platelets to be counted. The second rotating valve 152 is rotated anti-clockwise by 60 degrees, metering a second defined volume of whole blood within the second internal channel 72 in the second rotating valve 152, and putting the eighth fluidic conduit 34 in communication with the ninth fluidic conduit 36 via the second internal channel 72 in the second rotating valve 152.

Positive gas pressure applied to the sixth fluidic chamber 54 forces the defined volume of dilutent reagent 150 out of the sixth fluidic chamber 54, through the eighth fluidic conduit 34, flushing the second metered defined volume of whole blood into the seventh fluidic chamber 56, via the ninth fluidic conduit 36, where the sample is mixed using a magnetic flea 128 to achieve a first 1:21.5 dilution.

The second rotating valve 152 is rotated a further 30 degrees in the anti-clockwise direction to join the ninth fluidic conduit 36 with the tenth fluidic conduit 38. Positive gas pressure is applied to the seventh fluidic chamber 56 to force the first diluted blood through the ninth fluidic conduit 36, into the second internal channel 72 in the second rotating valve 152 and at least partially into the tenth fluidic conduit 38.

At this point, the rotating valve is rotated anti-clockwise by 60 degrees, metering a defined volume of first diluted blood inside the second internal channel in the second rotating valve 152, and joining together the eleventh fluidic conduit 40 to the twelfth fluidic conduit 42 via the second internal channel 72 in the second rotating valve 152. The ninth fluidic chamber 60 is pre-filled with a predefined volume of a dilutent reagent 150, and the tenth fluidic chamber 62 contains a magnetic flea 128.

Positive gas pressure applied to the ninth fluidic chamber 60 forces the predefined volume of dilutent reagent 150 through the eleventh fluidic conduit 40, the second internal channel 72 in the second rotating valve 152, through the twelfth fluidic conduit 42 and into the tenth fluidic chamber 62, flushing the metered volume of first diluted blood out of the second internal channel 72 in the second rotating valve 152 and into the tenth fluidic chamber 62, via the twelfth fluidic conduit 42, in the process. The metered volume of first diluted blood is mixed with the second predefined volume of dilutent reagent using a magnetic flea 128 in the tenth fluidic chamber 62 to achieve a second 1:21.5 dilution.

The second rotating valve 152 is rotated a further 30 degrees in the anti-clockwise direction to join the twelfth fluidic conduit 42 with the thirteenth fluidic conduit 154 via the second internal channel 72 in the second rotating valve 152. Positive gas pressure is applied to the twelfth fluidic chamber 62 to force the second diluted blood through the twelfth fluidic conduit 42, into the second internal channel 72 in the second rotating valve 152, and at least partially into the thirteenth fluidic conduit 154.

At this point, the second rotating valve 152 is rotated anti-clockwise by 60 degrees, thus metering a defined volume of second diluted blood inside the internal channel 72 in the second rotating valve 152, and joining together the fourteenth fluidic conduit 156 to the fifteenth fluidic conduit 158 via the second internal channel 72 in the second rotating valve 152. The twelfth fluidic chamber 66 is pre-filled with a predefined volume of a dilutent reagent 150, and the thirteenth fluidic chamber 162 contains a magnetic flea 128.

Positive gas pressure applied to the twelfth fluidic chamber 66 forces the predefined volume of dilutent reagent 150 through the fourteenth fluidic conduit 156, the second internal channel 72 in the second rotating valve 152, the fifteenth fluidic conduit 158 and into the thirteenth fluidic chamber 162, flushing the metered volume of second diluted blood out of the second internal channel 72 in the second rotating valve 152 and into the thirteenth fluidic chamber 162, via the fifteenth fluidic conduit 158, in the process. The metered volume of second diluted blood is mixed with the second defined volume of dilutent reagent using a magnetic flea 128 in the thirteenth fluidic chamber 162 to achieve a third 1:21.5 dilution.

Once mixed, the second rotating valve 152 is rotated an additional 30 degrees in the anti-clockwise direction to bring the fifteenth fluidic conduit 158 into communication with the sixteenth fluidic conduit 160 via the second internal channel 72 in the second rotating valve 152. Positive gas pressure applied to the thirteenth fluidic chamber 162 forces the 1:9,938 diluted blood sample through the fifteenth fluidic conduit 158, the second internal channel 72 in the second rotating valve 152, through the sixteenth fluidic conduit 160 and then through second microfluidic cell counter 166 at a constant flow rate, allowing the RBCs and platelets to be counted.

The second internal channel in the second rotating valve may have a volume of 1-10 ul, or 1-5 ul, or 3 ul. In one embodiment, the second internal channel in the second rotating valve will meter 3 ul of whole blood, and subsequently meter 3 ul of first diluted blood, and 3 ul of second diluted blood. The sixth fluidic chamber, ninth fluidic chamber and twelfth fluidic chamber may each be pre-loaded with 3*21.5=64.5 ul of dilutent reagent. The diluent reagent is one compatible with RBCs and platelets. Compatible implies that the reagent in question does not cause serious degradation to the sample, nor promotes clotting of either the RBCs or the platelets. Dilutent reagents may include, but are not limited to, PBS, running buffer (comprising PBS, 2 mM EDTA, 0.5% BSA), and the like.

The first and second microfluidic cell counters may be microchannel impedance sensors with at least two pairs of electrodes for measuring a differential current as a blood cell passes between the two electrodes of the first electrode pair, then the two electrodes of the second electrode pair. The microfluidic channel within the impedance sensor may have a cross-section that is 40 um×40 um square, with each electrode in the first and second electrode pairs also measuring 40 um×40 um square. The fluid containing the blood cells to be counted may be pumped through the microchannel impedance sensor at a constant flow rate, e.g., at a flow rate of 40 ul/min.

The embodiment may further comprise a haemoglobin measurement in a haemoglobin measurement chamber 168. For haemoglobin to be measured accurately, the RBCs must be lysed. It follows that the most preferable position for the haemoglobin measurement is after the RBCs have been lysed in the WBC counting protocol. It is further preferable to convert the haemoglobin into a stable oxidized form (methemoglobin) by adding chemical haemoglobin reagent mixtures. Suitable reagents include, but are not limited to, Drabkins's reagent (which contains sodium bicarbonate, potassium ferricyanide and potassium cyanide and converts haemoglobin into cyanmethemoglobin), ferrocyanide, or the like. Such haemoglobin reagents could be pre-dried in the haemoglobin measurement chamber 168. In practice, haemoglobin is converted to cyanmethemoglobin (e.g. by reacting the blood with a Drabkin's reagent) and measured spectrophotometrically (the reacted Drabkin's reagent and haemoglobin form a stable, coloured end-product). A simple LED/photodiode combination can be employed for the quantitative, colourimetric determination of blood haemoglobin using absorbance in accordance with Beer's law, as is known in the art.

After cell counting, and the haemoglobin measurement, the processed blood samples are collected in a waste chamber 170.

The two different sample processing protocols for WBCs and RBCs/platelets may be carried out simultaneously and the cells of interest counted on separate impedance sensors. An alternative embodiment would carry out the processing protocols for WBCs and RBCs/platelets in parallel, and then count e.g. the WBCs then the RBCs/platelets on a single impedance chip in series. In a further alternative embodiment, the two different sample processing protocols could be carried out in series and the e.g. WBCs followed by the RBCs/platelets counted on a single impedance sensor.

Figure 14:
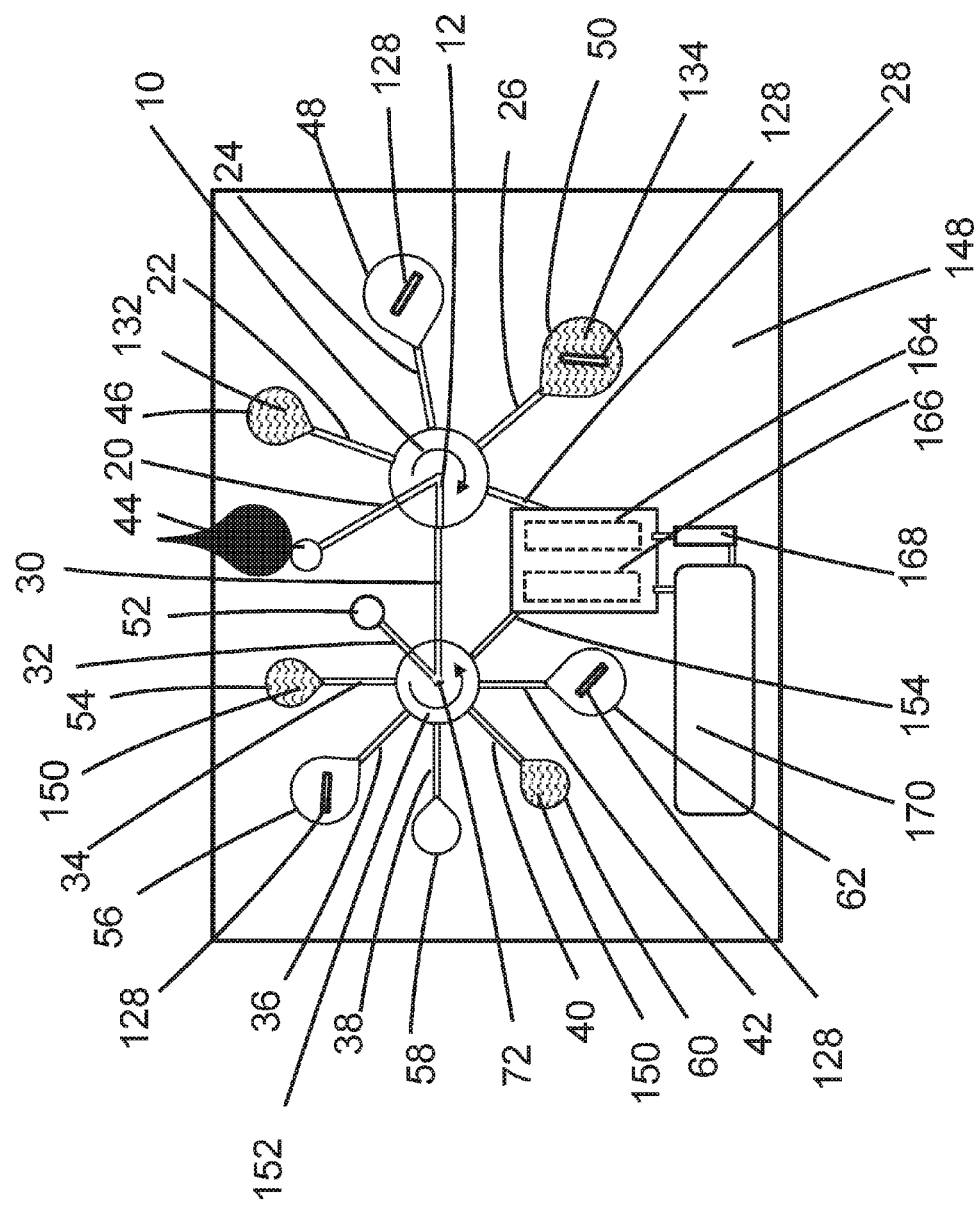
FIG. 14 depicts a second embodiment of the described Example 4.

FIG. 14 depicts an alternative embodiment of the microfluidic cartridge for preparing a blood sample for counting WBCs, and RBCs and platelets. In this embodiment, the integrated fluidic cartridge 148 comprises a first fluidic chamber 44, which serves as the sample input chamber, a first fluidic conduit 20, a first substantially 'V' shaped internal channel 12 in a first rotating valve 10 where the input and output ports are separated by 60 degrees, a second fluidic conduit 22 connected to a second fluidic chamber 46 containing a predefined volume of lysis reagent 132, a third fluidic conduit 24 connected to a third fluidic chamber 48 containing a magnetic flea 128, a fourth fluidic conduit 26 connected to a fourth fluidic chamber 50 containing a magnetic flea 128 and a predefined volume of quench reagent 134. A fifth fluidic conduit 28 is in communication with a first integrated microfluidic cell counter 164, which is in communication with a haemoglobin measurement chamber 168, and then a waste chamber 170. A sixth fluidic conduit 30 serves to put the first rotating valve 10 in communication with the second rotating valve 152. The first fluidic conduit 20, the second fluidic conduit 22, the third fluidic conduit 24, the fourth fluidic conduit 26, the fifth fluidic conduit 28, and the sixth fluidic conduit 30 are all centered around the first rotating valve 10, with sequentially adjacent fluidic conduits angularly separated by 60 degrees.

The sixth fluidic conduit 30 is in communication with the second rotating valve 152, which contains a second substantially 'V' shaped internal channel 72. The second internal channel 72 has an input and output port separated by 45 degrees. The seventh fluidic conduit 32 is in communication with a fifth fluidic chamber 52 which serves as an air vent. An eighth fluidic conduit 34 is in communication with a sixth fluidic chamber 54, which contains a predefined volume of diluting reagent 150. The ninth fluidic conduit 36 is in communication with a seventh fluidic chamber 56 which contains a magnetic flea 128. The tenth fluidic conduit 38 is in communication with an eighth fluidic chamber 58, which serves as an air vent. The eleventh fluidic conduit 40 is in communication with a ninth fluidic chamber 60 which contains a predefined volume of diluting reagent 150. A twelfth fluidic conduit 42 is in communication with a tenth fluidic chamber 62 which contains a magnetic flea 128. A thirteenth fluidic conduit 154 is in communication with a second microfluidic cell counter 166, which in turn is in communication with a waste chamber 170.

The sixth fluidic conduit 30, the seventh fluidic conduit 32, the eighth fluidic conduit 34, the ninth fluidic conduit 36, the tenth fluidic conduit 38, the eleventh fluidic conduit 40, the twelfth fluidic conduit 42, and the thirteenth fluidic conduit 154, are all centered around the second rotating valve 152, with sequentially adjacent fluidic conduits angularly separated by 45 degrees.

In this embodiment, 1:100 dilutions are carried out in two dilution steps using the second rotating valve for preparing a whole blood sample for a final 1:10,000 dilution in order to count RBCs and platelets.

Example 4 describes the various details of a blood counting process. More generally, an aspect of the invention is a microfluidic cartridge for performing a full blood count. The microfluidic cartridge includes a housing including a plurality of fluidic conduits, and a plurality of fluidic chambers in fluid connection with respective ones of the plurality of fluidic conduits. The plurality of fluidic chambers includes at least one blood sample input chamber, a plurality of blood reagent chambers, and a plurality of blood sample mixing chambers. The microfluidic cartridge further includes at least one blood cell counter connectable to another one of the plurality of fluidic conduits for counting white blood cells, red blood cells and/or platelets. A first rotating valve has a first internal channel for connecting in fluid communication pairs of the plurality of fluidic conduits. The first rotating valve is rotatable to a first position for metering a first portion of the blood sample from the blood sample input chamber, rotatable to a second position for transferring reagents from blood reagent chambers to the first metered portion of the blood sample, rotatable to a third position to transfer the first metered portion of the blood sample and blood reagents to one of the blood sample mixing chambers to generate a first prepared blood sample, and rotatable to a fourth position to transfer the first prepared blood sample to the at least one blood cell counter for counting the white blood cells. In addition, a second rotating valve has a second internal channel also for connecting in fluid communication pairs of the plurality of fluidic conduits. The second rotating valve is rotatable to a fifth position for metering a second portion of the blood sample from the blood sample input chamber, rotatable to a sixth position for transferring reagents from blood reagent chambers to the second metered portion of the blood sample, rotatable to a seventh position to transfer the second metered portion of the blood sample and blood reagents to another one of the blood sample mixing chambers to generate a second prepared blood sample, and rotatable to an eighth position to transfer the second prepared blood sample to the at least one blood cell counter for counting the red blood cells and platelets.

Example 5—Titration in Duplicate

Figure 15:
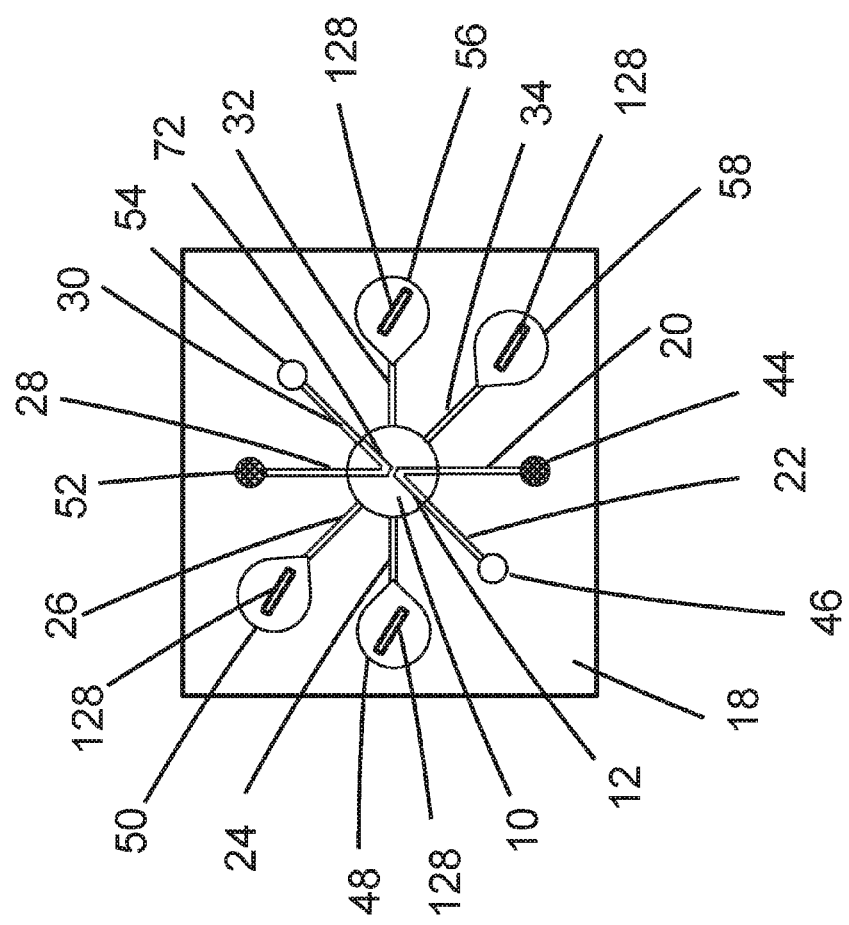
FIG. 15 depicts how the invention is used in accordance with the described Example 5.

FIG. 15 teaches how the invention can be used to carry out accurate titrations in duplicate. In this example, the housing 18 comprises eight fluidic conduits centered around a rotating valve 10, with sequentially adjacent fluidic conduits angularly separated by 45 degrees. The rotating valve 10 contains a first substantially 'V' shaped internal channel 12 and a second substantially 'V' shaped internal channel 72 which are not in communication with each other. Both the first internal channel 12 and second internal channel 72 have input and output ports that are angularly separated by 45 degrees. The third fluidic chamber 48 and the seventh fluidic chamber 56 each contain a predefined volume of an analyte containing solution A1 of unknown concentration with a small volume of indicator (preferably, the indicator changes colour in response to a chemical change).

A titrant solution T0, of known concentration, is introduced to the device through the first fluidic chamber 44, for the primary measurement, and the fifth fluidic chamber 52, for the duplicate measurement. For the primary measurement, the titrant solution T0 is drawn into the first fluidic conduit 20, through the first internal channel 12 in the rotating valve 10, and partially into the second fluidic conduit 22 such as via capillary forces. An analogous process occurs for the duplicate measurement where the titrant solution T0 is drawn through the fifth fluidic conduit 28, through the second internal channel 72 in the rotating valve 10, and partially into the sixth fluidic conduit 30 preferably via capillary forces. After at least a portion of the second fluidic conduit 22 and the sixth fluidic conduit 30 has been filled with the titrant solution T0, the rotating valve 10 is rotated 90 degrees in the clockwise direction. This simultaneously meters a primary volume of titrant solution T1 in the first internal channel 12 in the rotating valve 10, and a second volume of titrant solution T1 in the second internal channel 72 in the rotating valve 10. The third fluidic conduit 24 is put in communication with the fourth fluidic conduit 26 via the first internal channel 12 in the rotating valve 10, while the seventh fluidic conduit 32 is put in communication with the eighth fluidic conduit 34 via the second internal channel 72 in the rotating valve 10.

Positive gas pressure applied to the third fluidic chamber 48, forces the analyte containing solution A1 to flush the primary metered titrant solution T1 out of the first internal channel 12 in the rotating valve 10 and into the fourth fluidic chamber 50. The two liquid samples A1+T1 can then be mixed in the fourth fluidic chamber 50 using the magnetic flea 128. Positive gas pressure simultaneously applied to the seventh fluidic chamber 56 forces the analyst containing solution A1 to flush the duplicate metered titrant solution T1 out of the second internal channel 72 in the rotating valve 10 and into the eighth fluidic conduit 34, then the eighth fluidic chamber 58. The two liquid samples A1+T1 are mixed in the eighth fluidic chamber 58 using the magnetic flea 128.

Optical measurements are made at the fourth fluidic chamber 50 and the eighth fluidic chamber 58 after the first titration to determine whether or not the indicator has changed colour. If the colour has not changed, then further titrations have to be carried out. The endpoint of the reaction is reached when the indicator in the analyte solution changes colour.

The rotating valve 10 is rotated through 90 degrees in the anti-clockwise direction to bring the rotating valve back to its original starting position where the first internal channel 12 puts the first fluidic conduit 20 and the second fluidic conduit 22 into communication, while simultaneously the second internal channel 72 puts the fifth fluidic conduit 28 in communication with the sixth fluidic conduit 30. If necessary, positive or negative gas pressure can be used to force the titrant solution T0 into the first internal channel 12 and the second internal channel 72 in the rotating valve 10. The rotating valve is then rotated 90 degrees in the clockwise direction, thus simultaneously metering a second volume of the titrant solution, T2, in each of the first internal channel 12 and second internal channel 72 in the rotating valve 10. The third fluidic conduit 24 is put in communication with the fourth fluidic conduit 26 via the first internal channel 12 in the rotating valve 10, while the seventh fluidic conduit 32 is put in communication with the eighth fluidic conduit 34 via the second internal channel 72 in the rotating valve 10. Positive gas pressure applied to the fourth fluidic chamber 50, forces the analyte/titrant containing solution A1+T1 to flush the second primary metered titrant solution T2 out of the first internal channel 12 in the rotating valve 10 and into the third fluidic chamber 48. The three liquid samples A1+T1+T2 can then be mixed in the third fluidic chamber 48 using the magnetic flea 128. Positive gas pressure simultaneously applied to the eighth fluidic chamber 58 forces the analyst containing solution A1+T1 to flush the second, duplicate metered titrant solution T2 out of the second internal channel 72 in the rotating valve 10 and into the seventh fluidic conduit 32, then the seventh fluidic chamber 56. The three liquid samples A1+T1+T2 are mixed in the seventh fluidic chamber 56 using the magnetic flea 128. Once suitably mixed, a new set of optical measurements can be made at the third fluidic chamber 48 and the seventh fluidic chamber 56.

The process can be repeated as many times as required, with optical measurements made after each titration, until the indicator has changed colour signifying that the endpoint of the reaction has been reached.

When the endpoint of the reaction is reached, the concentration of the analyte can be determined using Equation 1:

$$Ca=CtVtM/Va \qquad \text{Eqn 1}$$

Where Ca is the concentration of the analyte (mol/liter), Ct is the concentration of the titrant (mol/liter), Vt is the volume of the titrant used in the reaction (liters), and M is the mole ratio of the analyte and titrant from the balanced chemical equation for the reaction, and Va is the volume of the analyte used in the reaction (liters).

For acid-base titrations, a number of different indicators can be used including, but not limited to: methyl violet, methyl orange, methyl red, litmus, bromothymol blue, and alizarin yellow.

Optical measurements to determine when the indicator has changed colour can be simply made by eye, or using a camera. In more sophisticated set-ups, the colour change could be monitored via absorption.

It will be apparent to one skilled in that art that the invention can be configured as to carry out, e.g. titrations in triplicate or quadruplicate etc. as may be desirable.

Example 6—Amide Bond Synthesis

Figure 16:
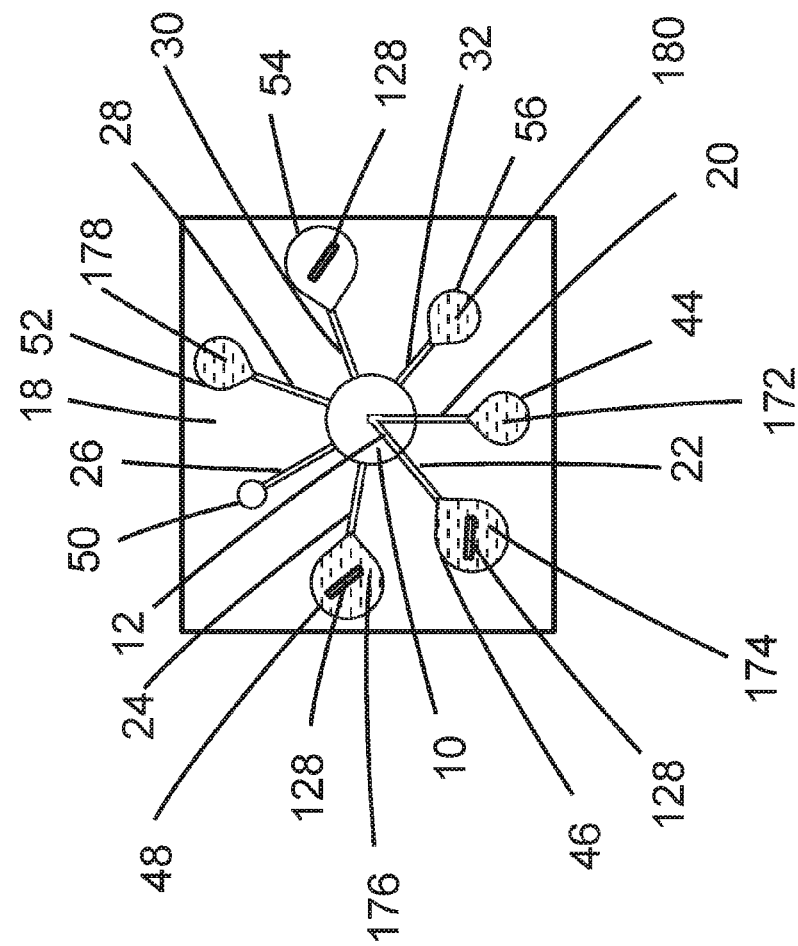
FIG. 16 depicts how the invention is used in accordance with the described Example 6.

FIG. 16 teaches how the invention can be used in amide bond synthesis. A housing 18 contains a rotating valve 10 with an internal channel 12. Seven fluidic conduits are centered around the rotating valve 10, with sequentially adjacent fluidic conduits angularly separated by 50 degrees. The first fluidic conduit 20 is in communication with a first fluidic chamber 44 which contains a defined volume of carboxylic acid solution 172. The second fluidic conduit 22 is in communication with a second fluidic chamber 46 which contains a defined volume of an activating agent 174, e.g. EDC.HCl, and a magnetic flea 128. A third fluidic conduit 24 is in communication with a third fluidic chamber 48 which contains a defined volume of n-hydroxysuccinimide 176 and a magnetic flea 128. A fourth fluidic conduit 26 is in communication with a fourth fluidic chamber 50 which serves as an air vent. A fifth fluidic conduit 28 is in communication with a fifth fluidic chamber 52 which contains a defined volume of pH 8 buffer. A sixth fluidic conduit 30 is in communication with a sixth fluidic chamber 54 which contains a magnetic flea. A seventh fluidic conduit 32 is in communication with a seventh fluidic chamber 56 which contains a defined volume of an amine solution 180.

The rotating valve 10 is positioned as to connect the first fluidic conduit 20 to the second fluidic conduit 22 via the internal channel 12 in the first rotating valve 10. Positive air pressure is applied to the first fluidic chamber 44 to force the defined volume of carboxylic acid solution 172 through the first fluidic conduit 20, through the internal channel 12 in the rotating valve 10, through the second fluidic conduit 22 and into the second fluidic chamber 46 where it is mixed with the defined volume of activating agent 174 using the magnetic flea 128. This produces a highly chemically reactive intermediate solution.

The rotating valve 10 is rotated 50 degrees in the clockwise direction to bring the second fluidic conduit 22 into communication with the third fluidic conduit 24 via the internal channel 12 in the rotating valve 10. Positive air pressure is applied to the second fluidic chamber 46 to force the highly chemically reactive intermediate solution through the second fluidic conduit 22, through the internal channel 12 in the rotating valve 10, through the third fluidic conduit 24 and into the third fluidic chamber 48 where it is mixed with a defined volume of n-hydroxysuccinimide 176 using a magnetic flea 128. This produces an NHS-activated carboxylic acid.

The rotating valve 10 is rotated 50 degrees in the clockwise direction to bring the third fluidic conduit 24 into communication with the fourth fluidic conduit 26 via the internal channel 12 in the rotating valve 10. Positive air pressure is applied to the third fluidic chamber 48 to force the NHS-activated carboxylic acid out of the third fluidic chamber, through the third fluidic conduit 24, into the internal channel 12 in the rotating valve 10 and at least partially into the fourth fluidic conduit 26.

The rotating valve is rotated a further 100 degrees in the clockwise direction to isolate the metered volume of NHS-activated carboxylic acid in the internal channel in the rotating valve from the third fluidic conduit and the fourth fluidic conduit, and to further bring the fifth fluidic conduit 28 into communication with the sixth fluidic conduit 30 via said internal channel 12 in the rotating valve 10 containing said metered volume of NHS-activated carboxylic acid.

Positive air pressure is applied to the fifth fluidic chamber 52 to force the defined volume of pH 8 buffer out of the fifth fluidic chamber, through the fifth fluidic conduit 28, through the internal channel 12 in the rotating valve 10, through the sixth fluidic conduit 30 and into the sixth fluidic chamber 54, flushing the metered volume of NHS-activated carboxylic acid into the sixth fluidic chamber in the process. The NHS-activated carboxylic acid is mixed with the defined volume of pH 8 buffer in the sixth fluidic chamber using a magnetic flea 128, resulting in a 1:10 dilution of the NHS-activated carboxylic acid.

The rotating valve is rotated 50 degrees in the clockwise direction bringing the sixth fluidic conduit 30 into communication with the seventh fluidic conduit 32 via the internal channel 12 in the rotating valve 10. Positive air pressure is applied to the seventh fluidic chamber 56 to force the defined volume of an amine solution 180 out of the seventh fluidic chamber, through the seventh fluidic conduit 32, through the internal channel 12 in the rotating valve 10, through the sixth fluidic conduit 30 and into the sixth fluidic chamber 54 where it is mixed with the 1:10 diluted NHS-activated carboxylic acid using the magnetic flea 128. A chemical reaction takes place resulting in the formation of an amide linked product where the acid component of the NHS-activated carboxylic acid links with the amine in the amine solution.

In accordance with the above description, an aspect of the invention is an integrated microfluidic device for carrying out a series of fluidic operations. Embodiments of the integrated microfluidic device include a housing including a plurality of n microfluidic conduits, wherein n is at least three, and a rotating valve having an internal channel with an entrance port and an exit port that are angularly separated. The rotating valve is positionable in a first position to connect two of the n fluidic conduits via the internal channel, and upon rotating the valve to a second position, two of the n fluidic conduits, including at least one fluidic conduit different from the fluidic conduits connected in the first position, are connected by the internal channel. In either the first position or the second position, two sequentially adjacent fluidic conduits are connected via the internal channel.

In exemplary embodiments of the integrated microfluidic device, the two of the n fluidic conduits connected in the second position includes at least one of the fluidic conduits connected to the internal channel in the first position.

In exemplary embodiments of the integrated microfluidic device, n is from 5 through 36 fluidic conduits.

In exemplary embodiments of the integrated microfluidic device, the angle of separation of the entrance port and exit port is at least ten degrees and equal to or less than sixty degrees.

In exemplary embodiments of the integrated microfluidic device, the internal channel is at least one of "V" shaped, "U" shaped, or "L" shaped to angularly separate the entrance port and the exit port.

In exemplary embodiments of the integrated microfluidic device, the device further includes a first fluidic chamber in fluid communication with one of the fluidic conduits, wherein fluid contained in the first fluidic chamber is transferrable by application of positive or negative displacement pressure from the first fluidic chamber through the one of the fluidic conduits, and via the entrance port into the internal channel.

In exemplary embodiments of the integrated microfluidic device, the fluid is transferrable by the application of the positive or negative displacement pressure from the internal channel via the exit port into a second one of the fluidic conduits.

In exemplary embodiments of the integrated microfluidic device, the device further includes a second fluidic chamber in fluid communication with the second one of the fluidic conduits, wherein the fluid is transferrable from the second one of the fluidic conduits into the second fluidic chamber.

In exemplary embodiments of the integrated microfluidic device, the second fluidic chamber includes a magnetic flea for at least one of mixing or lysing fluid contained within the second fluidic chamber.

In exemplary embodiments of the integrated microfluidic device, the first fluidic chamber includes a magnetic flea for at least one of mixing or lysing fluid contained within the second fluidic chamber.

In exemplary embodiments of the integrated microfluidic device, the first fluidic chamber includes a first moveable piston that applies the positive or negative displacement pressure to transfer the fluid from the first fluidic chamber.

In exemplary embodiments of the integrated microfluidic device, the second fluidic chamber includes a second moveable piston to control the transfer of fluid into the second fluidic chamber.

In exemplary embodiments of the integrated microfluidic device, the second fluidic chamber includes a vent that vents excess gas that is pumped into the second fluidic chamber by the movement of the first and/or second moveable pistons.

In exemplary embodiments of the integrated microfluidic device, the magnetic flea is configured in accordance with at least one of the following conditions: an aspect ratio of a height of liquid in the second fluidic chamber to a width of fluid in the second fluidic chamber is from 0.1 to 2.0; a ratio of a length of the magnetic flea to a diameter of the second fluidic chamber is greater than 0.5; and the magnetic flea is rotatable at least at 300 rpm.

In exemplary embodiments of the integrated microfluidic device, at least one of the fluidic conduits and/or fluidic chambers includes at least one sensor.

In exemplary embodiments of the integrated microfluidic device, the at least one sensor is at least one of an impedance sensor, pH sensor, temperature sensor, flow sensor, optical sensor, chemical sensor, EWOD, AM-EWOD.

In exemplary embodiments of the integrated microfluidic device, the sensor is a plurality of optical sensors configured to take a series of optical measurements in at least two fluidic chambers, and to compare the optical measurements against a calibration curve to determine a volume of fluid metered in the internal channel of the rotating valve.

In exemplary embodiments of the integrated microfluidic device, the device further includes a second rotating valve having an internal channel with an entrance port and an exit port that are angularly separated, wherein at least one of the rotating valve and second rotating valve can be rotated such that the rotating valve and second rotating valve are in fluid communication with each other via a fluidic conduit.

Another aspect of the invention is a microfluidic cartridge for performing a full blood cell count. The microfluidic cartridge includes a housing including a plurality of fluidic conduits; a plurality of fluidic chambers in fluid connection with respective ones of the plurality of fluidic conduits, wherein the plurality of fluidic chambers includes at least one blood sample input chamber, a plurality of blood reagent chambers, and a plurality of blood sample mixing chambers; at least one blood cell counter connectable to at least one of the plurality of fluidic conduits capable of counting at least one of white blood cells, red blood cells or platelets; and a first rotating valve having a first internal channel for connecting in fluid communication pairs of the plurality of fluidic conduits. The first rotating valve is rotatable to a first position for metering a first portion of the blood sample from the blood sample input chamber, rotatable to a second position for transferring reagents from blood reagent chambers to the first metered portion of the blood sample, rotatable to a third position to transfer the first metered portion of the blood sample and blood reagents to one of the blood sample mixing chambers to generate a first prepared blood sample, and rotatable to a fourth position to transfer the first prepared blood sample to the at least one blood cell counter for counting the white blood cells. The cartridge further includes a second rotating valve having a second internal channel for connecting in fluid communication pairs of the plurality of fluidic conduits. The second rotating valve is rotatable to a fifth position for metering a second portion of the blood sample from the blood sample input chamber, rotatable to a sixth position for transferring reagents from blood reagent chambers to the second metered portion of the blood sample, rotatable to a seventh position to transfer the second metered portion of the blood sample and blood reagents to another one of the blood sample mixing chambers to generate a second prepared blood sample, and rotatable to an eighth position to transfer the second prepared blood sample to the at least one blood cell counter for counting the red blood cells and platelets.

Another aspect of the invention is a method of performing a series of fluid operations in an integrated microfluidic device. The method includes the steps of providing a housing including a plurality of n microfluidic conduits, wherein n is at least three; providing a rotating valve having an internal channel with an entrance port and an exit port that are angularly separated; positioning the rotating valve in a first position to connect two of the n fluidic conduits via the internal channel; transferring at least a portion of a fluid from a first one of the n fluidic conduits into a second one of the n fluidic conduits connected to the first fluidic conduit via the internal channel; rotating the rotating valve to a second position in which a third one of the n fluidic conduits is connected via the internal channel to the second fluidic conduit; transferring at least a portion of fluid between the second fluidic conduit and the third fluidic conduit via the internal channel; and performing at least one fluidic operation on the fluid.

In exemplary embodiments of the method of performing a series of fluid operations, the at least one fluidic operation includes at least one of metering or re-metering the fluid; mixing constituents within the fluid; labelling, incubating, lysing, quenching, diluting, titrating, or separating constituents within the fluid; and transferring the fluid between external conduits and/or chambers in fluid communication with one or more of the n fluidic conduits.

While the invention has been described with respect to a certain embodiment, or embodiments, equivalent modifications and alterations may occur to one skilled in the art, within the spirit and scope of the appended claims, upon the reading and understanding of the specification and the annexed drawings. In addition, while a particular feature of the invention may have been described with respect to only one or more of several embodiments, such features may be combined with one or more other features of different embodiments as may be desired and advantageous for any given or particular application.

INDUSTRIAL APPLICABILITY

The microfluidic device could form a part of a lab-on-a-chip system. Such devices could be used in metering, mixing, reacting, lysing, quenching, binding, labeling and/or sensing chemical, biochemical, physiological, and/or environmental fluids.

The microfluidic device could further form part of a point-of-care diagnostic testing system for cell counting, e.g. full blood count and analysis.

The invention claimed is:
1. An integrated microfluidic device for carrying out a series of fluidic operations comprising:
   a housing including a plurality of n microfluidic conduits, wherein n is at least three; and
   a rotating valve having an internal channel with an entrance port and an exit port that are angularly separated;
   wherein the rotating valve is positionable in a first position to connect two of the n fluidic conduits via the internal channel, and upon rotating the valve to a second position, two of the n fluidic conduits, including at least one fluidic conduit different from the fluidic conduits connected in the first position, are connected by the internal channel; and wherein in either the first position or the second position, two sequentially adjacent fluidic conduits are connected via the internal channel;

further comprising a first fluidic chamber in fluid communication with one of the fluidic conduits, wherein fluid contained in the first fluidic chamber is transferrable by application of positive or negative displacement pressure from the first fluidic chamber through the one of the fluidic conduits, and via the entrance port into the internal channel;

wherein the fluid is transferrable by the application of the positive or negative displacement pressure from the internal channel via the exit port into a second one of the fluidic conduits;

further comprising a second fluidic chamber in fluid communication with the second one of the fluidic conduits, wherein the fluid is transferrable from the second one of the fluidic conduits into the second fluidic chamber; and wherein the first fluidic chamber includes a first moveable piston that applies the positive or negative displacement pressure to transfer the fluid from the first fluidic chamber.

2. The integrated microfluidic device of claim 1, wherein the two of the n fluidic conduits connected in the second position includes at least one of the fluidic conduits connected to the internal channel in the first position.

3. The integrated microfluidic device of claim 1, wherein n is from 5 through 36 fluidic conduits.

4. The integrated microfluidic device of claim 1, wherein the angle of separation of the entrance port and exit port is at least ten degrees and equal to or less than sixty degrees.

5. The integrated microfluidic device of claim 1, wherein the internal channel is at least one of "V" shaped, "U" shaped, or "L" shaped to angularly separate the entrance port and the exit port.

6. The integrated microfluidic device of claim 1, wherein the second fluidic chamber includes a magnetic flea for at least one of mixing or lysing fluid contained within the second fluidic chamber.

7. The integrated microfluidic device of claim 1, wherein the first fluidic chamber includes a magnetic flea for at least one of mixing or lysing fluid contained within the second fluidic chamber.

8. The integrated microfluidic device of claim 1, wherein the second fluidic chamber includes a second moveable piston to control the transfer of fluid into the second fluidic chamber.

9. The integrated microfluidic device of claim 8, wherein the second fluidic chamber includes a vent that vents excess gas that is pumped into the second fluidic chamber by the movement of the first and/or second moveable pistons.

10. The integrated microfluidic device of claim 6, wherein the magnetic flea is configured in accordance with at least one of the following conditions:
   an aspect ratio of a height of liquid in the second fluidic chamber to a width of fluid in the second fluidic chamber is from 0.1 to 2.0;
   a ratio of a length of the magnetic flea to a diameter of the second fluidic chamber is greater than 0.5; and
   the magnetic flea is rotatable at least at 300 rpm.

11. The integrated microfluidic device of claim 1, wherein at least one of the fluidic conduits and/or fluidic chambers includes at least one sensor.

12. The integrated microfluidic device of claim 11, wherein the at least one sensor is at least one of an impedance sensor, pH sensor, temperature sensor, flow sensor, optical sensor, chemical sensor, EWOD, AM-EWOD.

13. The integrated microfluidic device of claim 12, wherein the sensor is a plurality of optical sensors configured to take a series of optical measurements in at least two fluidic chambers, and to compare the optical measurements against a calibration curve to determine a volume of fluid metered in the internal channel of the rotating valve.

14. An integrated microfluidic device for carrying out a series of fluidic operations comprising:
   a housing including a plurality of n microfluidic conduits, wherein n is at least three; and
   a rotating valve having an internal channel with an entrance port and an exit port that are angularly separated;
   wherein the rotating valve is positionable in a first position to connect two of the n fluidic conduits via the internal channel, and upon rotating the valve to a second position, two of the n fluidic conduits, including at least one fluidic conduit different from the fluidic conduits connected in the first position, are connected by the internal channel; and
   wherein in either the first position or the second position, two sequentially adjacent fluidic conduits are connected via the internal channel; and
   further comprising a second rotating valve having an internal channel with an entrance port and an exit port that are angularly separated, wherein at least one of the rotating valve and second rotating valve can be rotated such that the rotating valve and second rotating valve are in fluid communication with each other via a fluidic conduit.

15. A microfluidic cartridge for performing a full blood cell count comprising:
   a housing including a plurality of fluidic conduits;
   a plurality of fluidic chambers in fluid connection with respective ones of the plurality of fluidic conduits, wherein the plurality of fluidic chambers includes at least one blood sample input chamber, a plurality of blood reagent chambers, and a plurality of blood sample mixing chambers;
   at least one blood cell counter connectable to at least one of the plurality of fluidic conduits capable of counting at least one of white blood cells, red blood cells or platelets;
   a first rotating valve having a first internal channel for connecting in fluid communication pairs of the plurality of fluidic conduits;
   wherein the first rotating valve is rotatable to a first position for metering a first portion of the blood sample from the blood sample input chamber, rotatable to a second position for transferring reagents from blood reagent chambers to the first metered portion of the blood sample, rotatable to a third position to transfer the first metered portion of the blood sample and blood reagents to one of the blood sample mixing chambers to generate a first prepared blood sample, and rotatable to a fourth position to transfer the first prepared blood sample to the at least one blood cell counter for counting the white blood cells; and a second rotating valve having a second internal channel for connecting in fluid communication pairs of the plurality of fluidic conduits;

wherein the second rotating valve is rotatable to a fifth position for metering a second portion of the blood sample from the blood sample input chamber, rotatable to a sixth position for transferring reagents from blood reagent chambers to the second metered portion of the blood sample, rotatable to a seventh position to transfer the second metered portion of the blood sample and blood reagents to another one of the blood sample mixing chambers to generate a second prepared blood sample, and rotatable to an eighth position to transfer the second prepared blood sample to the at least one blood cell counter for counting the red blood cells and platelets.

\* \* \* \* \*